United States Patent
Qiao

(10) Patent No.: US 7,115,646 B2
(45) Date of Patent: Oct. 3, 2006

(54) CYCLIC DIAMINES AND DERIVATIVES AS FACTOR XA INHIBITORS

(75) Inventor: Jennifer X. Qiao, Princeton, NJ (US)

(73) Assignee: Bristol Myers Squibb, Co., Princeton, NJ (US)

( * ) Notice: Subject to any disclaimer, the term of this patent is extended or adjusted under 35 U.S.C. 154(b) by 3 days.

(21) Appl. No.: 10/959,724

(22) Filed: Oct. 6, 2004

(65) Prior Publication Data

US 2005/0085511 A1    Apr. 21, 2005

Related U.S. Application Data

(60) Provisional application No. 60/509,587, filed on Oct. 8, 2003.

(51) Int. Cl.
| | |
|---|---|
| A61K 31/417 | (2006.01) |
| A61K 31/4184 | (2006.01) |
| C07D 233/24 | (2006.01) |
| C07D 233/61 | (2006.01) |
| C07D 233/64 | (2006.01) |
| A61K 31/536 | (2006.01) |
| A61K 31/4725 | (2006.01) |
| A61K 31/498 | (2006.01) |
| C07D 265/02 | (2006.01) |
| C07D 217/22 | (2006.01) |
| C07D 237/30 | (2006.01) |

(52) U.S. Cl. .................. 514/397; 514/394; 514/230.5; 514/310; 514/248; 548/335.5; 548/309.7; 548/343.5; 544/63; 544/237; 546/139

(58) Field of Classification Search .................... None
See application file for complete search history.

(56) References Cited

U.S. PATENT DOCUMENTS

| | | | |
|---|---|---|---|
| 6,472,386 B1 | 10/2002 | Kodama et al. | |
| 6,632,810 B1 | 10/2003 | Kodama et al. | |
| 6,686,353 B1 | 2/2004 | Shiota et al. | |
| 2005/0119486 A1* | 6/2005 | Ohta et al. .................. | 546/256 |
| 2005/0245565 A1* | 11/2005 | Ohta et al. .................. | 514/300 |

FOREIGN PATENT DOCUMENTS

| | | |
|---|---|---|
| WO | 2004/0172063 | 10/2001 |
| WO | 2004/0119486 | 1/2003 |
| WO | 2005/0245565 | 1/2003 |
| WO | WO 03/045912 | 6/2003 |

* cited by examiner

Primary Examiner—Kamal A. Saeed
Assistant Examiner—Nyeemah Grazier
(74) Attorney, Agent, or Firm—Jing G. Sun; David H. Vance

(57) ABSTRACT

The present application describes cyclic diamino compounds, derivatives thereof, and pharmaceutically acceptable salt forms thereof, which are useful as inhibitors of factor Xa.

20 Claims, No Drawings

CYCLIC DIAMINES AND DERIVATIVES AS FACTOR XA INHIBITORS

CROSS-REFERENCE TO RELATED APPLICATIONS

The present application claims the priority benefit of U.S. Provisional Application No. 60/509,587, filed Oct. 8, 2003, which is expressly incorporated fully herein by reference.

FIELD OF THE INVENTION

This invention relates generally to cyclic diamino compounds, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and, (g) factors that improve manufacturing costs or feasibility.

SUMMARY OF THE INVENTION

Accordingly, the present invention provides novel cyclic diamino compounds that are useful as factor Xa inhibitors or pharmaceutically acceptable salts or prodrugs thereof.

The present invention also provides processes and intermediates for making the compounds of the present invention or pharmaceutically acceptable salt or prodrug forms thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel compounds and derivatives thereof for use in therapy.

The present invention provides the use of novel compounds for the manufacture of a medicament for the treatment of a thromboembolic disorder.

These and other provisions, which will become apparent during the following detailed description, have been achieved by the inventors' discovery that the compounds as defined below, or pharmaceutically acceptable salt or prodrug forms thereof, are effective factor Xa inhibitors.

DETAILED DESCRIPTION OF PREFERRED EMBODIMENTS

In a first embodiment, the present invention provides a novel compound, wherein the compound is selected from:

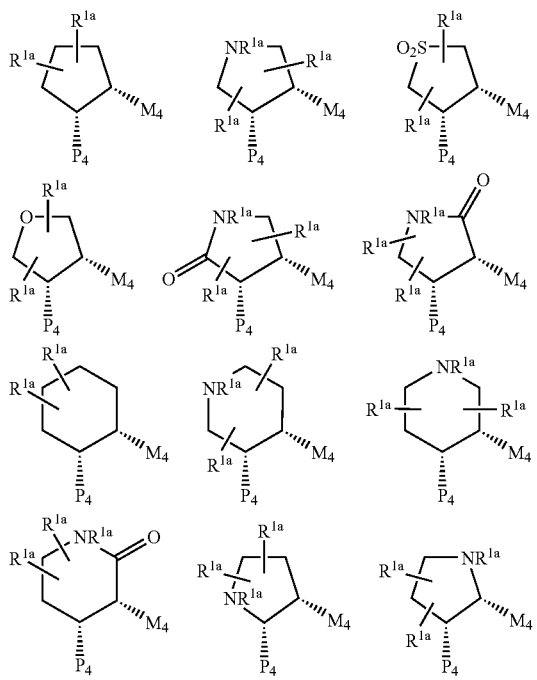

-continued
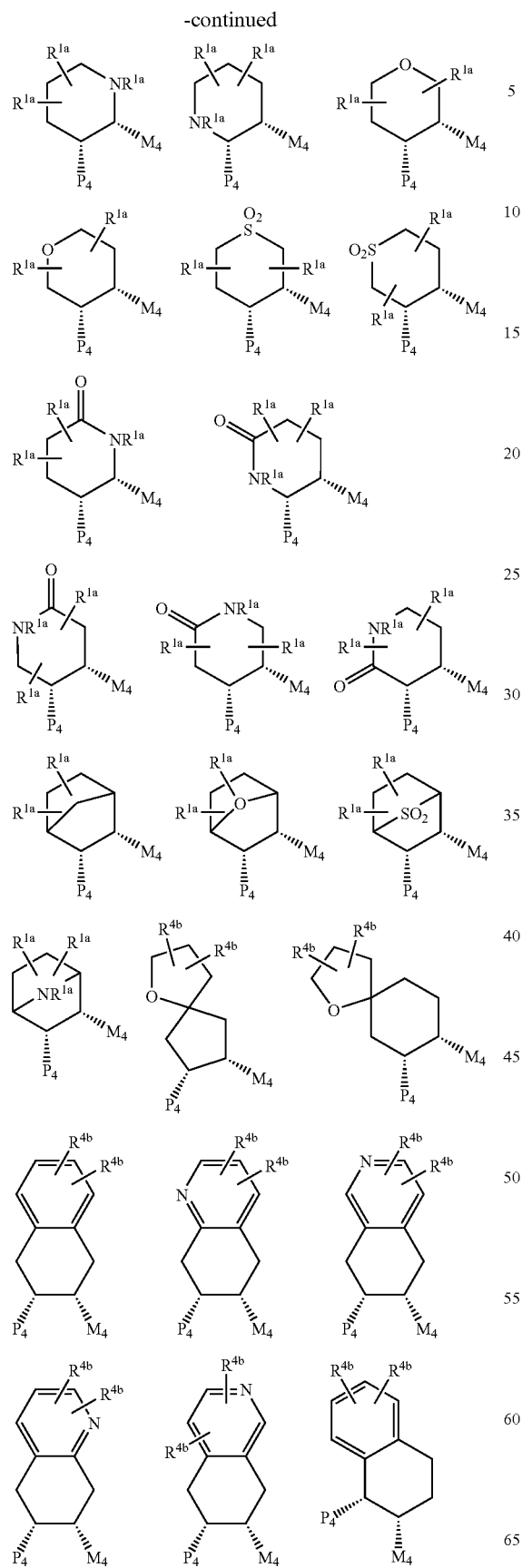
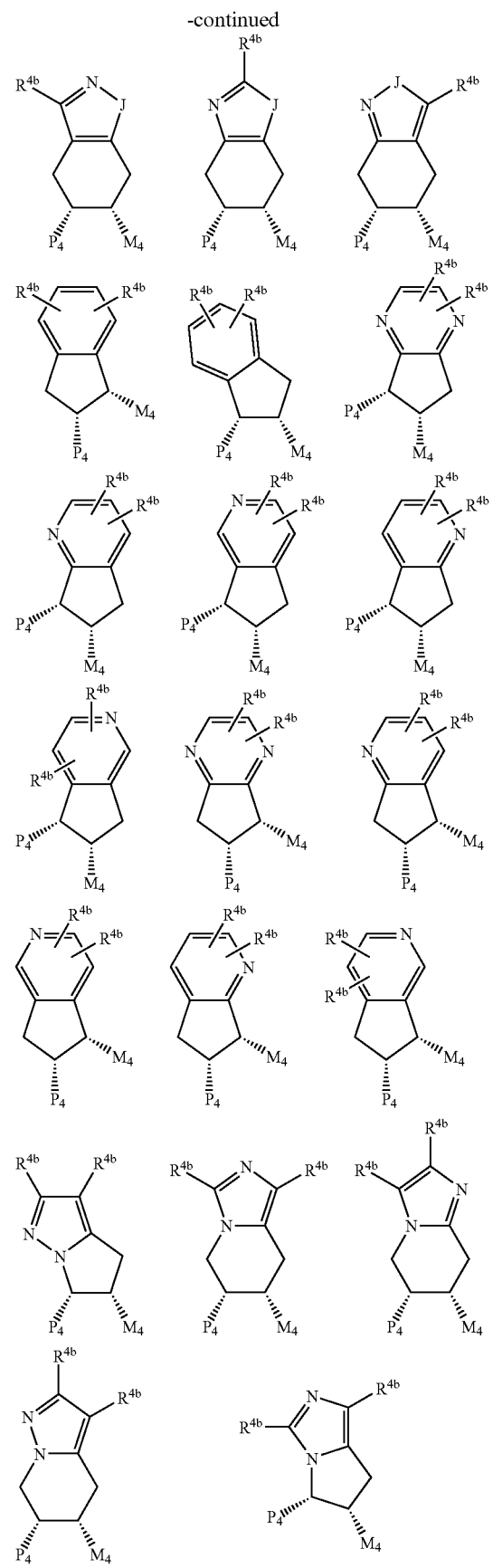

-continued

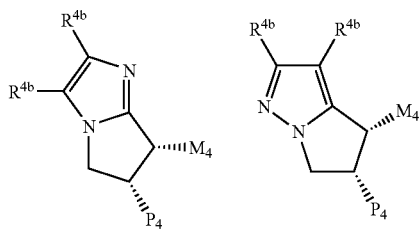
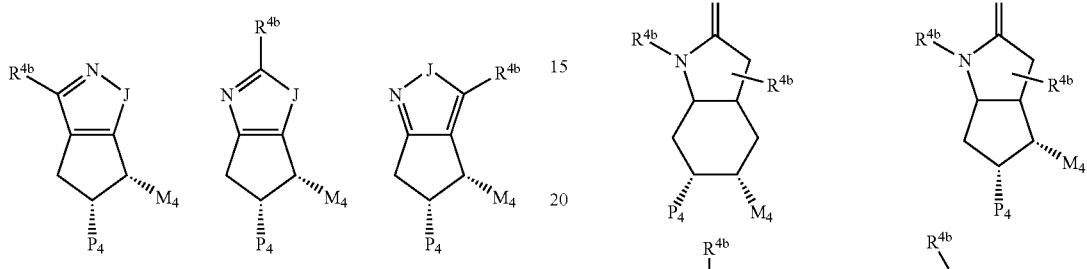
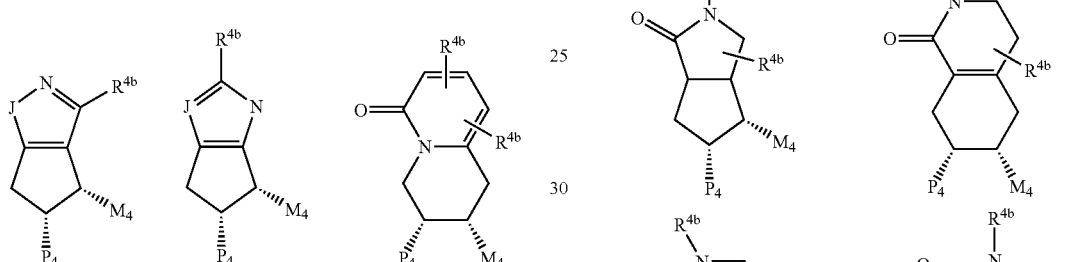
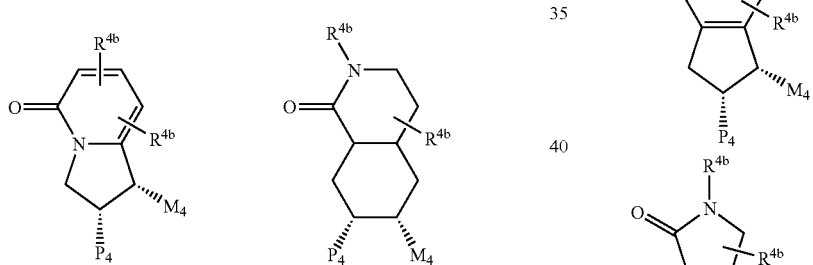
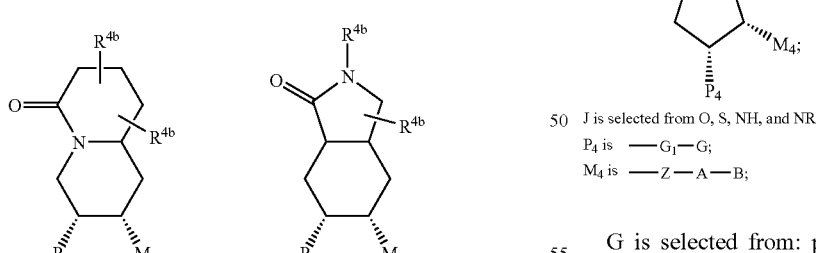
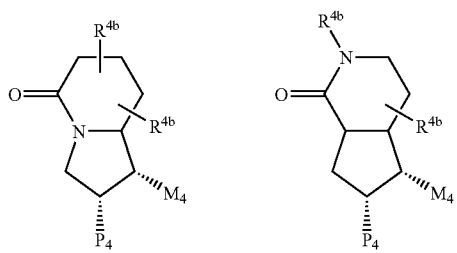

J is selected from O, S, NH, and NR$^{1a}$;
P$_4$ is —G$_1$—G;
M$_4$ is —Z—A—B;

G is selected from: phenyl; 4-ethyl-phenyl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonyl-phenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 2-methoxy-pyrid-5-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; 3-fluoro-4-chloro-phenyl; 3-methyl-4-chloro-phenyl; 3-fluoro-4-methyl-phenyl; 3;4-dimethyl-phenyl; 3-chloro-4-fluoro-phenyl; 3-methyl-4-fluoro-phenyl; 4-methylsulfanyl-phenyl;

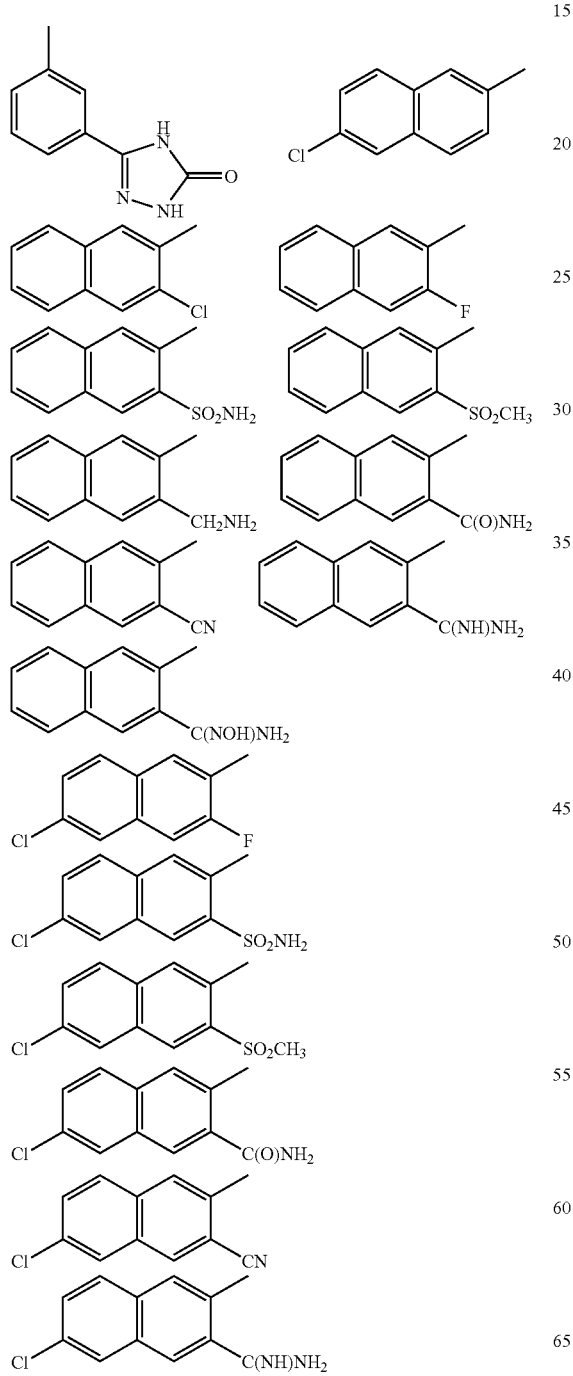
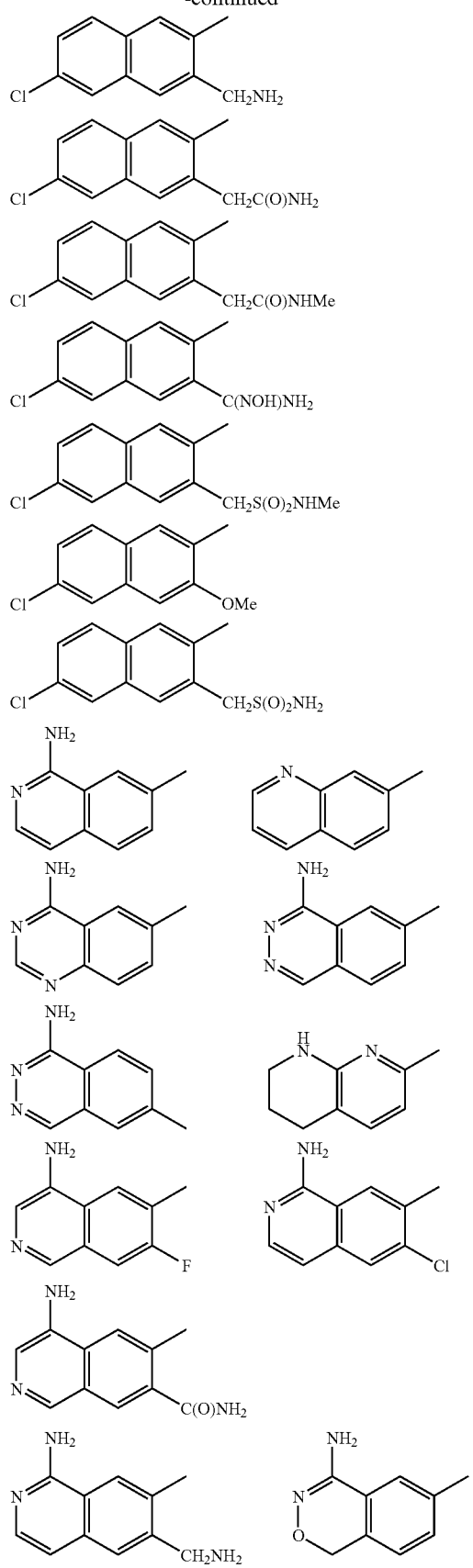

-continued
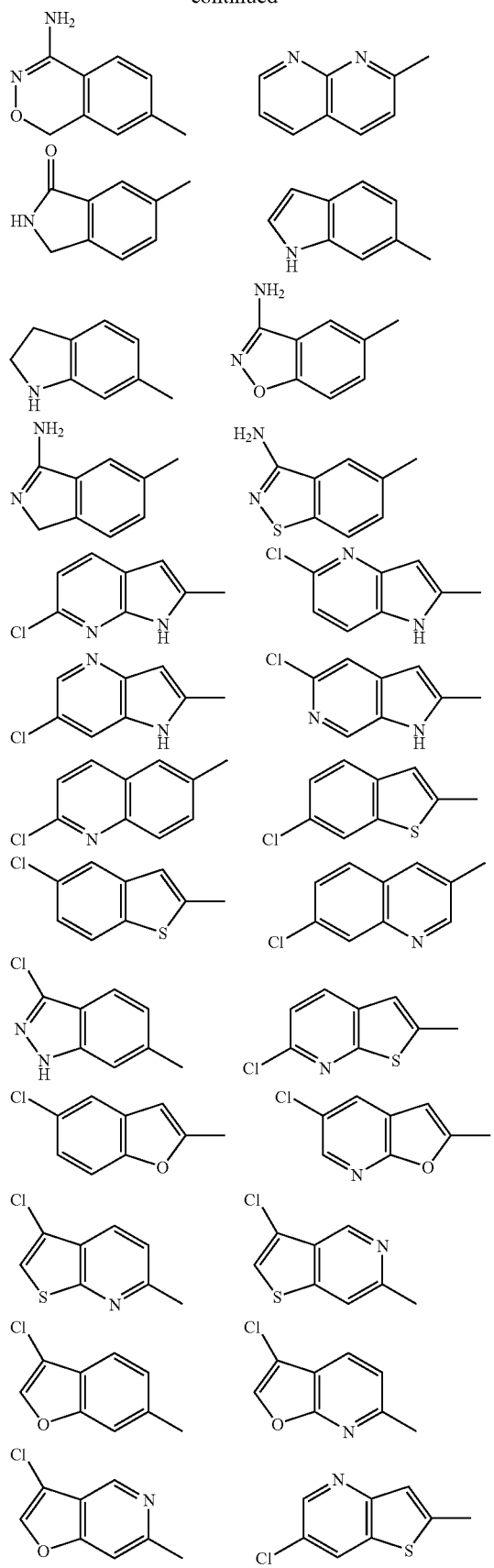
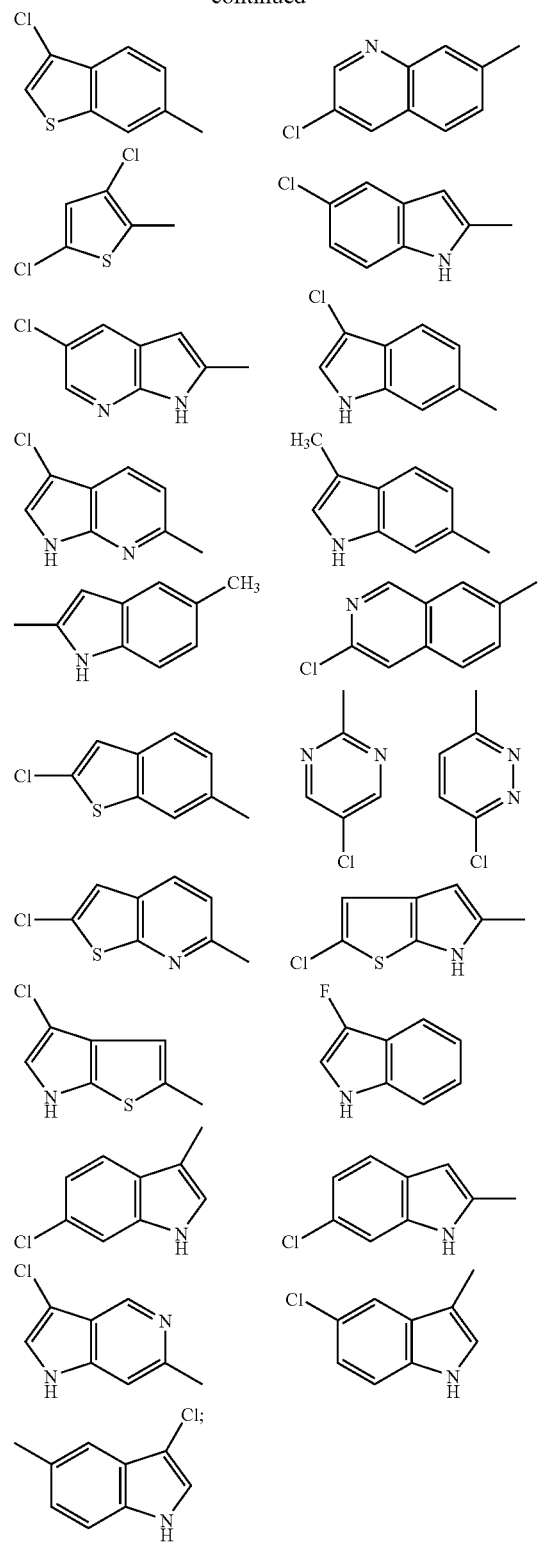
A is selected from the group: cyclohexyl, indolinyl, piperidinyl, 2-thienyl, 3-thienyl, 3-F-thien-2-yl, 3-Cl-thien-2-yl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is selected from isopropyl, cyclopropyl, cyclobutyl, cyclopentyl, cyclohexyl, tetrahydropyranyl, 1-methyl-piperidinyl, pyridyl, 4,5-dihydro-2-imdazolyl, 1,1-dimethyl-2-carboxamidine, 1,1-diethyl-2-carboxamidine, 1-ethyl-1-methyl-2-carboxamidine, 2-pyrrolidin-1-yl-methyleneamine, 2-piperidin-1-yl-methyleneamine, 2-morpholin-4-yl-methyleneamine, 1,4,5,6-tetrahydro-2-pyrimidinyl, [1,4]diazepanyl, phenyl, pyrrolidinyl, N-pyrrolidino-carbonyl, morpholinyl, N-morpholino-carbonyl, 1,2,3-triazolyl, imidazolyl, and benzimidazolyl, and is substituted with 0–1 $R^{4a}$;

provided that when G is chloro-indolyl, then B is other than pyridyl;

$G_1$ is selected from $CH_2C(O)$, $NHCH_2$, $CH_2NH$, $NHC(O)$, $C(O)NH$, $NHC(O)NH$, $NHC(O)C(O)NH$, $NHSO_2$, $CH_2SO$, and $CH_2SO_2$, wherein the left side of $G_1$ is attached to ring M, provided that $G_1$ does not form a N—S, $NCH_2N$, $NCH_2O$, or $NCH_2S$ bond with either group to which it is attached;

Z is selected from $CH_2C(O)$, $NHCH_2$, $NHC(O)$, $C(O)NH$, $NHC(O)NH$, $NHC(O)C(O)NH$, $NHSO_2$, $CH_2SO$, and —$CH_2SO_2$—, wherein the left side of Z is attached to ring M, provided that Z does not form a N—S, $NCH_2N$, $NCH_2O$, or $NCH_2S$ bond with either group to which it is attached;

$R^{1a}$ is selected from H, $CH_3$, $CH_2CH_3$, $CH_2CH_2CH_3$, $OCH_3$, $CH_2OH$, $C(CH_3)_2OH$, $CH_2OCH_3$, $CH_2CH_2OCH_3$, $NH_2$, $CH_2NH_2$, $NHCH_3$, $CH_2NHCH_3$, $N(CH_3)_2$, $CH_2N(CH_3)_2$, $CO_2H$, $CH_2CO_2H$, $CH_2CH_2CO_2H$, $CH_2CH_2CO_2CH_2CH_3$, $COCH_3$, $COCH_2C(CH_3)_3$, $COCF_3$, $CO_2CH_3$, $CO_2CH_2CH_3$, $CO_2CH(CH_3)_2$, $CO_2C(CH_3)_3$, $CH_2CO_2CH_3$, $CH_2CH_2CO_2CH_2CH_3$, $S(O)_2CH_3$, $CH_2S(O)_2CH_3$, $C(O)NH_2$, $CONH(CH_3)$, $CONH(CH_2CH_3)$, $CONHC(CH_3)_3$, $CON(CH_3)_2$, $CON(CH_3)(CH_2CH_3)$, $CON(CH_3)CH(CH_3)_2$, $CH_2C(O)NH_2$, $CH_2CON(CH_3)_2$, $CSN(CH_3)_2$, $SO_2NH_2$, $CH_2SO_2NH_2$, $NHSO_2CH_3$, and $CH_2NHSO_2CH_3$;

alternatively, $R^{1a}$ is selected from:

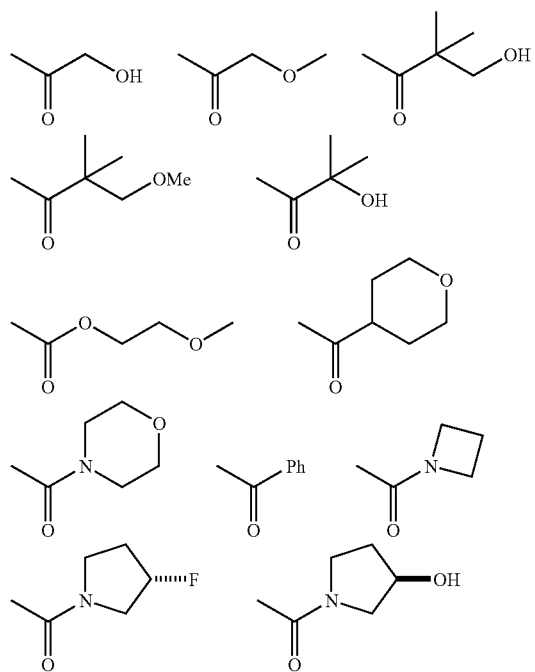

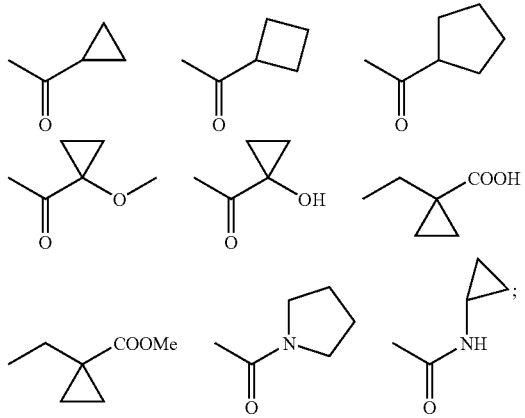

$R^2$, at each occurrence, is selected from H, $C_{1-3}$ alkyl substituted with 0–1 $R^{4b}$, $C_{3-6}$cycloalkyl substituted with 0–1 $R^{4b}$, $CH_2$—$C_{3-6}$cycloalkyl substituted with 0–1 $R^{4b}$, phenyl substituted with 0–1 $R^{4b}$, benzyl substituted with 0–1 $R^{4b}$, and 5 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from H, $CH_3$, and $CH_2CH_3$;

alternatively, $NR^2R^{2a}$ forms a 5 or 6 membered saturated, partially saturated or unsaturated ring substituted with 0–1 $R^{4b}$ and consisting of: carbon atoms, the N of $NR^2R^{2a}$, and 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{4a}$ is selected from $C_{1-4}$alkyl, $CF_3$, $OR^2$, $CH_2OR^2$, $(CH_2)_2\ OR^2$, $NR^2R^{2a}$, $CH_2NR^2R^{2a}$, $(CH_2)_2NR^2R^{2a}$, $S(O)_p R^5$, $SO_2NR^2R^{2a}$, and 1-$CF_3$-tetrazol-2-yl;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$; and p, at each occurrence, is selected from 0, 1, and 2.

In a second embodiment, the present invention provides a novel compound, wherein the compound is selected from:

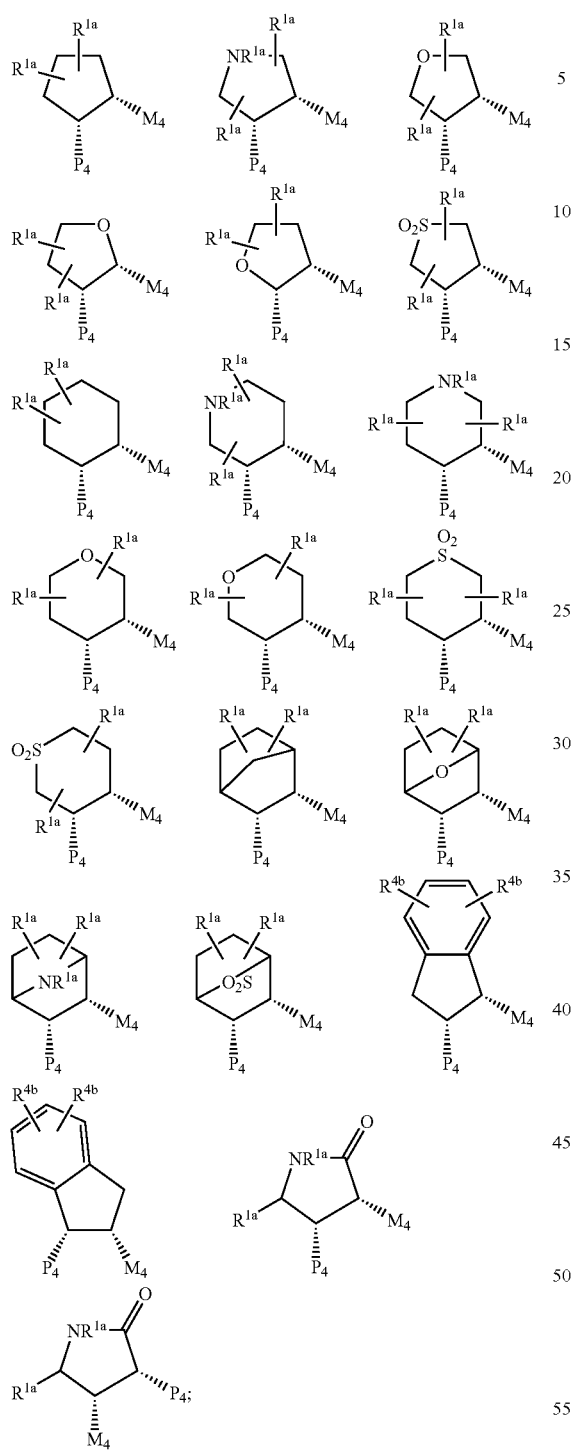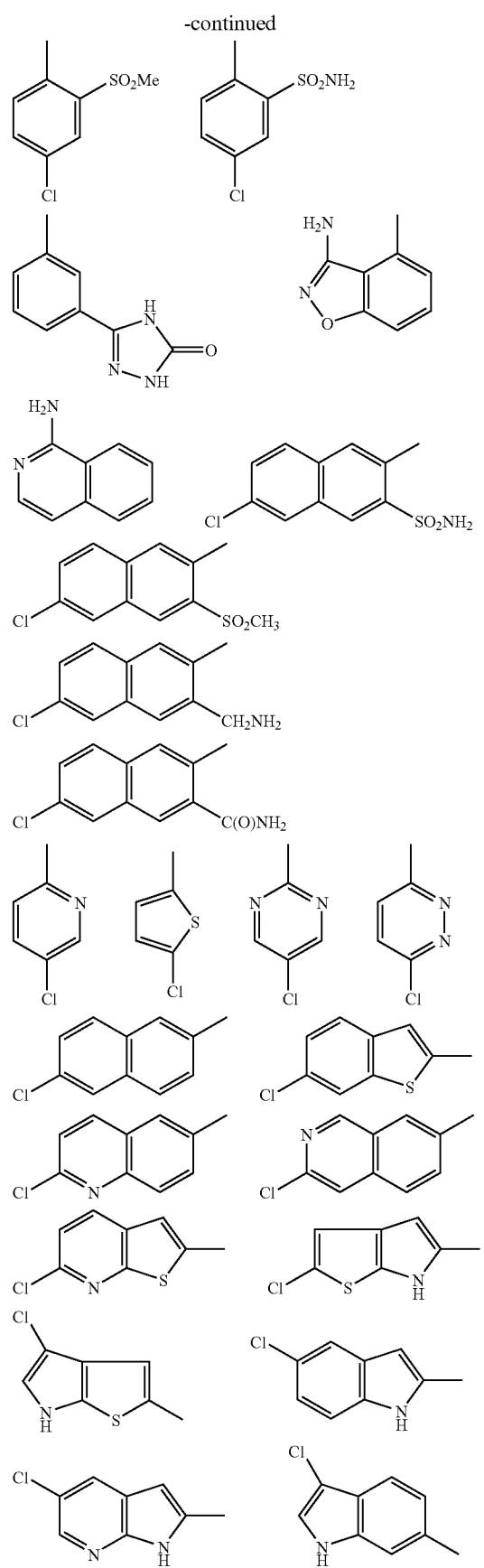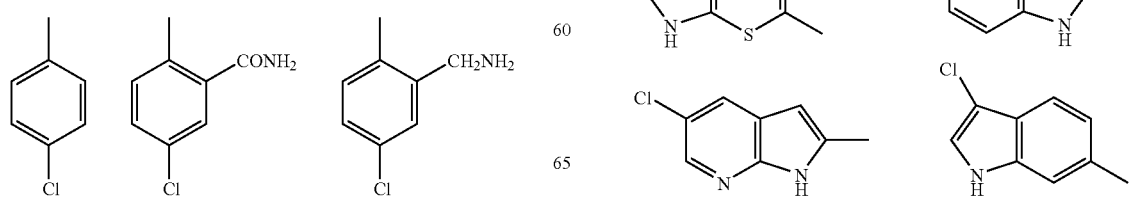

-continued

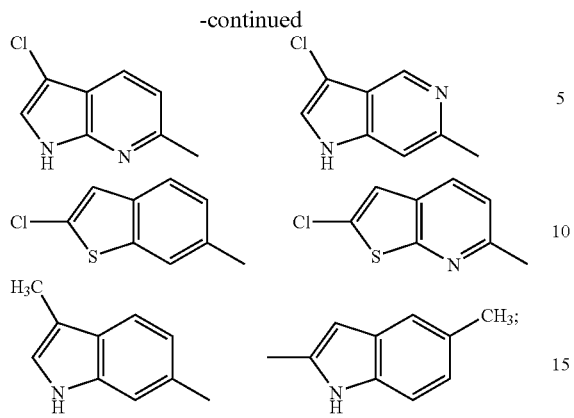

G₁ is NHC(O) or C(O)NH, wherein the left side of G₁ is attached to ring M;

Z is NHC(O) or C(O)NH, wherein the left side of Z is attached to ring M;

A is selected from the group: 4-piperidinyl, 2-thienyl, 2-Cl-thien-2-yl, and 2-F-thienyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and B is selected from the group: isopropyl, cyclopropyl, cyclohexyl, tetrahydropyranyl, 1-methyl-piperidinyl, N-morpolinyl, 1-methyl-4,5-dihydro-2-imdazolyl, 1,1-dimethyl-2-carboxamidine, 2-pyrrolidin-1-yl-methyleneamine, 2-piperidin-1-yl-methyleneamine, 2-morpholin-4-yl-methyleneamine, 1-methyl-1,4,5,6-tetrahydro-pyrimidin-2-yl, 4-methyl-[1,4]diazepane-1-yl, 2-(aminosulfonyl)phenyl, 2-(methylaminosulfonyl)phenyl, N-pyrrolidino-carbonyl, 2-(methylsulfonyl)phenyl, 2-(N,N-dimethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, 2-(N-(3-hydroxypyrrolidinyl)methyl)phenyl, 1-methylpiperidine-4-yl, 2-(N-(cyclopropylmethyl)aminomethyl))-1-imidazolyl, 2-(N-(cyclobutyl)aminomethyl))-1-imidazolyl, 2-(N-(cyclopentyl)aminomethyl))-1-imidazolyl, 2-(N-(4-hydroxypiperidinyl)methyl))-1-imidazolyl, 2-(N-(3-hydroxypyrrolidinyl)methyl))-1-imidazolyl, and 2-(N-(2-ethanol)aminomethyl))-1-imidazolyl.

In a third embodiment, the present invention provides a novel compound, wherein the compound is selected from:

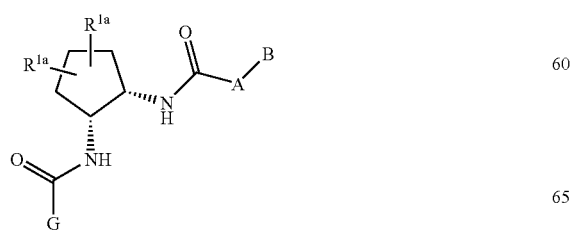

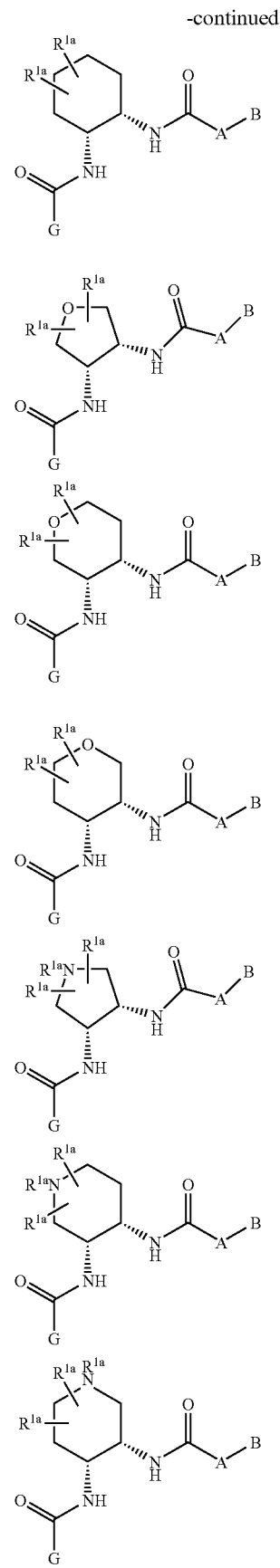

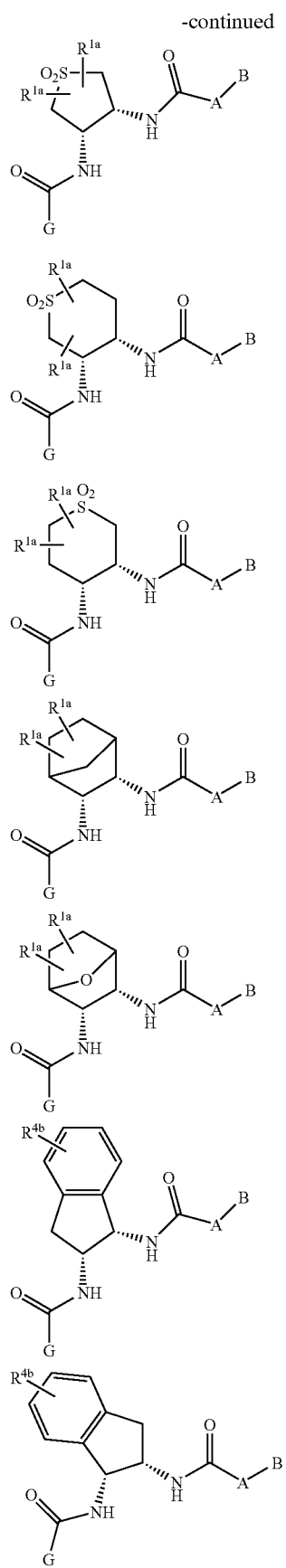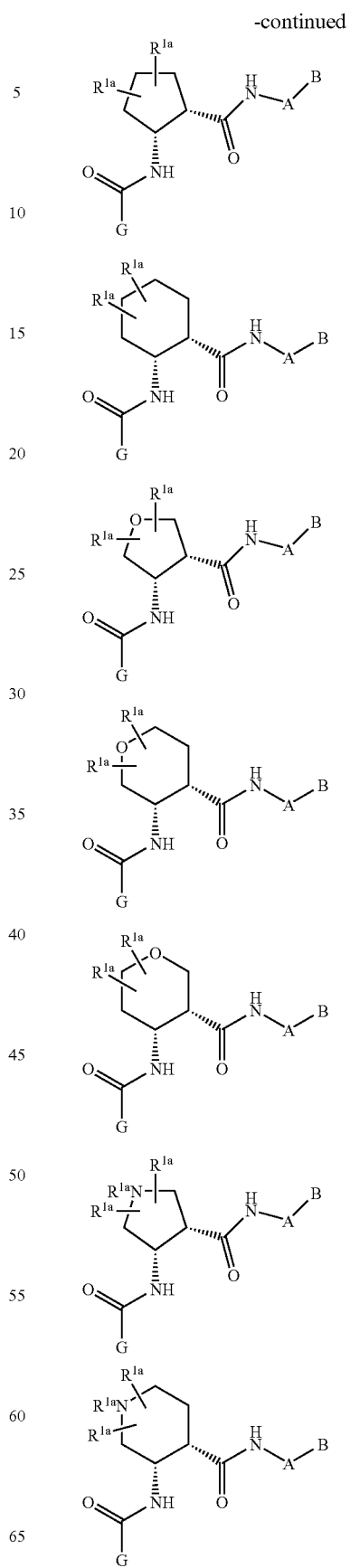

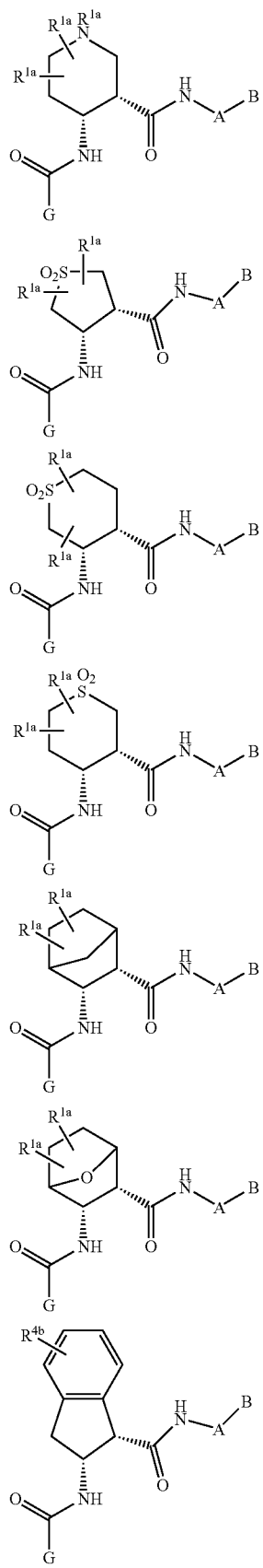
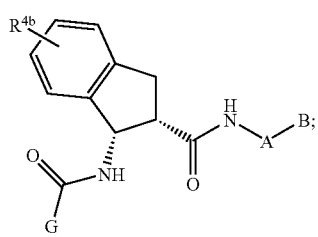
G is selected from:
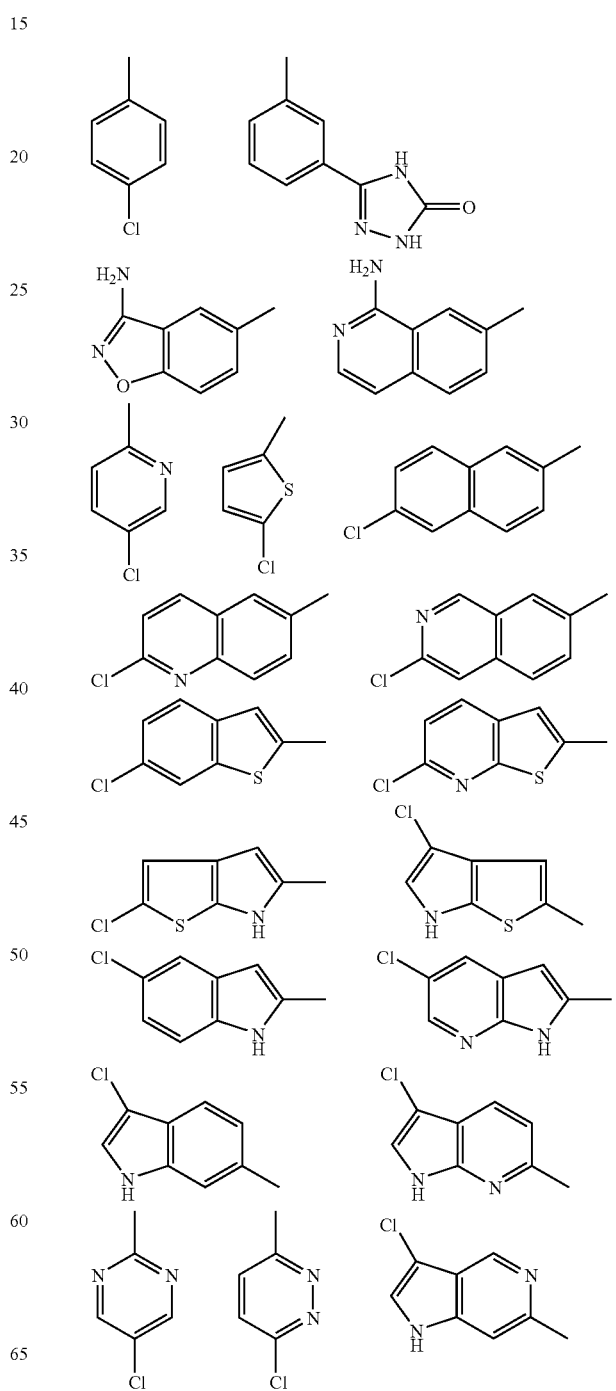

-continued
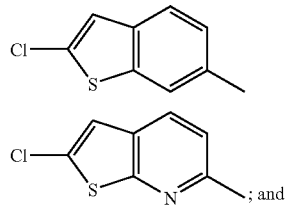; and
A-B is selected from:
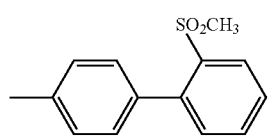
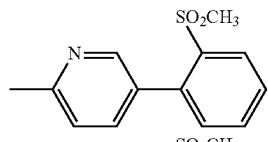
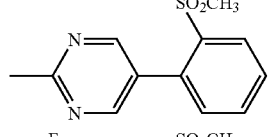
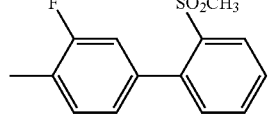
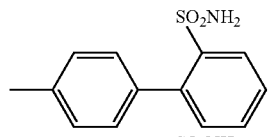
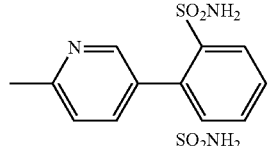
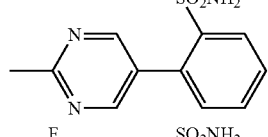
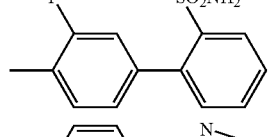
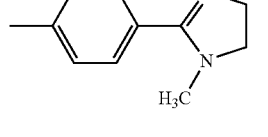
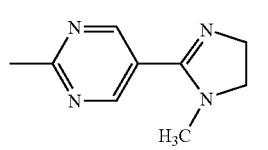
-continued
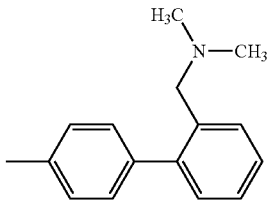
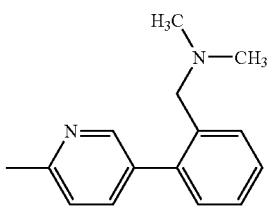
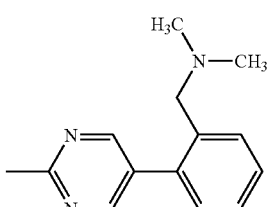
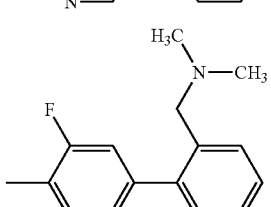
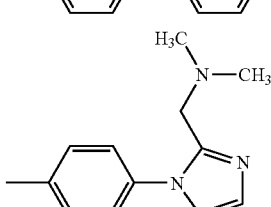
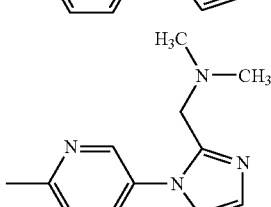
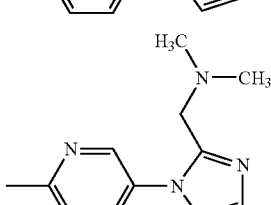
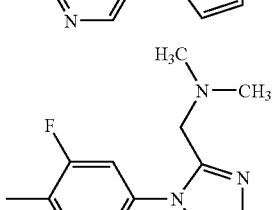

-continued

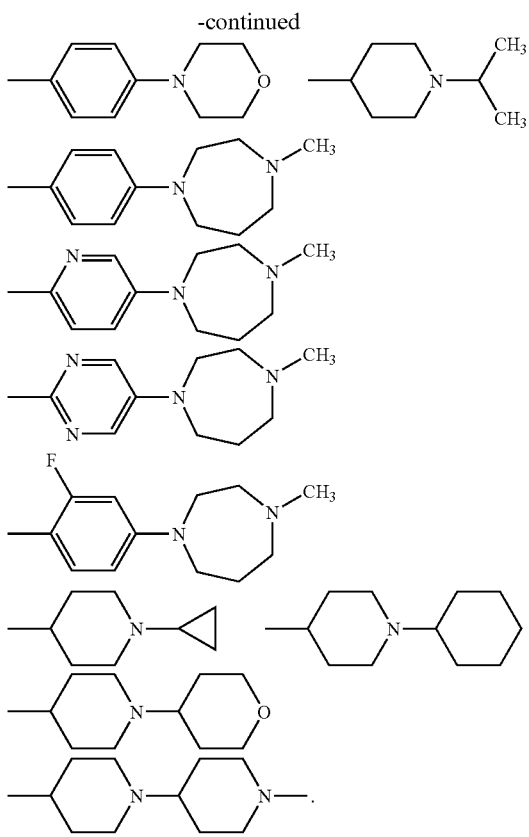

In a fourth embodiment, the present invention provides a novel compound, wherein the compound is selected from (1R, 2S)-3-Chloro-1H-indole-6-carboxylic acid {2-[4-(2-dimethylaminomethyl-imidazol-1-yl)-benzoylamino]-cyclopentyl}-amide;

(1R, 2S)-5-Chloro-thiophene-2-carboxylic acid {2-[4-(2-dimethylaminomethylimidazol-1-yl)-benzoylamino]-cyclopentyl}-amide;

(1R, 2S)-5-Chloro-thiophene-2-carboxylic acid {2-[4-(2-dimethylaminomethyl-imidazol-1-yl)-benzoylamino]-cyclohexyl}-amide;

(1R, 2S)-3-Chloro-1H-indole-6-carboxylic acid {2-[4-(2-dimethylaminomethyl-imidazol-1-yl)-benzoylamino]-cyclohexyl}-amide;

(1R, 2S)-3-Chloro-1H-indole-6-carboxylic acid {2-[(1-isopropyl-piperidine-4-carbonyl)-amino]-cyclohexyl}-amide;

(1R, 2S)-3-Chloro-1H-indole-6-carboxylic acid [2-(4-morpholin-4-yl-benzoylamino)-cyclopentyl]-amide;

(1R, 2S)-3-Chloro-1H-indole-6-carboxylic acid [2-(4-morpholin-4-yl-benzoylamino)-cyclohexyl]-amide; and (1R, 2S)-3-Chloro-1H-indole-6-carboxylic acid {2-[4-(2-dimethylaminomethyl-imidazol-1-yl)-benzoylamino]-indan-1-yl}-amide;

or a pharmaceutically acceptable salt form thereof.

In a fifth embodiment, the present invention provides a novel compound, wherein the compound is selected from Examples 1–1168 of Table 1, or a pharmaceutically acceptable salt form thereof.

In another embodiment, the present invention provides a novel process for making a compound of the present invention or a pharmaceutically acceptable salt form thereof.

In another embodiment, the present invention provides a novel intermediate for making a compound of the present invention or a pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides a compound of the present invention for use in therapy.

In another embodiment, the present invention provides the use of a compound of the present invention as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$alkyl, is intended to include $C_1$, $C_2$, $C_3$, $C_4$, $C_5$, and $C_6$alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —C$_v$F$_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C$_{1-6}$alkoxy, is intended to include C$_1$, C$_2$, C$_3$, C$_4$, C$_5$, and C$_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. C$_{3-7}$cycloalkyl is intended to include C$_3$, C$_4$, C$_5$, C$_6$, and C$_7$cycloalkyl groups. Alkenyl" is intended to include hydrocarbon chains of either straight or branched configuration and one or more unsaturated carbon-carbon bonds that may occur in any stable point along the chain, such as ethenyl and propenyl. C$_{2-6}$alkenyl is intended to include C$_2$, C$_3$, C$_4$, C$_5$, and C$_6$ alkenyl groups. "Alkynyl" is intended to include hydrocarbon chains of either straight or branched configuration and one or more triple carbon-carbon bonds that may occur in any stable point along the chain, such as ethynyl and propynyl. C$_{2-6}$Alkynyl is intended to include C$_2$, C$_3$, C$_4$, C$_5$, and C$_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyrindinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

A non-aromatic carbocycle or non-aromatic heterocycle, as used herein, means that the carbocyclic or heterocyclic ring is not aromatic. If the carbocycle or heterocycle is bicyclic or tricyclic, then at least one of the rings in the bicycle or tricycle is not aromatic. In addition, if the carbocycle or heterocycle is bicyclic or tricyclic, then the P$_4$ and M$_4$ substituents of ring M are attached to the non-aromatic ring portion of ring M. For example, 2-P$_4$-3-M$_4$-2,3-dihydrobenzofuran would be a non-aromatic heterocycle in accordance with the present definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991). All references cited herein are hereby incorporated in their entirety herein by reference.

Compounds of the present invention (Scheme 1) can be prepared as outlined in Schemes 2–7 and via standard methods known to those skilled in the art.

Scheme 1

The compounds of the present invention wherein A-B is a substituted biaryl or a substituted aryl-heteroaryl can be prepared as shown in Scheme 2. A properly protected 4-bromobenzene can be used as the starting material. It can be reacted with a boronic acid under Suzuki coupling condition to afford the protected A-B intermediate 1. Deprotection of 1 can produce A-B structure 2, which can be coupled with 3 using standard coupling conditions to afford compounds of the present invention.

Scheme 2

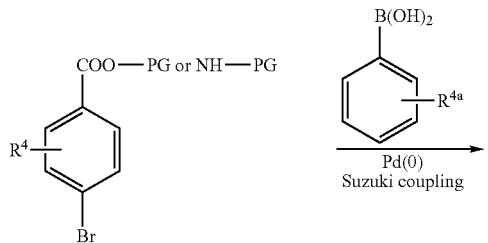

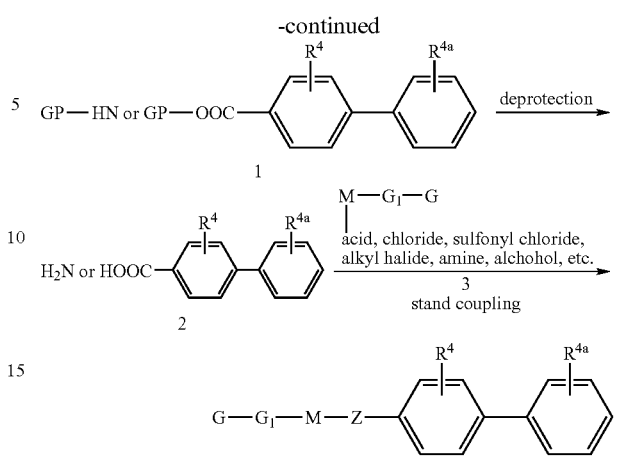

Other compounds of the present invention wherein B is an imidazole derivative can be prepared as shown in Scheme 3, using Ullman or Buchwald modified Ullman reaction conditions (*J. Am. Chem. Soc.* 2001, 123, 7727). Using CuI and 1,2-cyclohexyldiamine or 1,10-phenanthroline, the iodo intermediate 4 can afford the intermediate 5, which can undergo either alkylation or reductive amination to provide the A-B intermediate 6. The compounds of the present invention can then be prepared from 6 analogous to the procedure described in Scheme 2.

Scheme 3

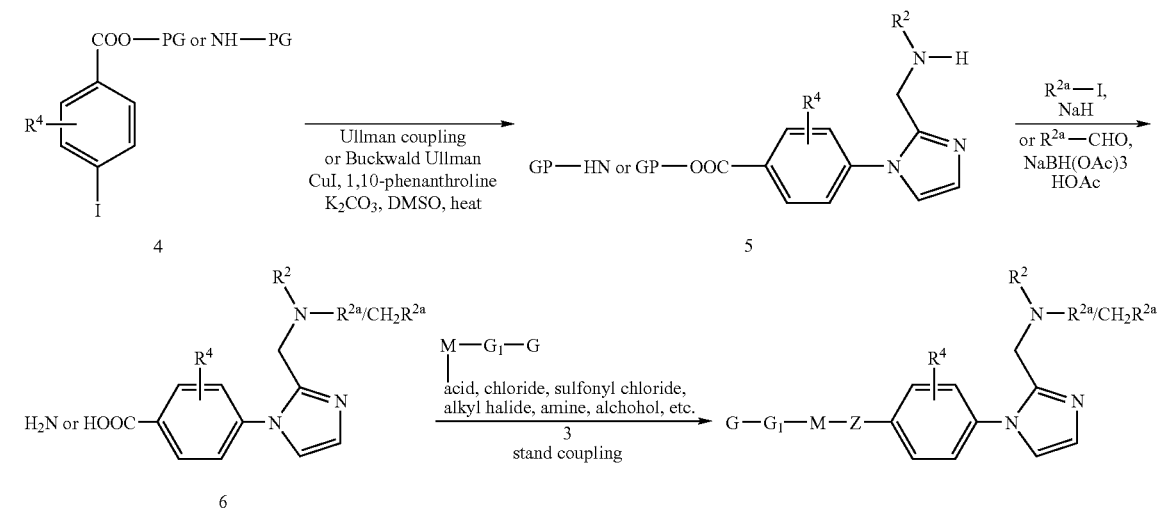

Other compounds of the present invention wherein B is an amidino derivative can be prepared using properly protected aryl nitrites as the starting material as illustrated in Scheme 4. The pinner reaction (MeOH, HCl), followed by displacement with a diamine can provide A-B precursor 7, which can be coupled with 3 using standard coupling conditions to provide compounds of the present invention. Alternatively, iodination will provide the desired para-substituted compound 8, which can in turn be transformed to the amine 9 via Buchwald palladium-catalyzed amination (*Tetrahedron Lett.*

1997, 38, 6367–6370) and acid 10 via paladium-catalyzed carboxylation (CO, Pd(OAc)$_2$, dppf). Additional Z-linkers can be synthesized by chemical manipulation of the amino and carboxylic acid functionalities in 9 and 10. Compound 10 can be homologated via the Arndt-Eistert methodology to afford other A-B intermediates 11. Alternatively, the acid functionality in 10 can be reduced to the alcohol that in turn can be converted to a variety of A-B intermediates 11 by procedures known to those skilled in the art. Further elaboration of these intermediates using the methods described above and those known in the art should provide compounds of the present invention.

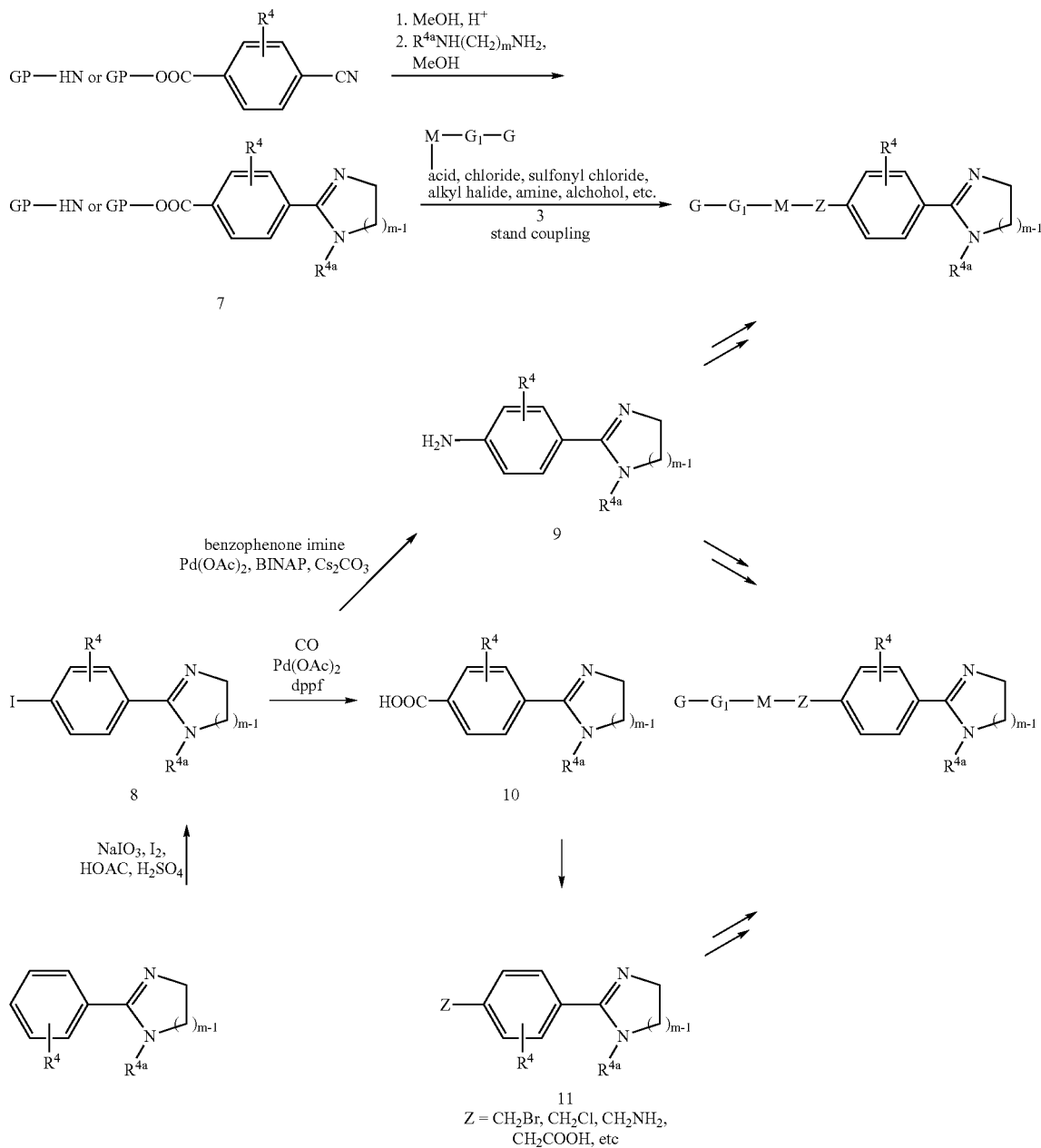

Scheme 4

Other compounds of the present invention wherein B is a [1,4]diazepane derivative can be prepared using the procedures shown in Scheme 5. Aromatic nucleophilic displacement or C—N bond formation using Pd(0) chemistry will provide A-B intermediate 12. Further elaboration of 12 using the methods described above and by those known in the art should provide compounds of the present invention.

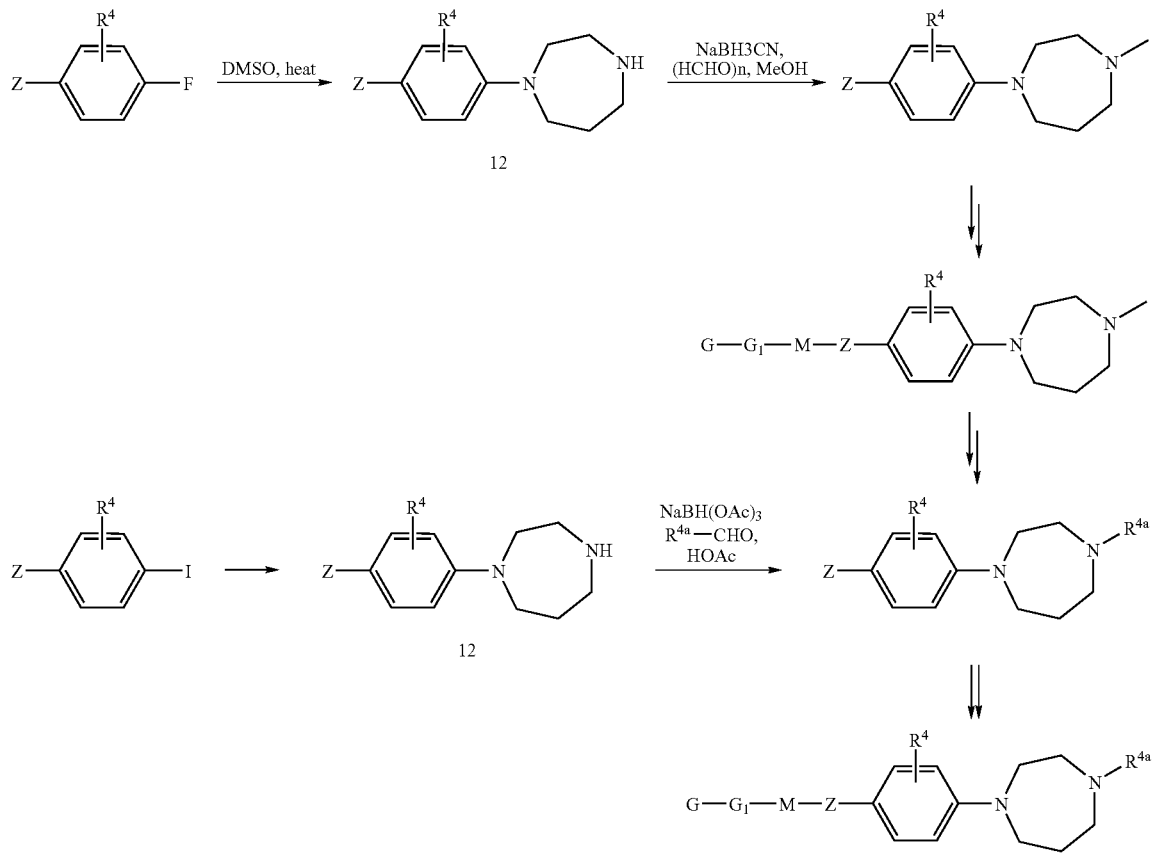

Compounds of formula I wherein B is X—Y, X is a 1–3 atom linker, and Y is a heteroaryl or aryl derivative can also be prepared as described previously in WO 98/06694, U.S. Pat. No. 6,057,342, WO 98/28282, U.S. Pat. No. 6,187,797, WO 98/28269, U.S. Pat. No. 6,020,357, WO 98/57934, and U.S. Pat. No. 6,426,346 and by those skilled in the art.

Aminopyridyl and aminopyrimidyl A-B analogs (see Scheme 6) can be prepared using routes similar to those of Schemes 2–5 and also by those skilled in the art. These intermediates can then be manipulated to compounds of the present invention via procedures previously described.

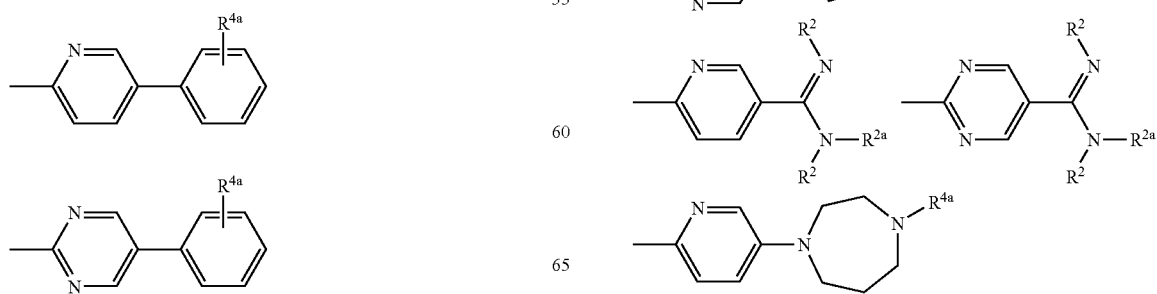

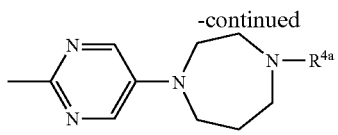

Schemes 2–6 describe how to make the A-B moieties of the present invention and how to couple them to prepare compounds of the present invention.

The compounds of this invention and the intermediates described above wherein the B group contains an oxidizable group can be oxidized, e.g., N to N-oxide.

For compounds wherein G is a ring substituted with a basic moiety, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 6,191,159, WO98/57951, WO99/32454 WO00/059902, WO01/32628, WO00/39131, WO02/00651, WO02/102380, WO02/94197, U.S. Ser. No. 10/104,467, and U.S. Ser. No. 10/105,477 for starting materials and intermediates to form the present G-G-1-M-Z, G-G-1-M-Z, G-G-1-M-Z-A, and/or G-G-1-M-Z-A groups to which the present B and/or A-B groups can be coupled. For compounds wherein G is a ring substituted with a non-basic group, one of ordinary skill in the art can look to U.S. Pat. No. 5,998,424, WO00/39131, WO00/059902, WO01/32628, WO02/00651, WO02/102380, WO02/94197, U.S. Ser. No. 10/104,467, and U.S. Ser. No. 10/105,477 for starting materials and intermediates to form the present G-G-1-M-Z, G-G-1-M-Z, G-G-1-M-Z-A, and/or G-G-1-M-Z-A groups to which the present B and/or A-B groups can be coupled. For compounds wherein G is a bicyclic moiety, one of ordinary skill in the art can look to WO98/57951 WO00/039108, WO00/39131, WO02/00651, WO02/102380, WO02/94197, U.S. Ser. No. 10/104,467, and U.S. Ser. No. 10/105,477 for starting materials and intermediates to form the present G-G-1-M-Z, G-G-1-P-Z, G-G-1-M-Z-A, and/or G-G-1-M-Z-A groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed.

Compounds of the present invention wherein ring M is a non-aromatic carbocycle or heterocycle can be prepared by using the methods described previously and known to those skilled in the art. Scheme 7 illustrates some of the monocyclic/heterocyclic M intermediates that can be used to prepare compounds of the present invention ($R^z$ is the point of attachment for Z-A-B and can be a protecting group, a group modifiable to Z or Z-A, Z, Z-A, or A; $R^g$ is the point of attachment for G-1-G and can be a protecting group, a group modifiable to G-1 or G-1-G). These intermediates can be prepared using methods known to those of ordinary skill in the art.

Scheme 7

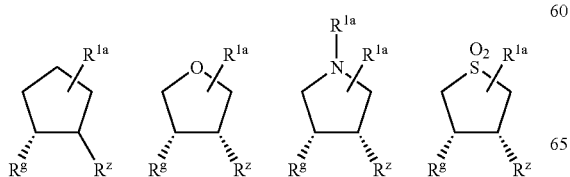

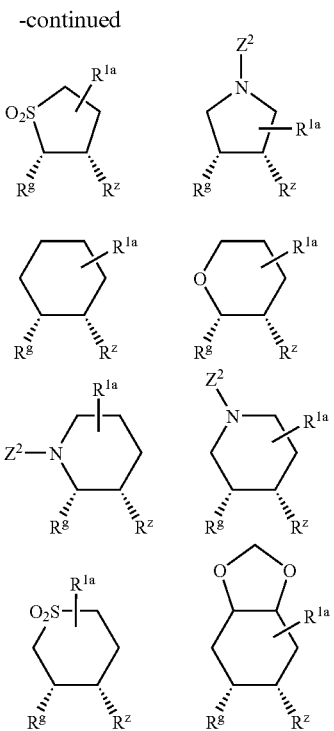

All of the following patents and publications are incorporated herein by reference. For compounds wherein ring M is a 5-, or 6-membered ring, one of ordinary skill in the art can look to the following for starting materials and intermediates to which the present B and/or A-B groups can be coupled: WO00/47207; WO98/16497; WO94/20062; WO01/28987; WO00/69855; WO02/60859; GB2210039; EP237829; *Bioorg. & Med. Chem. Let.* 1998, 8(5), 525–528; *Tetrahedron* 1997, 53(4), 1417–1438; *J. Het. Chem.* 1988, 25(3), 1035–6; and, *Tetrahedron: Asymmetry* 1997, 8(11), 1861–1867.

Scheme 8 describes general methods of converting the M rings shown in Scheme 7 to compounds of the present invention wherein linker $G_1$ can be —NHCO—, —NHCO-CONH—, —NHCOC(S)NH—, —NHC(S)CONH—, or —CONH—, and linker Z can be —NHCO— or —CONH—. As one of ordinary skill in the art recognizes, this method would be applicable to other non-aromatic rings not shown. Properly protected, enantiomerically pure cyclic amino acid cores can be obtained via the Davies' protocol (*J. Chem. Soc. Perkin Trans I,* 1994, 1411) or via reduction of enamines (*J. Org. Chem.* 1996, 61, 5557). The corresponding diamino compounds can be obtained via saponification of the ester of the cyclic amino acids followed by Curtius rearrangement. On the other hand, the cyclic diamines can be prepared via literature methods. (See, for example, *Tetrahedron: Assymmetry,* 1997, 8, 1861 and *Tetrahedron Lett.* 1998, 39, 6921).

Scheme 8

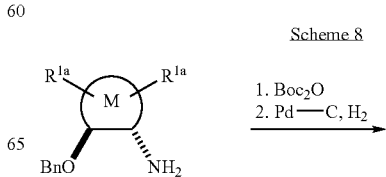

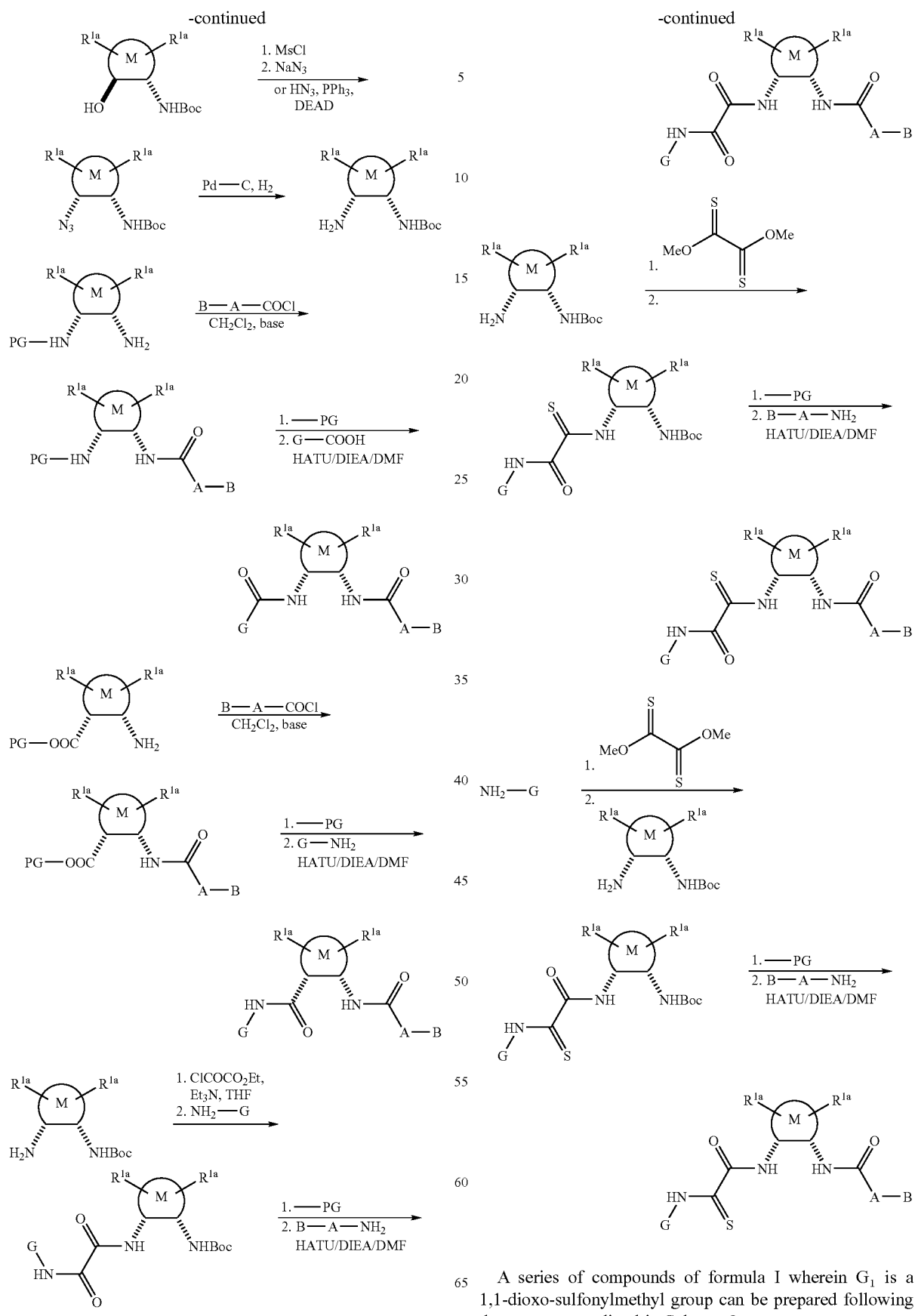
A series of compounds of formula I wherein $G_1$ is a 1,1-dioxo-sulfonylmethyl group can be prepared following the sequence outlined in Scheme 9.

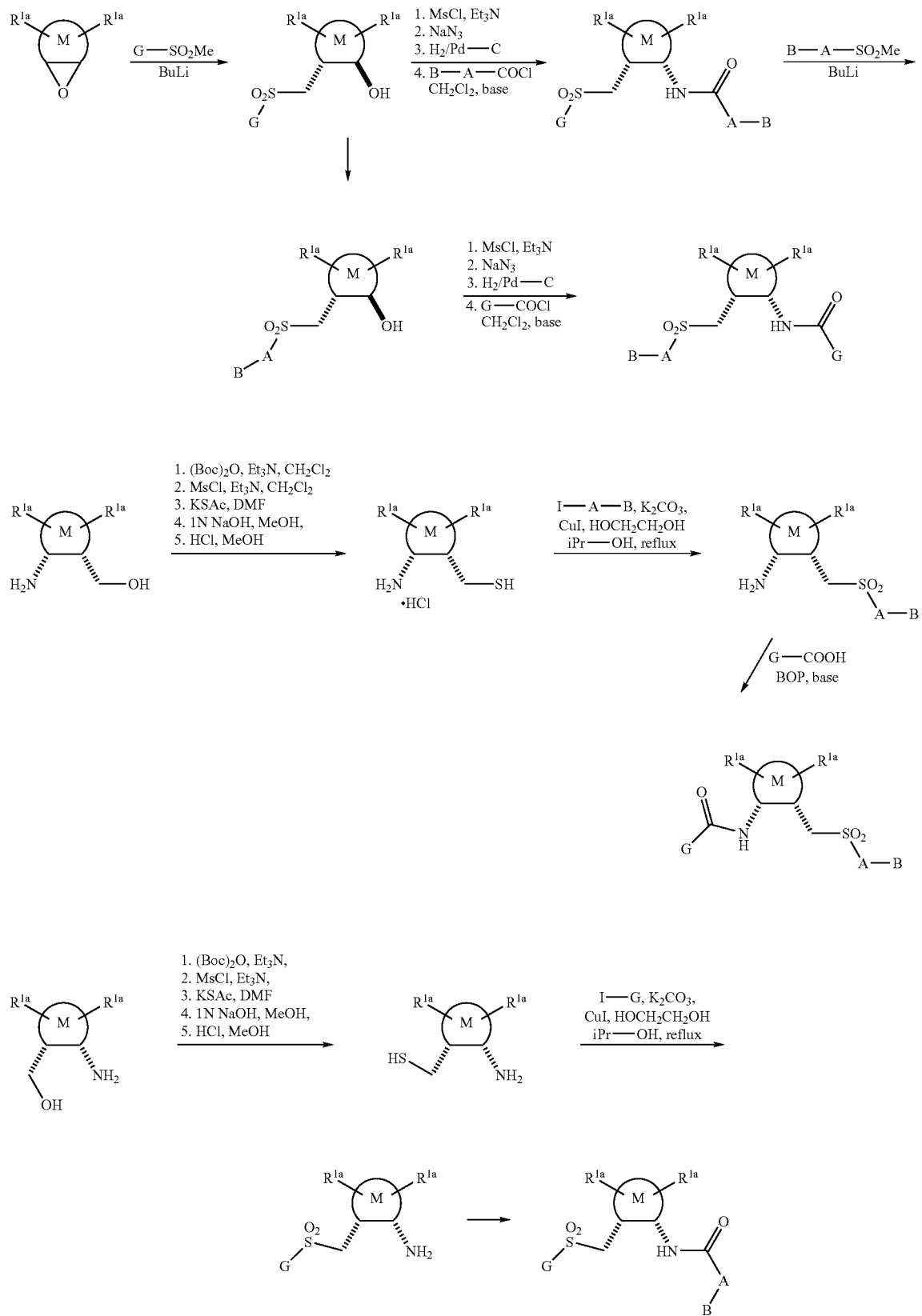

Scheme 10 illustrates numerous bicyclic M intermediates that can be used to prepare compounds of the present invention. These intermediates can be prepared using methods known to those of ordinary skill in the art and using similar methods described previously.
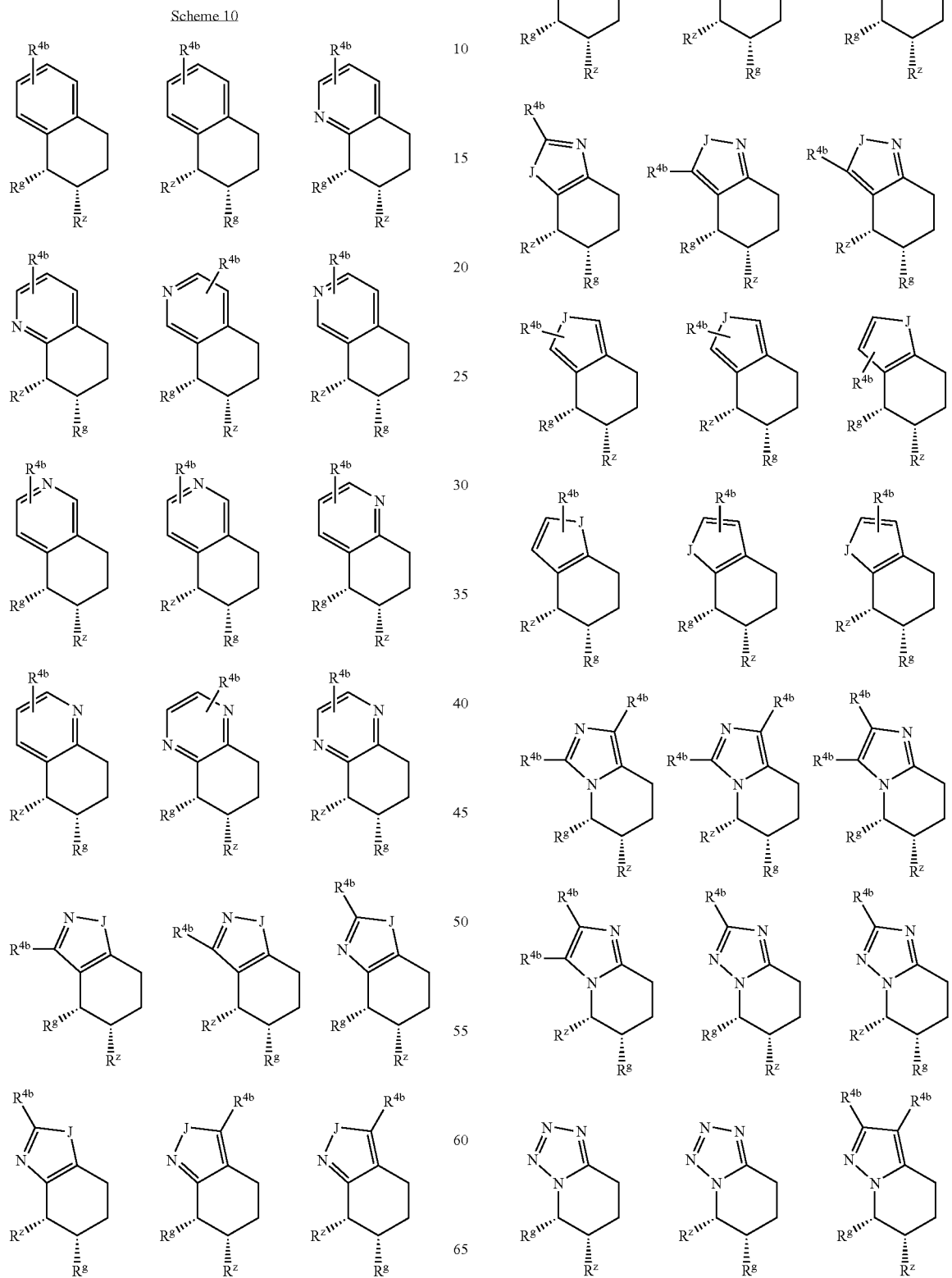

-continued

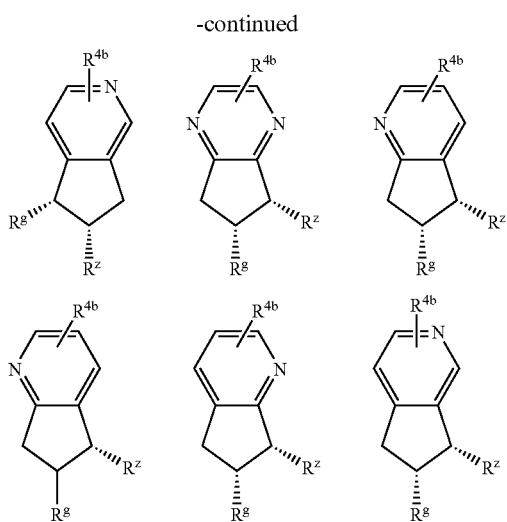

Scheme 11 illustrates the synthesis of benzofused M intermediates. The α- or β-amino acid derivatives 13 can undergo Friedel-Crafts reaction followed by reduction to afford fused ring intermediates 14. Replacement of the OH group with $NH_2$ group as described previously to afford 15, followed by standard coupling reactions will provide the compounds of the present invention. On the other hand, oxime formation of the ketone intermediate 16 followed by reduction with $NaBH_4$ can provide the amino alcohol intermediate 17, which can also be obtained via epoxidation of the olefin intermediate 18 and then nucleophilic displacement. Protection of the amino group in 17 followed by azide displacement of the mesylate and then reduction of the azide group will give the Boc protected diamino compound 19. Functional groups U and V can be acid chloride, carboxylic acid, sulfonyl chloride, etc. in U-G-1-G and V-A-B. The compounds of the present invention can be obtained from 18 using methods known to those of ordinary skill in the art and using methods similar to those described previously.

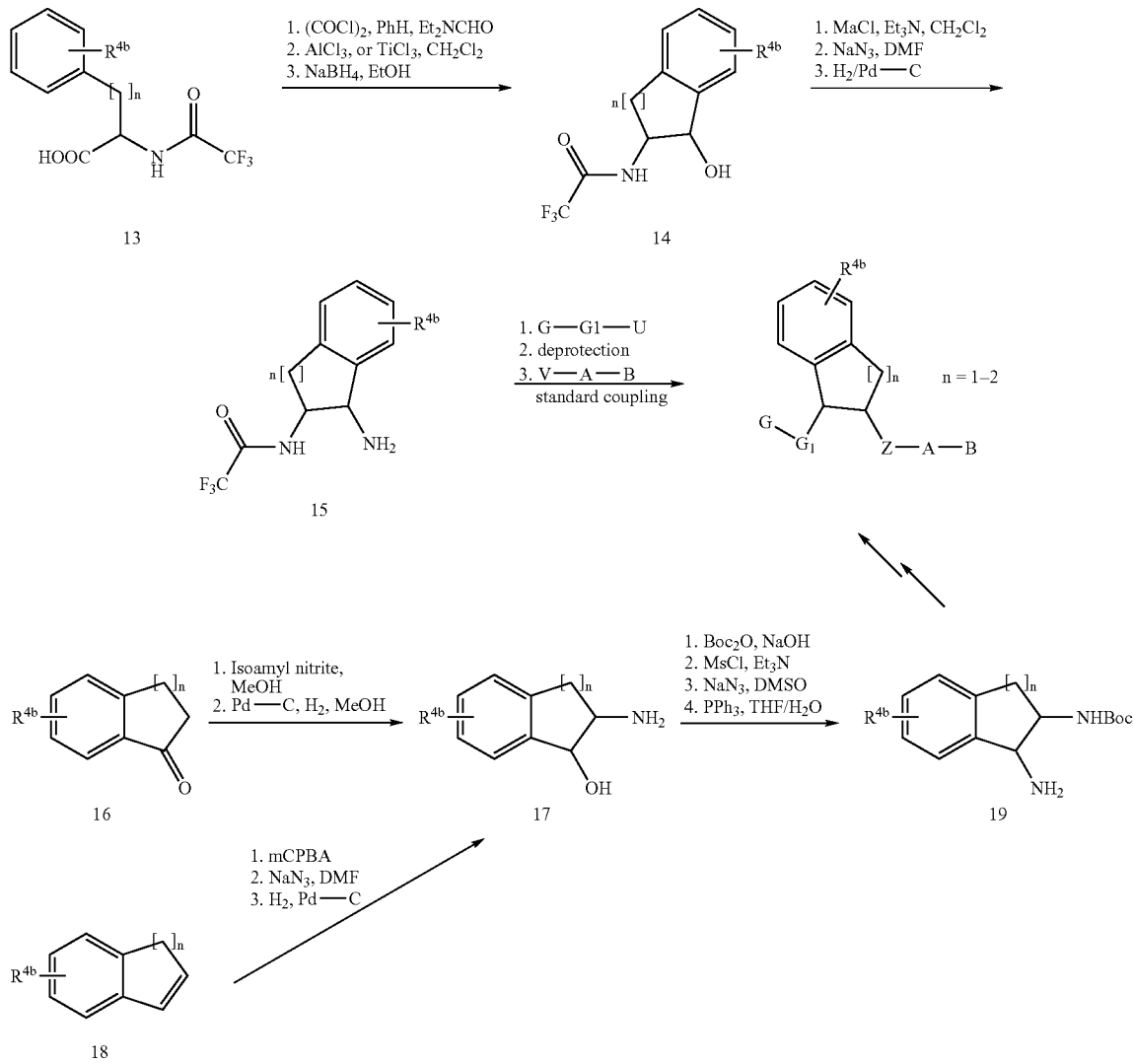

-continued

Enantiomerically pure product can be prepared from enatiomerically pure 5:

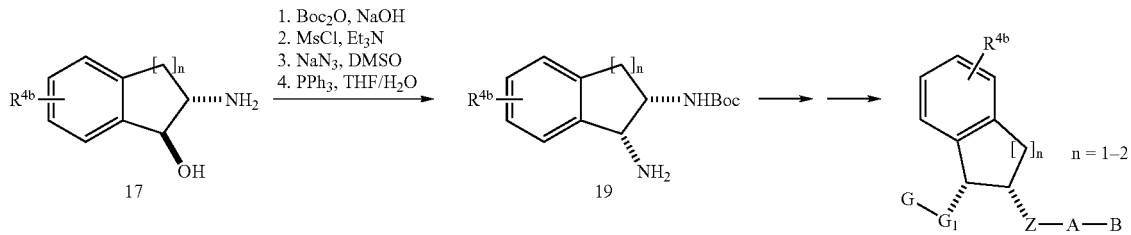

Scheme 12 depicts numerous spiro and bridged M intermediates that can be used to prepare compounds of the present invention. These intermediates can be prepared using methods known to those of ordinary skill in the art and using the methods described previously.

Scheme 12

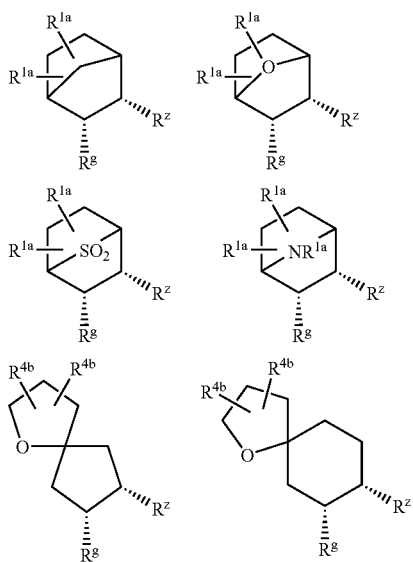

Scheme 13 depicts the synthesis of spiro intermediates M. Epoxidation of olefin 20 followed by displacement with TMSN$_3$ and reduction with 10-CSA can provide the amino alcohol intermediate 21. Protection of the amino and alcohol groups followed by nucleophilc addition to the carbonyl group and spiro ring formation can afford the spiro tetrahydrafuran intermediate 22. Compound 22 can undergo sequence of reactions similar to those described previously to give the compounds of the present invention.

Scheme 13

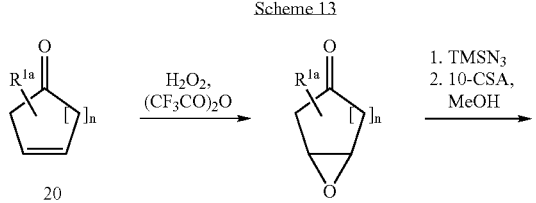

-continued

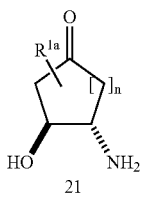

1. (Boc)$_2$O, NaOH
2. TBSCl, Et$_3$N
3. BrMgCH$_2$CH$_2$CH$_2$O—PG
4. Deprotection
5. TsCl

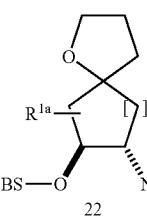

1. TBAF, THF
2. MsCl, Et$_3$N
3. NaN$_3$
4. PPh$_3$, THF/H$_2$O
5. G—G1—U
6. deprotection
7. V—A—B

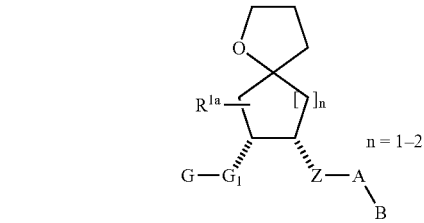

Diaminolactam derivatives 23 and 24 can be prepared from commercially available β-hydroxylactones as shown in Scheme 14. Dianion formation followed by treatment with trisyl azide and then hydrogenation should provide amino alcohol intermediate 25. Mesylation followed by replacement with NaN$_3$ should generate compound 26. The lactone 27 can then be transferred to the lactam 28 by treatment with NH$_2$R and mesylation, followed by ring formation with NaH. The final product 23 can then be prepared from 28 by using reactions described previously.

Scheme 14

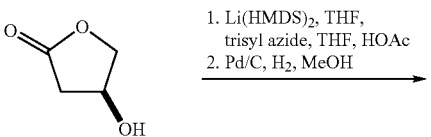

1. Li(HMDS)$_2$, THF, trisyl azide, THF, HOAc
2. Pd/C, H$_2$, MeOH

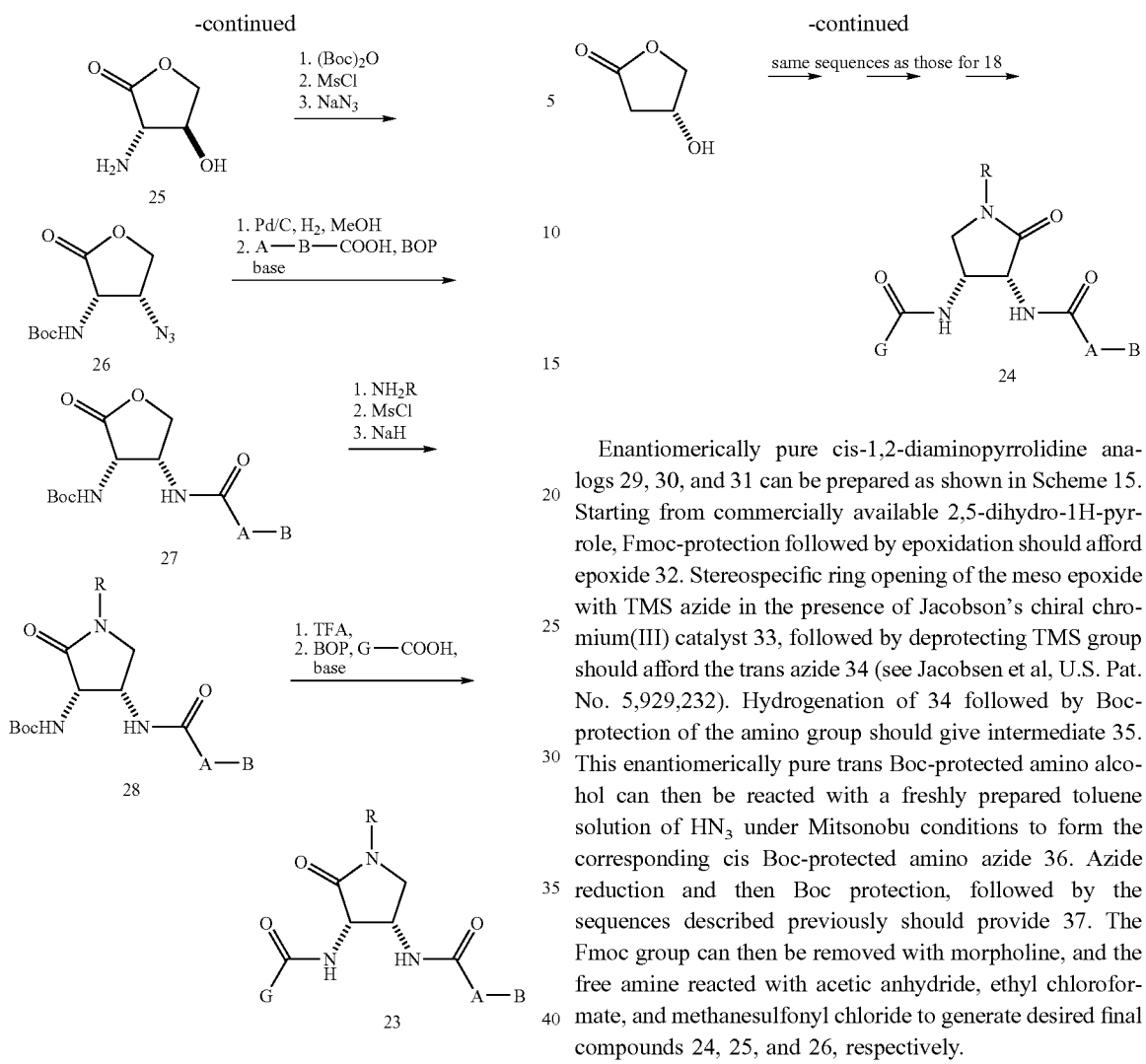

Enantiomerically pure cis-1,2-diaminopyrrolidine analogs 29, 30, and 31 can be prepared as shown in Scheme 15. Starting from commercially available 2,5-dihydro-1H-pyrrole, Fmoc-protection followed by epoxidation should afford epoxide 32. Stereospecific ring opening of the meso epoxide with TMS azide in the presence of Jacobson's chiral chromium(III) catalyst 33, followed by deprotecting TMS group should afford the trans azide 34 (see Jacobsen et al, U.S. Pat. No. 5,929,232). Hydrogenation of 34 followed by Boc-protection of the amino group should give intermediate 35. This enantiomerically pure trans Boc-protected amino alcohol can then be reacted with a freshly prepared toluene solution of $HN_3$ under Mitsonobu conditions to form the corresponding cis Boc-protected amino azide 36. Azide reduction and then Boc protection, followed by the sequences described previously should provide 37. The Fmoc group can then be removed with morpholine, and the free amine reacted with acetic anhydride, ethyl chloroformate, and methanesulfonyl chloride to generate desired final compounds 24, 25, and 26, respectively.

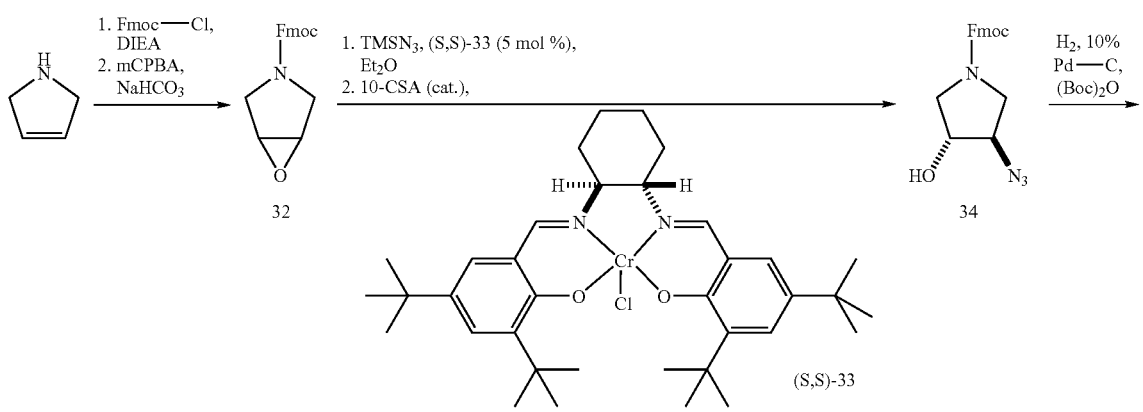

-continued

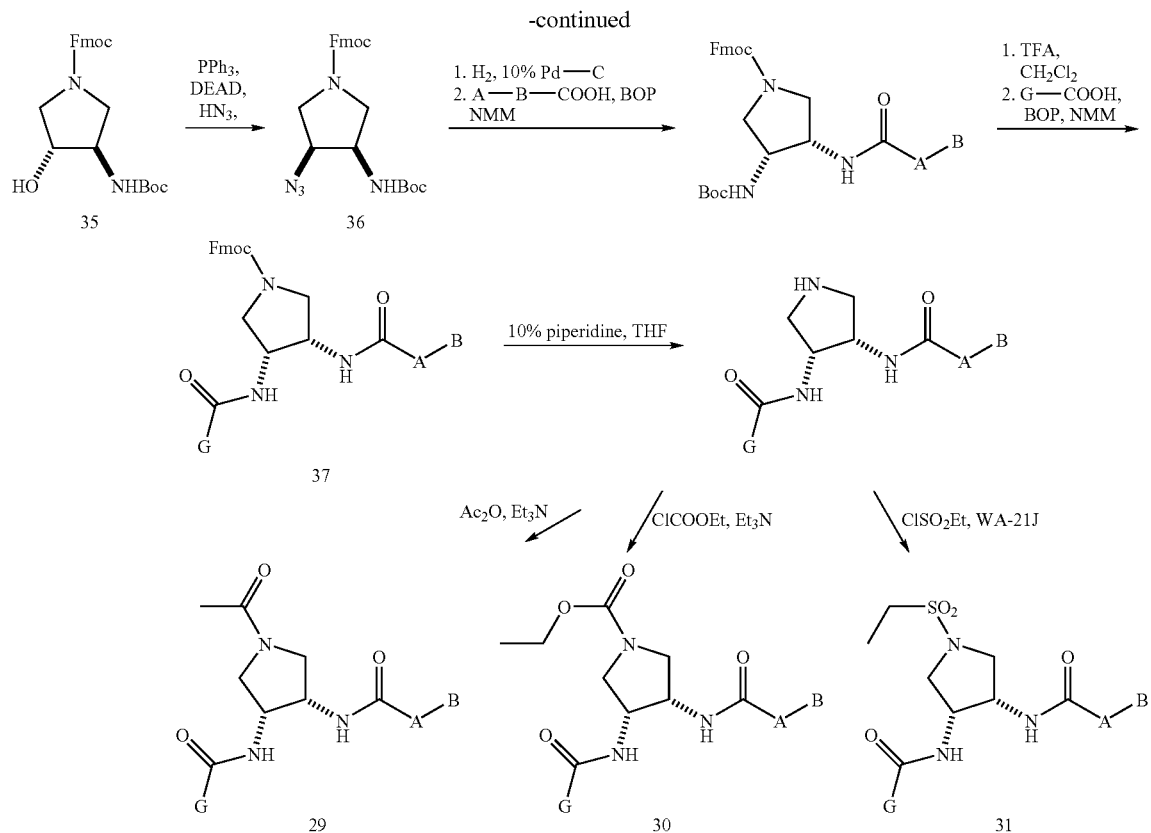

Utility

Other features of the invention will become apparent in the course of the following descriptions of exemplary embodiments that are given for illustration of the invention and are not intended to be limiting thereof.

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70–80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

(1R, 2S)-3-Chloro-1H-indole-6-carboxylic acid {2-[4-(2-dimethylaminomethyl-imidazol-1-yl)-benzoylamino]-cyclopentyl}-amide, trifluoroacetic acid salt

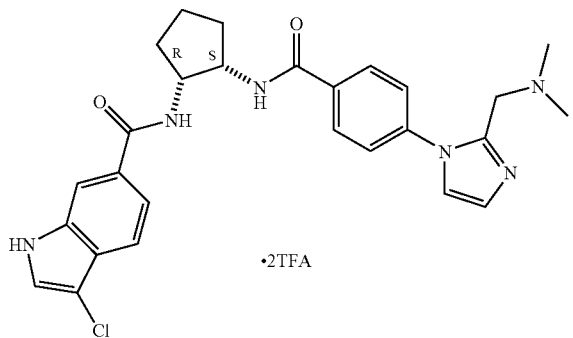

Part A. To a solution of (1S, 2S)-2-benzyloxycyclopentyl-amine (9.8 g, 51.2 mmol) in THF (150 mL) was added Et$_3$N (13.6 mL, 0.10 mol) and (Boc)$_2$O (12.30 g, 56.4 mmol) sequentially at 0° C. The reaction mixture was stirred overnight at room temperature and diluted with EtOAc (200 mL). The organic phase was washed with H$_2$O, brine, and dried (Na$_2$SO$_4$). The solvent was evaporated to afford (1S, 2S)-2-benzyloxy-cyclopentyl-carbamic acid tert-butyl ester (14.90 g, 100%) as a slight yellow solid. MS m/z 293.0 ([M+H]$^+$).

Part B. The product from Part A (10.0 mg, 34.2 mmol) was dissolved in ethanol (100 mL), and Pd/C (800 mg, 5%) was added. The reaction mixture was hydrogenated at 25 psi with stirring for 4 h and filtered through a pad of Celite®. The filtrate was evaporated to afford (1S, 2S)-2-hydroxy-cyclopentyl-carbamic acid tert-butyl ester (6.84 g, 99%) as a white solid. MS m/z 202.0 ([M+H]$^+$).

Part C. To a solution of the product from Part B (4.95 g, 24.6 mmol) in CH$_2$Cl$_2$ (50 mL) was added Et$_3$N (4.11 mL, 29.51 mmol) and MsCl (2.09 g, 27.05 mmol) sequentially at 0° C. The reaction mixture was stirred for 2 h at 0° C., then quenched with H$_2$O, and extracted with EtOAc (3×50 mL). The organic phase was washed with H$_2$O, brine, and dried (Na$_2$SO$_4$). The solvent was evaporated to afford (1S, 2S)-methanesulfonic acid 2-tert-butoxycarbonylamino-cyclopentyl ester (6.35 g, 92%) as a white solid. MS m/z 297.0 ([M+NH$_4$]$^+$).

Part D. NaN$_3$ (4.40 g, 67.7 mmol) was added to a solution of the product from Part C (6.30 g, 22.6 mmol) in DMF (50 mL). The reaction mixture was heated at 80° C. for 12 h with vigorous stirring. The reaction was cooled to room temperature, poured into water, and extracted with EtOAc (4×100 mL). The extracts were combined and washed with H$_2$O, aqueous LiCl (10%), brine, and dried (Na$_2$SO$_4$). The solvent was evaporated and the residue was taken to next step without purification. The residue from above reaction was dissolved in ethanol (200 mL), and Pd/C (300 mg, 5%) was added. The reaction mixture was hydrogenated at 1 atm with stirring for 24 h, and filtered through a pad of Celite®. The filtrate was evaporated to afford (1S, 2R)-2-amino-cyclopentyl-carbamic acid tert-butyl ester (6.84 g, 99%) as a white solid. MS m/z 201.0 ([M+H]$^+$).

Part E. 3-Chloro-1H-indole-6-carboxylic acid (234.7 mg, 1.2 mmol) and was dissolved in THF (5 mL) and cooled at 0° C. To this solution was added oxylyl chloride (0.12 mL, 1.4 mmol) followed by the addition of one drop of DMF. The mixture was stirred at 0° C. for 2 h. It was concentrated in vacuo. The residue was dissolved in THF (5 mL), and the product from Part D (200 mg, 1.0 mmol) was added followed by the slow addition of Et$_3$N (0.21 mL. 1.5 mmol). The reaction mixture was stirred at rt for 1 h. It was diluted with ethyl acetate; washed with water, aqueous LiCl (10%), and brine; and dried (Na$_2$SO$_4$). After evaporation of the solvent, the residue was purified on silica gel to afford (1S, 2R)-{2-[(3-chloro-1H-indole-6-carbonyl)-amino]-cyclopentyl}-carbamic acid tert-butyl ester (278 mg, 75%) as a white solid.

Part F. The product from Part E (278 mg, 0.74 mmol) was suspended in CH$_2$Cl$_2$ (3 mL), and TFA (3 mL) was added. A clear solution was obtained and stirred for 1 h at ambient temperature. The resulting solution was concentrated. The residue was partitioned between EtOAc and aqueous Na$_2$CO$_3$. The aqueous solution was extracted with EtOAc (3×10 mL), and the extracts were combined and washed with brine and dried (Na$_2$SO$_4$). Evaporation of the solvent afforded (1R, 2S)-3-chloro-1H-indole-6-carboxylic acid (2-amino-cyclopentyl)-amide (207 mg, 99%) as a white solid that was taken to next step without purification. MS m/z 278.0 ([M+H]$^+$).

Part G. 4-Iodo-benzoic acid methyl ester (1.42 g, mmol) and (1H-imidazol-2-ylmethyl)-dimethyl-amine (0.68 g, mmol) were stirred in DMSO (3.5 mL) under $N_2$. $K_2CO_3$ (1.52 g, mmol) was added followed by the addition of CuI (0.52 g, mmol) and 1,10-phenanthroline (0.46 g, mmol). The reaction mixture was heated at 120–125° C. for 2 h. After cooling, EtOAc was added. It was washed with dil. $NH_3H_2O$, $H_2O$, brine, dried over $MgSO_4$, filtered, and concentrated to dryness. The residue was purified by FCC (silica gel, $CH_2Cl_2$:EtOAc=1:0 to 0:1, then 10% MeOH) to give pure 4-(2-dimethylaminomethyl-imidazol-1-yl)-benzoic acid methyl ester (0.56 g, yield 40%). $^1$H NMR ($CDCl_3$) δ 7.84 (d, J=8.4 Hz, 2H), 7.40 (d, J=8.4 Hz, 2H), 6.87 (d, J=0.9 Hz, 1H), 6.80 (d, J=0.9 Hz, 1H), 3.65 (s, 3H), 3.10 (s, 2H), 1.96 (s, 6H) ppm.

Part H. The product from Part G (0.52 g, 2.0 mmol) was stirred in MeOH (10 mL). 1N NaOH (4.0 mL, 2.0 eq) was added. The mixture was stirred at rt for 1 day. It was evaporated, and acidified with 1N HCl. The mixture was concentrated to dryness to give crude 4-(2-dimethylaminomethyl-imidazol-1-yl)-benzoic acid and used directly to the next step. LC/MS-ESI 246.13 (M+H), $t_R$=0.87 min (10–90% MeOH in $H_2O$ with 10 mM $NH_4OAc$ in a 4-min run). $^1$H NMR (DMSO-$d_6$) δ 7.73 (d, J=8.1 Hz, 2H), 7.23 (d, J=8.2 Hz, 2H), 7.15 (d, J=1.2 Hz, 1H), 6.75 (d, J=1.1 Hz, 1H), 3.09 (m, 2H), 1.90 (s, 6H) ppm.

Part I. The product from Part F (11.2 mg, 0.04 mmol), the product from Part H (9.8 mg, 0.04 mmol), BOP (26.5 mg, 0.06 mmol), and diisopropylethylamine (0.014 mL, 0.08 mmol) were dissolved in DMF (0.2 mL) and stirred for 4 h at room temperature. The reaction mixture was diluted with ethyl acetate, washed with water, aqueous LiCl (10%), brine, and dried ($MgSO_4$). After evaporation of the solvent, the residue was purified on RP HPLC using gradient $CH_3OH$—$H_2O$-TFA to afford (1R, 2S)-3-chloro-1H-indole-6-carboxylic acid {2-[4-(2-dimethylaminomethyl-imidazol-1-yl)-benzoylamino]-cyclopentyl}-amide (13.3 mg, 46%) as a TFA salt. $^1$H NMR (400 MHz, $CD_3OD$) δ 1.60–1.75 (m, 1H), 1.80–2.05 (m, 2H), 2.04–2.20 (m, 1H), 2.77 (s, 6H), 4.35 (s, 2H), 4.45–4.70 (m, 2H), 7.27 (s, 1H), 7.38 (s, 1H), 7.42–7.53 (m, 5H), 7.89–7.94 (m, 3H); MS 505.4 [(MH)$^+$]; HRMS (ESI) m/z calcd for $C_{27}H_{29}ClN_6O_2$ ([M+H]$^+$) 505.2119, found 505.2130.

Examples 2–7 were prepared using the same procedure as that described for Example 1.

Example 2

(1R, 2S)-5-Chloro-thiophene-2-carboxylic acid {2-[4-(2-dimethylaminomethylimidazol-1-yl)-benzoylamino]-cyclopentyl}-amide, trifluoroacetic acid salt

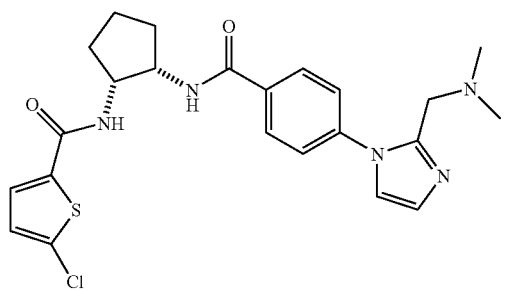

$^1$H NMR (400 MHz, $CD_3OD$) δ 7.93 (d, J=8.5 Hz, 2H), 7.55 (d, J=4.1 Hz, 1H), 7.51 (d, J=8.4 Hz, 2H), 7.47 (d, J=1.2 Hz, 1H), 7.30 (d, J=1.3 Hz, 1H), 6.97 (d, J=4.0 Hz, 1H), 4.50 (m, 2H). 4.41 (s, 2H), 2.83 (s, 6H), 2.13 (m, 2H), 1.97 (m, 1H), 1.86 (m, 2H), 1.69 (m, 1H) ppm. Anal. LC/MS (ESI) 472.08, 474.07 (M+H), 470.22, 472.23 (M–H), $t_R$=1.72 min (10%–90% MeOH in $H_2O$ with 10 mM $NH_4OAc$ in a 2-min run).

Example 3

(1R, 2S)-5-Chloro-thiophene-2-carboxylic acid {2-[4-(2-dimethylaminomethyl-imidazol-1-yl)-benzoylamino]-cyclohexyl}-amide, trifluoroacetic acid salt

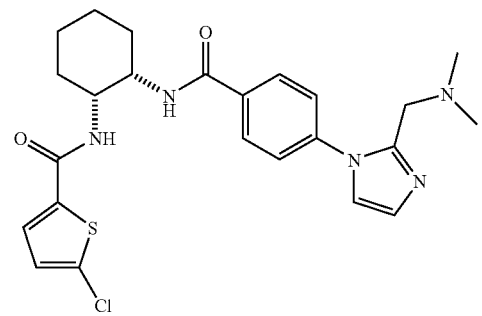

$^1$H NMR (400 MHz, $CD_3OD$) δ 8.00 (d, J=8.5 Hz, 2H), 7.63 (d, J=4.1 Hz, 1H), 7.57 (d, J=8.5 Hz, 2H), 7.51 (d, J=1.4 Hz, 1H), 7.34 (d, J=1.4 Hz, 1H), 7.03 (d, J=4.1 Hz, 1H), 4.45 (s+m, 3H), 4.34 (m, 1H), 2.86 (s, 6H), 1.91–1.76 (m, 6H), 1.57 (m, 2H) ppm. Anal. LC/MS (ESI) 486.12, 488.11 (M+H), 484.27, 486.27 (M–H), $t_R$=1.74 min (10%–90% MeOH in $H_2O$ with 10 mM $NH_4OAc$ in a 2-min run).

Example 4

(1R, 2S)-3-Chloro-1H-indole-6-carboxylic acid {2-[4-(2-dimethylaminomethyl-imidazol-1-yl)-benzoylamino]-cyclohexyl}-amide, trifluoroacetic acid salt

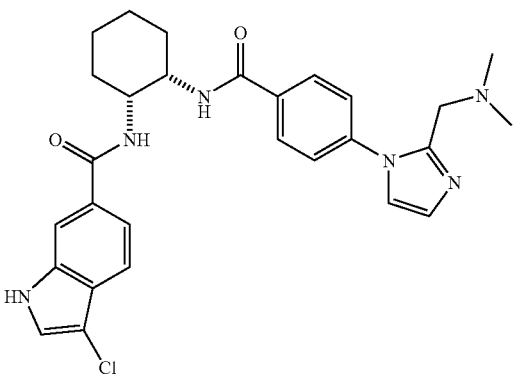

$^1$H NMR (400 MHz, MeOH-$d_4$) δ 8.02 (d, J=8.6 Hz, 2H), 7.95 (s, 1H), 7.59 (m, 2H), 7.55 (d, J=8.6 Hz, 2H), 7.48 (d, J=1.3 Hz, 1H), 7.44 (m, 1H), 7.30 (d, J=1.3 Hz, 1H), 4.53 (m, 1H), 4.41 (s, 2H), 2.84 (s, 6H), 1.99–1.75 (m, 6H), 1.63 (m, 2H) ppm. LC/MS ESI 519.43, 521.43 (M$^+$), 517.38, 519.38 (M$^-$), $t_R$=3.44 min (10–90% MeOH in $H_2O$ with 10 mM $NH_4OAc$ in a 4-min run).

Example 5

(1R, 2S)-3-Chloro-1H-indole-6-carboxylic acid {2-[(1-isopropyl-piperidine-4-carbonyl)-amino]-cyclohexyl}-amide, trifluoroacetic acid salt

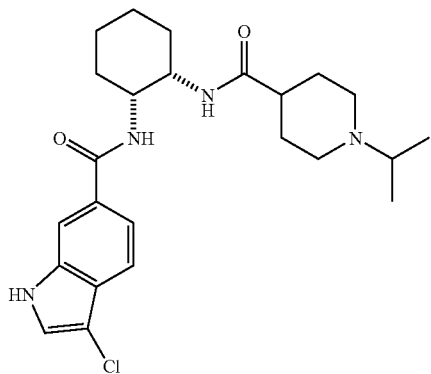

$^1$H NMR (400 MHz, Methanol-d$_4$) δ 7.90 (s, 1H), 7.55 (m, 1H), 7.42 (m, 2H), 4.36 (m, 1H), 4.22 (m, 1H), 3.47 (m, 3H), 2.97 (m, 2H), 2.53 (m, 1H), 2.05 (m, 2H), 1.92 (m, 1H), 1.77 (m, 6H), 1.54 (m, 2H), 1.32 (d, J=6.6 Hz, 6H), 1.18 (m, 1H) ppm. LC-MS (ESI) 445.47 (M+H), 443.41 (M–H), t$_R$=2.66 min (10–90% MeOH in H$_2$O in a 4-min run).

Example 6

(1R, 2S)-3-Chloro-1H-indole-6-carboxylic acid [2-(4-morpholin-4-yl-benzoylamino)-cyclopentyl]-amide, trifluoroacetic acid salt

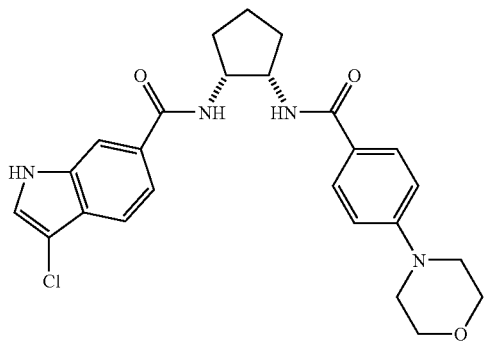

$^1$H NMR (400 MHz, methanol-d$_4$) δ 7.84 (s, 1H), 7.65 (d, J=9.0 Hz, 2H), 7.50 (m, 2H), 7.39 (m, 1H), 6.90 (d, J=9.0 Hz, 2H), 4.52 (m, 2H), 3.79 (m, 4H), 3.20 (m, 4H), 2.16 (m, 2H), 1.96 (m, 1H), 1.84 (m, 2H), 1.70 (m, 1H) ppm. LC/MS ESI, 467.40 (M+H), 465.36 (M–H), t$_R$=3.12 min (10–90% MeOH in H$_2$O in a 4-min run).

Example 7

(1R, 2S)-3-Chloro-1H-indole-6-carboxylic acid [2-(4-morpholin-4-yl-benzoylamino)-cyclohexyl]-amide, trifluoroacetic acid salt

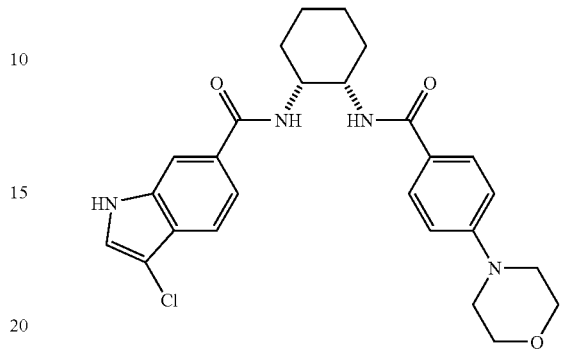

$^1$H NMR (400 MHz, MeOH-d$_4$) δ 7.91 (s, 1H), 7.74 (d, J=8.8 Hz, 2H), 7.57 (m, 2H), 7.42 (m, 1H), 6.98 (d, J=8.8 Hz, 2H), 4.40 (m, 2H), 3.83 (t, J=4.8 Hz, 4H), 3.25 (t, J=4.8 Hz, 4H), 1.95–1.75 (m, 6H), 1.61 (m, 2H) ppm. HRMS ESI, calcd for C$_{26}$H$_{30}$ClN$_4$O$_3$ for 481.2006 (M+H). found 481.2019.

Example 8

(1R, 2S)-3-Chloro-1H-indole-6-carboxylic acid {2-[4-(2-dimethylaminomethyl-imidazol-1-yl)-benzoylamino]-indan-1-yl}-amide, trifluoroacetic acid salt

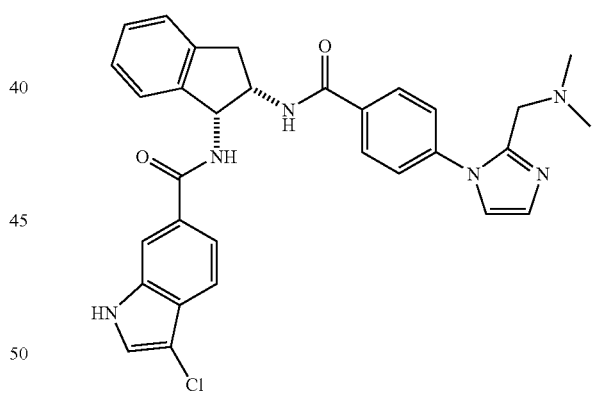

Part A. To a solution of (1R, 2S)-1-amino-indan-2-ol (5.04 g, 33.8 mmol) in THF (50 mL) cooled at 0° C. was added triethylamine (5.65 mL, 40.6 mmol) and (Boc)$_2$O (7.37 g, 33.8 mmol) sequentially. The reaction mixture was stirred overnight at room temperature, quenched with H$_2$O, and extracted with EtOAc (3×50 mL). The organic extracts were combined, washed with water, brine, and dried (MgSO$_4$). Removal of the solvent gave the desired product (1R, 2S)-(2-hydroxy-indan-1-yl)-carbamic acid tert-butyl ester (8.39 g, 99%) as a white solid that was taken to the next step without purification. MS m/z 250 [(M+H)$^+$].

Part B. The product from Part A (2.49 g, 10 mmol), p-nitrobenzoic acid (1.67 g, 10 mmol), and triphenylphosphine (4.20 g, 16 mmol) were dissolved in THF (20 mL) and cooled to 0° C. A solution of DEAD (2.26 g, 13 mmol) in THF (10 mL) was then added dropwise over 10 min. The reaction mixture was stirred for 30 min at 0° C. and 4 h at room temperature and then concentrated. The residue was dissolved in EtOAc (100 mL), washed with Na$_2$CO$_3$ (sat'd), brine, and dried (MgSO$_4$). The solvent was removed and the residue was purified on silica gel, using 2% EtOAc—CHCl$_3$, and crystallized from EtOAc-hexane to afford (1R, 2R)-4-nitro-benzoic acid 1-tert-butoxycarbonylamino-indan-2-yl ester (4.50 g, 57%) as a white solid. MS m/z 399 [(M+H)$^+$].

Part C. A solution of product from Part B (4.0 g, 10 mmol) in CH$_2$Cl$_2$ (20 mL) was added to a solution of NaOCH$_3$ in CH$_3$OH (25% wt, 6.86 mL) over 10 min at 0° C. The reaction mixture was stirred for 2 h at 0° C., quenched with H$_2$O, and extracted with EtOAc (3×50 mL). The extracts were combined, washed with H$_2$O, brine, and dried (Na$_2$SO$_4$). After evaporation of the solvent, the residue was chromatographed on silica gel using 10–50% EtOAc—CH$_2$Cl$_2$ (gradient) to afford (1S, 2R)-(2-hydroxy-indan-1-yl)-carbamic acid tert-butyl ester (1.94 g, 78%) as a white solid. MS m/z 250 [(M+H)$^+$].

Part D. To a solution of the product from Part C (1.0 g, 4.01 mmol) in CH$_2$Cl$_2$ (10 mL), what was cooled at 0° C., were sequentially added triethylamine (0.73 mL, 5.21 mmol) and MsCl (0.34 mL, 4.41 mmol). The reaction mixture was stirred for 2 hours at 0° C., quenched with H$_2$O, and extracted with EtOAc (3×20 mL). The organic extracts were combined, washed with water, brine, and dried (MgSO$_4$). The solvent was evaporated, and the residue was purified via silica gel chromatography with 10–30% (gradient) EtOAc-hexane to afford product (1R, 2R)-methanesulfonic acid 1-tert-butoxycarbonylamino-indan-2-yl ester (1.24 g, 95%) as a white solid. MS m/z 328 [(M+H)$^+$].

Part E. NaN$_3$ (739 mg, 11.4 mmol) was added to a solution of the product from Part D (1.24 g, 3.79 mmol) in DMF (20 mL), and the reaction mixture was heated at 100° C. for 2 h with vigorous stirring. The reaction mixture was cooled to room temperature, poured into water, and extracted with EtOAc (4×50 mL). The extracts were combined; washed with H$_2$O, aqueous LiCl (10%), and brine; and,dried (Na$_2$SO$_4$). The solvent was evaporated. The residue was filtered through a pad of silica gel and washed with 30% EtOAc-hexanes (200 mL). The filtrate was evaporated to afford (1R, 2S)-(2-azido-indan-1-yl)-carbamic acid tert-butyl ester (487 mg, 47%) as a white solid. MS m/z 275 [(M+H)$^+$].

Part F. To a solution of the product of Part E (470 mg, 1.71 mmol) in ethanol (100 mL) was added Pd/C (100 mg, 5%). The reaction mixture was hydrogenated at 50 psi with stirring for 6 h, and filtered through a pad of Celite®. The filtrate was evaporated to afford (1R, 2S)-(2-amino-indan-1-yl)-carbamic acid tert-butyl ester (400 mg, 94%) as a white solid. MS m/z 249 [(M+H)$^+$].

Part G. Following similar procedures as those for Parts E, F and I of Example 1 but using the product of Part F, 3-chloro-1H-indole-6-carboxylic acid, and 4-(2-dimethylaminomethyl-imidazol-1-yl)-benzoic acid as the starting materials, the title compound was obtained. 1H NMR (400 MHz, MeOH-d$_4$) δ 7.81 (d+s, J=8.7 Hz, 3H), 7.43 (d, J=1.6 Hz, 1H), 7.41 (m, 1H), 7.39 (d, J=6.6 Hz, 1H), 7.34 (d, J=8.6 Hz, 2H), 7.29 (m, 2H), 7.27–7.17 (m, 3H), 7.15 (d, J=1.8 Hz, 1H), 5.72 (d, J=6.8 Hz, 1H), 5.01 (q, J=7.1 Hz, 1H), 4.23 (s, 2H), 3.28 (dd, J=16.2, 7.5 Hz, 1H), 3.13 (m, 1H), 2.67 (s, 6H) ppm. LC/MS ESI, 553.22 (M+H), t$_R$=1.56 min (10–90% MeOH in H$_2$O with 0.1% TFA in a 2-min run).

Examples shown in Table 1 below can be prepared by following the procedures of Examples 1–8 and by using appropriate cyclic diamines prepared from commercially available starting materials. Table 1 contains representative species of the present invention. Examples 1–1168 recite a G group, Z group, and central ring that is specifically shown in the legend at the top of the table.

TABLE 1

G Groups

G-1: 6-Chloro-thieno[2,3-b]pyridin-2-yl-C(O)NH—
G-2: 6-Chloro-naphthalen-2-yl-C(O)NH—
G-3: 2-Chloro-quinolin-6-yl-C(O)NH—
G-4: 3-Chloro-1H-indol-6-yl-C(O)NH—
G-5: 6-Chloro-benzo[b]thiophen-2-yl-C(O)NH—
G-6: 5-Chloro-thiophen-2-yl-C(O)NH—
G-7: 4-Chloro-phenyl-C(O)NH—
G-8: 5-Chloro-1H-indol-2-yl-C(O)NH—

Z Groups

Z-1: 2'-methanesulfonyl-biphen-4-yl-NHC(O)—
Z-2: 2'-sulfamoyl-biphen-4-yl-NHC(O)—
Z-3: 2'-dimethylaminomethyl-biphen-4-yl-NHC(O)—
Z-4: 2'-pyrrolidin-1-ylmethyl-biphen-4-yl-NHC(O)—
Z-5: 2'-(3-hydroxy-pyrrolidin-1-ylmethyl)-biphen-4-yl-NHC(O)—
Z-6: 4-(2-dimethylaminomethyl-imidazol-1-yl)-phenyl-NHC(O)—
Z-7: 4-(2-pyrrolidin-1-ylmethyl-imidazol-1-yl)-phenyl-NHC(O)—
Z-8: 4-[2-(3-hydroxy-pyrrolidin-1-ylmethyl)-imidazol-1-yl]-phenyl-NHC(O)—
Z-9: 4-(2-morpholin-4-ylmethyl-imidazol-1-yl)-phenyl-NHC(O)—
Z-10: 4-[2-(1,1-dioxo-1λ$^6$-thiomorpholin-4-y1methyl)-imidazol-1-yl]-phenyl-NHC(O)—
Z-11: 4-(1-methyl-4,5-dihydro-1H-imidazol-2-yl)-phenyl-NHC(O)—
Z-12: 4-(1-methyl-1,4,5,6-tetrahydro-pyrimidin-2-yl)-phenyl-NHC(O)—
Z-13: 4-(4-methyl-[1,4]diazepan-1-yl)-phenyl-NHC(O)—
Z-14: 4-(pyrrolidine-1-carbonyl)-phenyl-NHC(O)—
Z-15: 2'-dimethylaminomethyl-biphen-4-yl-NHC(O)—
Z-16: 4-(2-dimethylaminomethyl-imidazol-1-yl)-phenyl-NHC(O)—
Z-17: 4-(1-isopropyl)-piperidinyl-NHC(O)—
Z-18: 4-(1-cyclopropyl)-piperidinyl-NHC(O)—
Z-19: 4-(1-cyclohexyl)-piperidinyl-NHC(O)—
Z-20: 4-[1-methylpiperidin-4-yl]-piperidinyl-NHC(O)—
Z-21: 4-[1-(tetrahydro-2H-pyran-4-yl)]-piperidinyl-NHC(O)—

Central Rings cyclopentyl =

carbomethoxy-cyclopentyl =

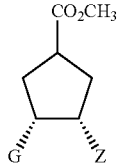

hydroxymethyl-cyclopentyl =

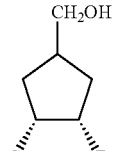

TABLE 1-continued

| Name | Structure |
|---|---|
| amino-cyclopentyl = | cyclopentane with NH₂, G (dashed), Z (dashed) |
| cyclohexyl = | cyclohexane with G (dashed) and Z |
| dimethylaminocarbonyl-cyclohexyl | cyclohexane with G (dashed), Z, and C(O)N(CH₃)₂ |
| dimethylaminocarbonyl-cyclohexyl-A = | cyclohexane with C(O)N(CH₃)₂, G (dashed), Z |
| methoxy-cyclohexyl = | cyclohexane with G (dashed), Z, OCH₃ |
| methoxy-cyclohexyl-A = | cyclohexane with OCH₃, G (dashed), Z |
| tetrahydrofuran = | THF ring with G (dashed), Z |
| tetrahydrofuran-A = | THF ring with G (dashed), Z |
| 1-methyl-pyrrolidine = | pyrrolidine N—CH₃, G (dashed), Z |
| 1-methanesulfonyl-pyrrolidine = | pyrrolidine N—SO₂CH₃, G (dashed), Z |
| 1-carbomethoxy-pyrrolidine = | pyrrolidine N—CO₂CH₃, G (dashed), Z (dashed) |
| 1-dimethylaminocarbonyl-pyrrolidine = | pyrrolidine N—C(O)N(CH₃)₂, G (dashed), Z (dashed) |
| 1-acetyl-pyrrolidine = | pyrrolidine N—COCH₃, G (dashed), Z (dashed) |
| tetrahydrothiophenyl-dioxide = | tetrahydrothiophene-1,1-dioxide with G (dashed), Z (dashed) |
| indane = | indane with Z (dashed), G (dashed) |
| indane-A = | indane with Z, G (dashed) |
| 1-oxa-spiro[4,4]non-7-yl = | 1-oxaspiro[4.4]nonane with Z (dashed), G (dashed) |
| tetrahydropyran = | tetrahydropyran with G (dashed), Z |
| tetrahydropyran-A = | tetrahydropyran with G (dashed), Z |
| tetrahydropyran-B = | tetrahydropyran with G (dashed), Z |

TABLE 1-continued

| Name | Structure |
|---|---|
| 1-methyl-piperidine = | piperidine with N-CH3, G and Z substituents |
| 1-methyl-piperidine-A = | piperidine with N-CH3, G and Z substituents (alt) |
| 1-carbomethoxy-piperidine = | piperidine with N-CO2CH3, G and Z |
| 1-carbomethoxy-piperidine-A = | piperidine with N-CO2CH3, G and Z (alt) |
| 1-acetyl-piperidine = | piperidine with N-COCH3, G and Z |
| 1-acetyl-piperidine-A = | piperidine with N-COCH3, G and Z (alt) |
| 1-methylsulfonyl-piperidine = | piperidine with N-SO2CH3, G and Z |
| 1-methylsulfonyl-piperidine-A = | piperidine with N-SO2CH3, G and Z (alt) |
| 1-dimethylaminocarbonyl-piperidine = | piperidine with N-C(O)N(CH3)2, Z and G |
| 1-dimethylaminocarbonyl-piperidine-A = | piperidine with N-C(O)N(CH3)2, G and Z |
| 1-cyclopropylcarbonyl-piperidine = | piperidine with N-C(O)-cyclopropyl, G and Z |
| 1-cyclopropylcarbonyl-piperidine-A = | piperidine with N-C(O)-cyclopropyl, G and Z (alt) |
| 1-methoxy-cyclopropylcarbonyl-piperidine = | piperidine with N-C(O)-C(OCH3)(cyclopropyl), G and Z |
| 1-methoxy-cyclopropylcarbonyl-piperidine-A = | piperidine with N-C(O)-C(OCH3)(cyclopropyl), G and Z (alt) |
| tetrahydrothiopyran-dioxide = | tetrahydrothiopyran-1,1-dioxide with Z and G |
| tetrahydrothiopyran-dioxide-A = | tetrahydrothiopyran-1,1-dioxide with Z and G (alt) |
| 1,2,3,4-tetrahydro-naphthalen-1-yl = | tetrahydronaphthalene with Z and G |
| 1,2,3,4-tetrahydro-naphthalen-1-yl-A = | tetrahydronaphthalene with Z and G (alt) |
| 1,2,3,4-tetrahydro-naphthalen-2-yl = | tetrahydronaphthalene with Z and G at 2,3 positions |
| bicyclo[2.2.1]hepy-2-yl = | norbornane with G and Z |

TABLE 1-continued

| | | |
|---|---|---|
| 6,7-dihydro-5H-pyrrolo[1,2-c]imidazol-6-yl = | 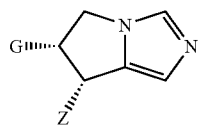 | |
| 6,7-dihydro-5H-pyrrolo[1,2-a]imidazol-6-yl = | 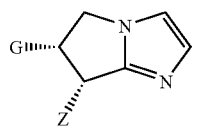 | |
| 5,6-dihydro-4H-pyrrolo[1,2-b]pyrazol-5-yl = | 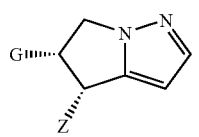 | |
| N-methyl-pyrrolidone | 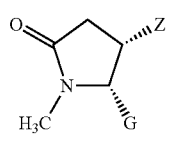 | |
| N-methyl-pyrrolidone-A | 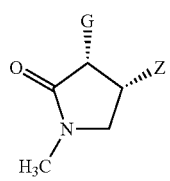 | |

| Ex. # | G group | Z group | Central Ring |
|---|---|---|---|
| 1. | G-1 | Z-1 | cyclopentyl |
| 2. | G-2 | Z-1 | cyclopentyl |
| 3. | G-3 | Z-1 | cyclopentyl |
| 4. | G-4 | Z-1 | cyclopentyl |
| 5. | G-5 | Z-1 | cyclopentyl |
| 6. | G-6 | Z-1 | cyclopentyl |
| 7. | G-1 | Z-1 | cyclohexyl |
| 8. | G-2 | Z-1 | cyclohexyl |
| 9. | G-3 | Z-1 | cyclohexyl |
| 10. | G-4 | Z-1 | cyclohexyl |
| 11. | G-5 | Z-1 | cyclohexyl |
| 12. | G-6 | Z-1 | cyclohexyl |
| 13. | G-1 | Z-2 | cyclopentyl |
| 14. | G-2 | Z-2 | cyclopentyl |
| 15. | G-3 | Z-2 | cyclopentyl |
| 16. | G-4 | Z-2 | cyclopentyl |
| 17. | G-5 | Z-2 | cyclopentyl |
| 18. | G-6 | Z-2 | cyclopentyl |
| 19. | G-1 | Z-2 | cyclohexyl |
| 20. | G-2 | Z-2 | cyclohexyl |
| 21. | G-3 | Z-2 | cyclohexyl |
| 22. | G-4 | Z-2 | cyclohexyl |
| 23. | G-5 | Z-2 | cyclohexyl |
| 24. | G-6 | Z-2 | cyclohexyl |
| 25. | G-1 | Z-3 | cyclopentyl |
| 26. | G-2 | Z-3 | cyclopentyl |
| 27. | G-3 | Z-3 | cyclopentyl |
| 28. | G-4 | Z-3 | cyclopentyl |
| 29. | G-5 | Z-3 | cyclopentyl |
| 30. | G-6 | Z-3 | cyclopentyl |
| 31. | G-1 | Z-3 | cyclohexyl |
| 32. | G-2 | Z-3 | cyclohexyl |
| 33. | G-3 | Z-3 | cyclohexyl |
| 34. | G-4 | Z-3 | cyclohexyl |
| 35. | G-5 | Z-3 | cyclohexyl |
| 36. | G-6 | Z-3 | cyclohexyl |
| 37. | G-1 | Z-4 | cyclopentyl |
| 38. | G-2 | Z-4 | cyclopentyl |
| 39. | G-3 | Z-4 | cyclopentyl |
| 40. | G-4 | Z-4 | cyclopentyl |
| 41. | G-5 | Z-4 | cyclopentyl |
| 42. | G-6 | Z-4 | cyclopentyl |
| 43. | G-1 | Z-4 | cyclohexyl |
| 44. | G-2 | Z-4 | cyclohexyl |
| 45. | G-3 | Z-4 | cyclohexyl |
| 46. | G-4 | Z-4 | cyclohexyl |
| 47. | G-5 | Z-4 | cyclohexyl |
| 48. | G-6 | Z-4 | cyclohexyl |
| 49. | G-1 | Z-5 | cyclopentyl |
| 50. | G-2 | Z-5 | cyclopentyl |
| 51. | G-3 | Z-5 | cyclopentyl |
| 52. | G-4 | Z-5 | cyclopentyl |
| 53. | G-5 | Z-5 | cyclopentyl |
| 54. | G-6 | Z-5 | cyclopentyl |
| 55. | G-1 | Z-5 | cyclohexyl |
| 56. | G-2 | Z-5 | cyclohexyl |
| 57. | G-3 | Z-5 | cyclohexyl |
| 58. | G-4 | Z-5 | cyclohexyl |
| 59. | G-5 | Z-5 | cyclohexyl |
| 60. | G-6 | Z-5 | cyclohexyl |
| 61. | G-1 | Z-6 | cyclopentyl |
| 62. | G2 | Z-6 | cyclopentyl |
| 63. | G-3 | Z-6 | cyclopentyl |
| 64. | G-4 | Z-6 | cyclopentyl |
| 65. | G-5 | Z-6 | cyclopentyl |
| 66. | G-6 | Z-6 | cyclopentyl |
| 67. | G-1 | Z-6 | cyclohexyl |
| 68. | G-2 | Z-6 | cyclohexyl |
| 69. | G-3 | Z-6 | cyclohexyl |
| 70. | G-4 | Z-6 | cyclohexyl |
| 71. | G-5 | Z-6 | cyclohexyl |
| 72. | G-6 | Z-6 | cyclohexyl |
| 73. | G-1 | Z-7 | cyclopentyl |
| 74. | G-2 | Z-7 | cyclopentyl |
| 75. | G-3 | Z-7 | cyclopentyl |
| 76. | G-4 | Z-7 | cyclopentyl |
| 77. | G-5 | Z-7 | cyclopentyl |
| 78. | G-6 | Z-7 | cyclopentyl |
| 79. | G-1 | Z-7 | cyclohexyl |
| 80. | G-2 | Z-7 | cyclohexyl |
| 81. | G-3 | Z-7 | cyclohexyl |
| 82. | G-4 | Z-7 | cyclohexyl |
| 83. | G-5 | Z-7 | cyclohexyl |
| 84. | G-6 | Z-7 | cyclohexyl |
| 85. | G-1 | Z-8 | cyclopentyl |
| 86. | G-2 | Z-8 | cyclopentyl |
| 87. | G-3 | Z-8 | cyclopentyl |
| 88. | G-4 | Z-8 | cyclopentyl |
| 89. | G-5 | Z-8 | cyclopentyl |
| 90. | G-6 | Z-8 | cyclopentyl |
| 91. | G-1 | Z-8 | cyclohexyl |
| 92. | G-2 | Z-8 | cyclohexyl |
| 93. | G-3 | Z-8 | cyclohexyl |
| 94. | G-4 | Z-8 | cyclohexyl |
| 95. | G-5 | Z-8 | cyclohexyl |
| 96. | G-6 | Z-8 | cyclohexyl |
| 97. | G-1 | Z-9 | cyclopentyl |
| 98. | G-2 | Z-9 | cyclopentyl |
| 99. | G-3 | Z-9 | cyclopentyl |
| 100. | G-4 | Z-9 | cyclopentyl |
| 101. | G-5 | Z-9 | cyclopentyl |
| 102. | G-6 | Z-9 | cyclopentyl |
| 103. | G-1 | Z-9 | cyclohexyl |
| 104. | G-2 | Z-9 | cyclohexyl |
| 105. | G-3 | Z-9 | cyclohexyl |
| 106. | G-4 | Z-9 | cyclohexyl |
| 107. | G-5 | Z-9 | cyclohexyl |
| 108. | G-6 | Z-9 | cyclohexyl |
| 109. | G-1 | Z-10 | cyclopentyl |
| 110. | G-2 | Z-10 | cyclopentyl |
| 111. | G-3 | Z-10 | cyclopentyl |
| 112. | G-4 | Z-10 | cyclopentyl |
| 113. | G-5 | Z-10 | cyclopentyl |
| 114. | G-6 | Z-10 | cyclopentyl |
| 115. | G-1 | Z-10 | cyclohexyl |
| 116. | G-2 | Z-10 | cyclohexyl |
| 117. | G-3 | Z-10 | cyclohexyl |
| 118. | G-4 | Z-10 | cyclohexyl |
| 119. | G-5 | Z-10 | cyclohexyl |

TABLE 1-continued

| | | | |
|---|---|---|---|
| 120. | G-6 | Z-10 | cyclohexyl |
| 121. | G-1 | Z-11 | cyclopentyl |
| 122. | G-2 | Z-11 | cyclopentyl |
| 123. | G-3 | Z-11 | cyclopentyl |
| 124. | G-4 | Z-11 | cyclopentyl |
| 125. | G-5 | Z-11 | cyclopentyl |
| 126. | G-6 | Z-11 | cyclopentyl |
| 127. | G-1 | Z-11 | cyclohexyl |
| 128. | G-2 | Z-11 | cyclohexyl |
| 129. | G-3 | Z-11 | cyclohexyl |
| 130. | G-4 | Z-11 | cyclohexyl |
| 131. | G-5 | Z-11 | cyclohexyl |
| 132. | G-6 | Z-11 | cyclohexyl |
| 133. | G-1 | Z-12 | cyclopentyl |
| 134. | G-2 | Z-12 | cyclopentyl |
| 135. | G-3 | Z-12 | cyclopentyl |
| 136. | G-4 | Z-12 | cyclopentyl |
| 137. | G-5 | Z-12 | cyclopentyl |
| 138. | G-6 | Z-12 | cyclopentyl |
| 139. | G-1 | Z-12 | cyclohexyl |
| 140. | G-2 | Z-12 | cyclohexyl |
| 141. | G-3 | Z-12 | cyclohexyl |
| 142. | G-4 | Z-12 | cyclohexyl |
| 143. | G-5 | Z-12 | cyclohexyl |
| 144. | G-6 | Z-12 | cyclohexyl |
| 145. | G-1 | Z-13 | cyclopentyl |
| 146. | G-2 | Z-13 | cyclopentyl |
| 147. | G-3 | Z-13 | cyclopentyl |
| 148. | G-4 | Z-13 | cyclopentyl |
| 149. | G-5 | Z-13 | cyclopentyl |
| 150. | G-6 | Z-13 | cyclopentyl |
| 151. | G-1 | Z-13 | cyclohexyl |
| 152. | G-2 | Z-13 | cyclohexyl |
| 153. | G-3 | Z-13 | cyclohexyl |
| 154. | G-4 | Z-13 | cyclohexyl |
| 155. | G-5 | Z-13 | cyclohexyl |
| 156. | G-6 | Z-13 | cyclohexyl |
| 157. | G-1 | Z-14 | cyclopentyl |
| 158. | G-2 | Z-14 | cyclopentyl |
| 159. | G-3 | Z-14 | cyclopentyl |
| 160. | G-4 | Z-14 | cyclopentyl |
| 161. | G-5 | Z-14 | cyclopentyl |
| 162. | G-6 | Z-14 | cyclopentyl |
| 163. | G-1 | Z-14 | cyclohexyl |
| 164. | G-2 | Z-14 | cyclohexyl |
| 165. | G-3 | Z-14 | cyclohexyl |
| 166. | G-4 | Z-14 | cyclohexyl |
| 167. | G-5 | Z-14 | cyclohexyl |
| 168. | G-6 | Z-14 | cyclohexyl |
| 169. | G-4 | Z-17 | cyclopentyl |
| 170. | G-6 | Z-17 | cyclopentyl |
| 171. | G-4 | Z-18 | cyclopentyl |
| 172. | G-6 | Z-18 | cyclopentyl |
| 173. | G-4 | Z-19 | cyclopentyl |
| 174. | G-6 | Z-19 | cyclopentyl |
| 175. | G-4 | Z-20 | cyclopentyl |
| 176. | G-6 | Z-20 | cyclopentyl |
| 177. | G-4 | Z-21 | cyclopentyl |
| 178. | G-6 | Z-21 | cyclopentyl |
| 179. | G-4 | Z-17 | cyclohexyl |
| 180. | G-6 | Z-17 | cyclohexyl |
| 181. | G-4 | Z-18 | cyclohexyl |
| 182. | G-6 | Z-18 | cyclohexyl |
| 183. | G-4 | Z-19 | cyclohexyl |
| 184. | G-6 | Z-19 | cyclohexyl |
| 185. | G-4 | Z-20 | cyclohexyl |
| 186. | G-6 | Z-20 | cyclohexyl |
| 187. | G-4 | Z-21 | cyclohexyl |
| 188. | G-6 | Z-21 | cyclohexyl |
| 189. | G-4 | Z-1 | carbomethoxy-cyclopentyl |
| 190. | G-4 | Z-2 | carbomethoxy-cyclopentyl |
| 191. | G-4 | Z-3 | carbomethoxy-cyclopentyl |
| 192. | G-4 | Z-6 | carbomethoxy-cyclopentyl |
| 193. | G-6 | Z-1 | carbomethoxy-cyclopentyl |
| 194. | G-6 | Z-2 | carbomethoxy-cyclopentyl |
| 195. | G-6 | Z-3 | carbomethoxy-cyclopentyl |
| 196. | G-6 | Z-6 | carbomethoxy-cyclopentyl |
| 197. | G-6 | Z-17 | carbomethoxy-cyclopentyl |
| 198. | G-6 | Z-18 | carbomethoxy-cyclopentyl |
| 199. | G-6 | Z-21 | carbomethoxy-cyclopentyl |
| 200. | G-4 | Z-1 | hydroxymethyl-cyclopentyl |
| 201. | G-4 | Z-2 | hydroxymethyl-cyclopentyl |
| 202. | G-4 | Z-3 | hydroxymethyl-cyclopentyl |
| 203. | G-4 | Z-6 | hydroxymethyl-cyclopentyl |
| 204. | G-6 | Z-1 | hydroxymethyl-cyclopentyl |
| 205. | G-6 | 1.2 | hydroxymethyl-cyclopentyl |
| 206. | G-6 | Z-3 | hydroxymethyl-cyclopentyl |
| 207. | G-6 | Z-6 | hydroxymethyl-cyclopentyl |
| 208. | G-6 | Z-17 | hydroxymethyl-cyclopentyl |
| 209. | G-6 | Z-18 | hydroxymethyl-cyclopentyl |
| 210. | G-6 | Z-21 | hydroxymethyl-cyclopentyl |
| 211. | G-4 | Z-1 | amino-cyclopentyl |
| 212. | G-4 | Z-2 | amino-cyclopentyl |
| 213. | G-4 | Z-3 | amino-cyclopentyl |
| 214. | G-4 | Z-6 | amino-cyclopentyl |
| 215. | G-6 | Z-1 | amino-cyclopentyl |
| 216. | G-6 | Z-2 | amino-cyclopentyl |
| 217. | G-6 | Z-3 | amino-cyclopentyl |
| 218. | G-6 | Z-6 | amino-cyclopentyl |
| 219. | G-4 | Z-1 | dimethylaminocarbonyl-cyclohexyl |
| 220. | G-4 | Z-2 | dimethylaminocarbonyl-cyclohexyl |
| 221. | G-4 | Z-3 | dimethylaminocarbonyl-cyclohexyl |
| 222. | G-4 | Z-6 | dimethylaminocarbonyl-cyclohexyl |
| 223. | G-4 | Z-17 | dimethylaminocarbonyl-cyclohexyl |
| 224. | GA | Z-18 | dimethylaminocarbonyl-cyclohexyl |
| 225. | G-4 | Z-21 | dimethylaminocarbonyl-cyclohexyl |
| 226. | G-4 | Z-1 | dimethylaminocarbonyl-cyclohexyl-A |
| 227. | G-4 | Z-2 | dimethylaminocarbonyl-cyclohexyl-A |
| 228. | G-4 | Z-3 | dimethylaminocarbonyl-cyclohexyl-A |
| 229. | G-4 | Z-6 | dimethylaminocarbonyl-cyclohexyl-A |
| 230. | G-4 | Z-17 | dimethylaminocarbonyl-cyclohexyl-A |
| 231. | G-4 | Z-18 | dimethylaminocarbonyl-cyclohexyl-A |
| 232. | G-4 | Z-21 | dimethylaminocarbonyl-cyclohexyl-A |
| 233. | G-4 | Z-1 | methoxy-cyclohexyl |
| 234. | G-4 | Z-2 | methoxy-cyclohexyl |
| 235. | G-4 | Z-3 | methoxy-cyclohexyl |
| 236. | G-4 | Z-6 | methoxy-cyclohexyl |
| 237. | G-4 | Z-17 | methoxy-cyclohexyl |
| 238. | G-4 | Z-18 | methoxy-cyclohexyl |
| 239. | G-4 | Z-21 | methoxy-cyclohexyl |
| 240. | G-4 | Z-1 | methoxy-cyclohexyl-A |
| 241. | G-4 | Z-2 | methoxy-cyclohexyl-A |
| 242. | G-4 | Z-3 | methoxy-cyclohexyl-A |
| 243. | G-4 | Z-6 | methoxy-cyclohexyl-A |
| 244. | G-4 | Z-17 | methoxy-cyclohexyl-A |
| 245. | G-4 | Z-18 | methoxy-cyclohexyl-A |
| 246. | G-4 | Z-21 | methoxy-cyclohexyl-A |
| 247. | G-6 | Z-1 | 1-methyl-pyrrolidine |
| 248. | G-5 | Z-1 | 1-methyl-pyrrolidine |
| 249. | G-1 | Z-1 | 1-methyl-pyrrolidine |
| 250. | G-2 | Z-1 | 1-methyl-pyrrolidine |
| 251. | G-3 | Z-1 | 1-methyl-pyrrolidine |
| 252. | G-4 | Z-1 | 1-methyl-pyrrolidine |
| 253. | G-8 | Z-1 | 1-methyl-pyrrolidine |
| 254. | G-6 | Z-2 | 1-methyl-pyrrolidine |
| 255. | G-5 | Z-2 | 1-methyl-pyrrolidine |
| 256. | G-1 | Z-2 | 1-methyl-pyrrolidine |
| 257. | G-2 | Z-2 | 1-methyl-pyrrolidine |
| 258. | G-3 | Z-2 | 1-methyl-pyrrolidine |
| 259. | G-4 | Z-2 | 1-methyl-pyrrolidine |
| 260. | G-8 | Z-2 | 1-methyl-pyrrolidine |
| 261. | G-6 | Z-6 | 1-methanesulfonyl-pyrrolidine |
| 262. | G-5 | Z-6 | 1-methanesulfonyl-pyrrolidine |
| 263. | G-1 | Z-6 | 1-methanesulfonyl-pyrrolidine |
| 264. | G-2 | Z-6 | 1-methanesulfonyl-pyrrolidine |
| 265. | G-3 | Z-6 | 1-methanesulfonyl-pyrrolidine |
| 266. | G-4 | Z-6 | 1-methanesulfonyl-pyrrolidine |
| 267. | G-8 | Z-6 | 1-methanesulfonyl-pyrrolidine |
| 268. | G-6 | Z-17 | 1-methanesulfonyl-pyrrolidine |
| 269. | G-6 | Z-18 | 1-methanesulfonyl-pyrrolidine |
| 270. | G-4 | Z-1 | 1-carbomethoxy-pyrrolidine |
| 271. | G-4 | Z-2 | 1-carbomethoxy-pyrrolidine |
| 272. | G-4 | Z-3 | 1-carbomethoxy-pyrrolidine |
| 273. | G-4 | Z-6 | 1-carbomethoxy-pyrrolidine |
| 274. | G-6 | Z-1 | 1-carbomethoxy-pyrrolidine |
| 275. | G-6 | Z-2 | 1-carbomethoxy-pyrrolidine |
| 276. | G-6 | Z-3 | 1-carbomethoxy-pyrrolidine |
| 277. | G-6 | Z-6 | 1-carbomethoxy-pyrrolidine |

TABLE 1-continued

| | | | |
|---|---|---|---|
| 278. | G-8 | Z-1 | 1-carbomethoxy-pyrrolidine |
| 279. | G-8 | Z-2 | 1-carbomethoxy-pyrrolidine |
| 280. | G-8 | Z-3 | 1-carbomethoxy-pyrrolidine |
| 281. | G-8 | Z-6 | 1-carbomethoxy-pyrrolidine |
| 282. | G-4 | Z-1 | 1-dimethylaminocarbonyl-pyrrolidine |
| 283. | G-4 | Z-2 | 1-dimethylaminocarbonyl-pyrrolidine |
| 284. | G-4 | Z-3 | 1-dimethylaminocarbonyl-pyrrolidine |
| 285. | G-4 | Z-6 | 1-dimethylaminocarbonyl-pyrrolidine |
| 286. | G-6 | Z-1 | 1-dimethylaminocarbonyl-pyrrolidine |
| 287. | G-6 | Z-2 | 1-dimethylaminocarbonyl-pyrrolidine |
| 288. | G-6 | Z-3 | 1-dimethylaminocarbonyl-pyrrolidine |
| 289. | G-6 | Z-6 | 1-dimethylaminocarbonyl-pyrrolidine |
| 290. | G-6 | Z-17 | 1-dimethylaminocarbonyl-pyrrolidine |
| 291. | G-6 | Z-18 | 1-dimethylaminocarbonyl-pyrrolidine |
| 292. | G-6 | Z-1 | 1-acetyl-pyrrolidine |
| 293. | G-6 | Z-2 | 1-acetyl-pyrrolidine |
| 294. | G-6 | Z-3 | 1-acetyl-pyrrolidine |
| 295. | G-6 | Z-6 | 1-acetyl-pyrrolidine |
| 296. | G-6 | Z-17 | 1-acetyl-pyrrolidine |
| 297. | G-6 | Z-18 | 1-acetyl-pyrrolidine |
| 298. | G-6 | Z-1 | tetrahydrofuran |
| 299. | G-5 | Z-1 | tetrahydrofuran |
| 300. | G-1 | Z-2 | tetrahydrofuran |
| 301. | G-2 | Z-1 | tetrahydrofuran |
| 302. | G-3 | Z-1 | tetrahydrofuran |
| 303. | G-4 | Z-1 | tetrahydrofuran |
| 304. | G-7 | Z-1 | tetrahydrofuran |
| 305. | G-8 | Z-1 | tetrahydrofuran |
| 306. | G-6 | Z-2 | tetrahydrofuran |
| 307. | G-5 | Z-2 | tetrahydrofuran |
| 308. | G-1 | Z-2 | tetrahydrofuran |
| 309. | G-2 | Z-2 | tetrahydrofuran |
| 310. | G-3 | Z-2 | tetrahydrofuran |
| 311. | G-4 | Z-2 | tetrahydrofuran |
| 312. | G-7 | Z-2 | tetrahydrofuran |
| 313. | G-8 | Z-2 | tetrahydrofuran |
| 314. | G-6 | Z-3 | tetrahydrofuran |
| 315. | G-5 | Z-3 | tetrahydrofuran |
| 316. | G-1 | Z-3 | tetrahydrofuran |
| 317. | G-2 | Z-3 | tetrahydrofuran |
| 318. | G-3 | Z-3 | tetrahydrofuran |
| 319. | G-4 | Z-3 | tetrahydrofuran |
| 320. | Z-3 | G-7 | tetrahydrofuran |
| 321. | G-8 | Z-3 | tetrahydrofuran |
| 322. | G-6 | Z-4 | tetrahydrofuran |
| 323. | G-5 | Z-4 | tetrahydrofuran |
| 324. | G-1 | Z-4 | tetrahydrofuran |
| 325. | G-2 | Z-4 | tetrahydrofuran |
| 326. | G-3 | Z-4 | tetrahydrofuran |
| 327. | G-4 | Z-4 | tetrahydrofuran |
| 328. | G-7 | Z-4 | tetrahydrofuran |
| 329. | G-8 | Z-4 | tetrahydrofuran |
| 330. | G-6 | Z-5 | tetrahydrofuran |
| 331. | G-5 | Z-5 | tetrahydrofuran |
| 332. | G-1 | Z-5 | tetrahydrofuran |
| 333. | G-2 | Z-5 | tetrahydrofuran |
| 334. | G-3 | Z-5 | tetrahydrofuran |
| 335. | G-4 | Z-5 | tetrahydrofuran |
| 336. | G-7 | Z-5 | tetrahydrofuran |
| 337. | G-8 | Z-5 | tetrahydrofuran |
| 338. | G-6 | Z-6 | tetrahydrofuran |
| 339. | G-5 | Z-6 | tetrahydrofuran |
| 340. | G-1 | Z-6 | tetrahydrofuran |
| 341. | G-2 | Z-6 | tetrahydrofuran |
| 342. | G-3 | Z-6 | tetrahydrofuran |
| 343. | G-4 | Z-6 | tetrahydrofuran |
| 344. | G-7 | Z-6 | tetrahydrofuran |
| 345. | G-8 | Z-6 | tetrahydrofuran |
| 346. | G-6 | Z-7 | tetrahydrofuran |
| 347. | G-5 | Z-7 | tetrahydrofuran |
| 348. | G-1 | Z-7 | tetrahydrofuran |
| 349. | G-2 | Z-7 | tetrahydrofuran |
| 350. | G-3 | Z-7 | tetrahydrofuran |
| 351. | G-4 | Z-7 | tetrahydrofuran |
| 352. | G-7 | Z-7 | tetrahydrofuran |
| 353. | G-8 | Z-7 | tetrahydrofuran |
| 354. | G-6 | Z-8 | tetrahydrofuran |
| 355. | G-5 | Z-8 | tetrahydrofuran |
| 356. | G-1 | Z-8 | tetrahydrofuran |
| 357. | G-2 | Z-8 | tetrahydrofuran |
| 358. | G-3 | Z-8 | tetrahydrofuran |
| 359. | G-4 | Z-8 | tetrahydrofuran |
| 360. | G-8 | Z-8 | tetrahydrofuran |
| 361. | G-6 | Z-11 | tetrahydrofuran |
| 362. | G-5 | Z-11 | tetrahydrofuran |
| 363. | G-1 | Z-11 | tetrahydrofuran |
| 364. | G-2 | Z-11 | tetrahydrofuran |
| 365. | G-3 | Z-11 | tetrahydrofuran |
| 366. | G-4 | Z-11 | tetrahydrofuran |
| 367. | G-8 | Z-11 | tetrahydrofuran |
| 368. | G-6 | Z-12 | tetrahydrofuran |
| 369. | G-5 | Z-12 | tetrahydrofuran |
| 370. | G-1 | Z-12 | tetrahydrofuran |
| 371. | G-2 | Z-12 | tetrahydrofuran |
| 372. | G-3 | Z-12 | tetrahydrofuran |
| 373. | G-4 | Z-12 | tetrahydrofuran |
| 374. | G-8 | Z-12 | tetrahydrofuran |
| 375. | G-6 | Z-13 | tetrahydrofuran |
| 376. | G-5 | Z-13 | tetrahydrofuran |
| 377. | G-1 | Z-13 | tetrahydrofuran |
| 378. | G-2 | Z-13 | tetrahydrofuran |
| 379. | G-3 | Z-13 | tetrahydrofuran |
| 380. | G-4 | Z-13 | tetrahydrofuran |
| 381. | G-8 | Z-13 | tetrahydrofuran |
| 382. | G-6 | Z-13 | tetrahydrofuran-A |
| 383. | G-5 | Z-13 | tetrahydrofuran-A |
| 384. | G-1 | Z-13 | tetrahydrofuran |
| 385. | G-2 | Z-13 | tetrahydrofuran |
| 386. | G-3 | Z-13 | tetrahydrofuran |
| 387. | G-4 | Z-13 | tetrahydrofuran |
| 388. | G-8 | Z-13 | tetrahydrofuran |
| 389. | G-6 | Z-17 | tetrahydrofuran |
| 390. | G-6 | Z-18 | tetrahydrofuran |
| 391. | G-6 | Z-19 | tetrahydrofuran |
| 392. | G-6 | Z-21 | tetrahydrofuran |
| 393. | G-6 | Z-1 | tetrahydrofuran-A |
| 394. | G-5 | Z-1 | tetrahydrofuran-A |
| 395. | G-1 | Z-2 | tetrahydrofuran-A |
| 396. | G-2 | Z-1 | tetrahydrofuran-A |
| 397. | G-3 | Z-1 | tetrahydrofuran-A |
| 398. | G-4 | Z-1 | tetrahydrofuran-A |
| 399. | G-8 | Z-1 | tetrahydrofuran-A |
| 400. | G-6 | Z-2 | tetrahydrofuran-A |
| 401. | G-5 | Z-2 | tetrahydrofuran-A |
| 402. | G-1 | Z-2 | tetrahydrofuran-A |
| 403. | G-2 | Z-2 | tetrahydrofuran-A |
| 404. | G-3 | Z-2 | tetrahydrofuran-A |
| 405. | G-4 | Z-2 | tetrahydrofuran-A |
| 406. | G-7 | Z-2 | tetrahydrofuran-A |
| 407. | G-8 | Z-2 | tetrahydrofuran-A |
| 408. | G-6 | Z-3 | tetrahydrofuran-A |
| 409. | G-5 | Z-3 | tetrahydrofuran-A |
| 410. | G-1 | Z-3 | tetrahydrofuran-A |
| 411. | G-2 | Z-3 | tetrahydrofuran-A |
| 412. | G-3 | Z-3 | tetrahydrofuran-A |
| 413. | G-4 | Z-3 | tetrahydrofuran-A |
| 414. | G-7 | Z-3 | tetrahydrofuran-A |
| 415. | G-8 | Z-3 | tetrahydrofuran-A |
| 416. | G-6 | Z-4 | tetrahydrofuran-A |
| 417. | G-5 | Z-4 | tetrahydrofuran-A |
| 418. | G-1 | Z-4 | tetrahydrofuran-A |
| 419. | G-2 | Z-4 | tetrahydrofuran-A |
| 420. | G-3 | Z-4 | tetrahydrofuran-A |
| 421. | G-4 | Z-4 | tetrahydrofuran-A |
| 422. | G-7 | Z-4 | tetrahydrofuran-A |
| 423. | G-8 | Z-4 | tetrahydrofuran-A |
| 424. | G-6 | Z-5 | tetrahydrofuran-A |
| 425. | G-5 | Z-5 | tetrahydrofuran-A |
| 426. | G-1 | Z-5 | tetrahydrofuran-A |
| 427. | G-2 | Z-5 | tetrahydrofuran-A |
| 428. | G-3 | Z-5 | tetrahydrofuran-A |
| 429. | G-4 | Z-5 | tetrahydrofuran-A |
| 430. | G-7 | Z-5 | tetrahydrofuran-A |
| 431. | G-8 | Z-5 | tetrahydrofuran-A |
| 432. | G-6 | Z-6 | tetrahydrofuran-A |
| 433. | G-5 | Z-6 | tetrahydrofuran-A |
| 434. | G-1 | Z-6 | tetrahydrofuran-A |
| 435. | G-2 | Z-6 | tetrahydrofuran-A |

TABLE 1-continued

| | | | |
|---|---|---|---|
| 436. | G-3 | Z-6 | tetrahydrofuran-A |
| 437. | G-4 | Z-6 | tetrahydrofuran-A |
| 438. | G-7 | Z-6 | tetrahydrofuran-A |
| 439. | G-8 | Z-6 | tetrahydrofuran-A |
| 440. | G-6 | Z-7 | tetrahydrofuran-A |
| 441. | G-5 | Z-7 | tetrahydrofuran-A |
| 442. | G-1 | Z-7 | tetrahydrofuran-A |
| 443. | G-2 | Z-7 | tetrahydrofuran-A |
| 444. | G-3 | Z-7 | tetrahydrofuran-A |
| 445. | G-4 | Z-7 | tetrahydrofuran-A |
| 446. | G-7 | Z-7 | tetrahydrofuran-A |
| 447. | G-8 | Z-7 | tetrahydrofuran-A |
| 448. | G-6 | Z-8 | tetrahydrofuran-A |
| 449. | G-5 | Z-8 | tetrahydrofuran-A |
| 450. | G-1 | Z-8 | tetrahydrofuran-A |
| 451. | G-2 | Z-8 | tetrahydrofuran-A |
| 452. | G-3 | Z-8 | tetrahydrofuran-A |
| 453. | G-4 | Z-8 | tetrahydrofuran-A |
| 454. | G-8 | Z-8 | tetrahydrofuran-A |
| 455. | G-6 | Z-11 | tetrahydrofuran-A |
| 456. | G-5 | Z-11 | tetrahydrofuran-A |
| 457. | G-1 | Z-11 | tetrahydrofuran-A |
| 458. | G-2 | Z-11 | tetrahydrofuran-A |
| 459. | G-3 | Z-11 | tetrahydrofuran-A |
| 460. | G-4 | Z-11 | tetrahydrofuran-A |
| 461. | G-8 | Z-11 | tetrahydrofuran-A |
| 462. | G-6 | Z-12 | tetrahydrofuran-A |
| 463. | G-5 | Z-12 | tetrahydrofuran-A |
| 464. | G-1 | Z-12 | tetrahydrofuran-A |
| 465. | G-2 | Z-12 | tetrahydrofuran-A |
| 466. | G-3 | Z-12 | tetrahydrofuran-A |
| 467. | G-4 | Z-12 | tetrahydrofuran-A |
| 468. | G-8 | Z-12 | tetrahydrofuran-A |
| 469. | G-6 | Z-13 | tetrahydrofuran-A |
| 470. | G-5 | Z-13 | tetrahydrofuran-A |
| 471. | G-1 | Z-13 | tetrahydrofuran-A |
| 472. | G-2 | Z-13 | tetrahydrofuran-A |
| 473. | G-3 | Z-13 | tetrahydrofuran-A |
| 474. | G-4 | Z-13 | tetrahydrofuran-A |
| 475. | G-8 | Z-13 | tetrahydrofuran-A |
| 476. | G-6 | Z-17 | tetrahydrofuran-A |
| 477. | G-6 | Z-18 | tetrahydrofuran-A |
| 478. | G-6 | Z-19 | tetrahydrofuran-A |
| 479. | G-6 | Z-21 | tetrahydrofuran-A |
| 480. | G-6 | Z-6 | tetrahydrothiophenyl-dioxide |
| 481. | G-5 | Z-6 | tetrahydrothiophenyl-dioxide |
| 482. | G-1 | Z-6 | tetrahydrothiophenyl-dioxide |
| 483. | G-2 | Z-6 | tetrahydrothiophenyl-dioxide |
| 484. | G-3 | Z-6 | tetrahydrothiophenyl-dioxide |
| 485. | G-4 | Z-6 | tetrahydrothiophenyl-dioxide |
| 486. | G-8 | Z-6 | tetrahydrothiophenyl-dioxide |
| 487. | G-6 | Z-1 | tetrahydrothiophenyl-dioxide |
| 488. | G-5 | Z-1 | tetrahydrothiophenyl-dioxide |
| 489. | G-1 | Z-1 | tetrahydrothiophenyl-dioxide |
| 490. | G-2 | Z-1 | tetrahydrothiophenyl-dioxide |
| 491. | G-3 | Z-1 | tetrahydrothiophenyl-dioxide |
| 492. | G-4 | Z-1 | tetrahydrothiophenyl-dioxide |
| 493. | G-8 | Z-1 | tetrahydrothiophenyl-dioxide |
| 494. | G-4 | Z-17 | tetrahydrothiophenyl-dioxide |
| 495. | G-4 | Z-18 | tetrahydrothiophenyl-dioxide |
| 496. | G-4 | Z-21 | tetrahydrothiophenyl-dioxide |
| 497. | G-6 | Z-1 | indane |
| 498. | G-5 | Z-1 | indane |
| 499. | G-1 | Z-1 | indane |
| 500. | G-2 | Z-1 | indane |
| 501. | G-3 | Z-1 | indane |
| 502. | G-4 | Z-1 | indane |
| 503. | G-8 | Z-1 | indane |
| 504. | G-6 | Z-2 | indane |
| 505. | G-5 | Z-2 | indane |
| 506. | G-1 | Z-2 | indane |
| 507. | G-2 | Z-2 | indane |
| 508. | G-3 | Z-2 | indane |
| 509. | G-4 | Z-2 | indane |
| 510. | G-8 | Z-2 | indane |
| 511. | G-6 | Z-3 | indane |
| 512. | G-5 | Z-3 | indane |
| 513. | G-1 | Z-3 | indane |
| 514. | G-2 | Z-3 | indane |
| 515. | G-3 | Z-3 | indane |
| 516. | G-4 | Z-3 | indane |
| 517. | G-8 | Z-3 | indane |
| 518. | G-6 | Z-6 | indane |
| 519. | G-5 | Z-6 | indane |
| 520. | G-1 | Z-6 | indane |
| 521. | G-2 | Z-6 | indane |
| 522. | G-3 | Z-6 | indane |
| 523. | G-4 | Z-6 | indane |
| 524. | G-8 | Z-6 | indane |
| 525. | G-6 | Z-11 | indane |
| 526. | G-5 | Z-11 | indane |
| 527. | G-1 | Z-11 | indane |
| 528. | G-2 | Z-11 | indane |
| 529. | G-3 | Z-11 | indane |
| 530. | G-4 | Z-11 | indane |
| 531. | G-8 | Z-11 | indane |
| 532. | G-6 | Z-12 | indane |
| 533. | G-5 | Z-12 | indane |
| 534. | G-1 | Z-12 | indane |
| 535. | G-2 | Z-12 | indane |
| 536. | G-3 | Z-12 | indane |
| 537. | G-4 | Z-12 | indane |
| 538. | G-8 | Z-12 | indane |
| 539. | G-6 | Z-13 | indane |
| 540. | G-5 | Z-13 | indane |
| 541. | G-1 | Z-13 | indane |
| 542. | G-2 | Z-13 | indane |
| 543. | G-3 | Z-13 | indane |
| 544. | G-4 | Z-13 | indane |
| 545. | G-8 | Z-13 | indane |
| 546. | G-4 | Z-18 | indane |
| 547. | G-4 | Z-18 | indane |
| 548. | G-6 | Z-18 | indane |
| 549. | G-6 | Z-18 | indane |
| 550. | G-4 | Z-1 | indane-A |
| 551. | G-4 | Z-2 | indane-A |
| 552. | G-4 | Z-3 | indane-A |
| 553. | G-4 | Z-6 | indane-A |
| 554. | G-6 | Z-1 | indane-A |
| 555. | G-6 | Z-2 | indane-A |
| 556. | G-6 | Z-3 | indane-A |
| 557. | G-6 | Z-6 | indane-A |
| 558. | G-8 | Z-1 | indane-A |
| 559. | G-8 | Z-2 | indane-A |
| 560. | G-8 | Z-3 | indane-A |
| 561. | G-8 | Z-6 | indane-A |
| 562. | G-4 | Z-18 | indane-A |
| 563. | G-4 | Z-18 | indane-A |
| 564. | G-6 | Z-18 | indane-A |
| 565. | G-6 | Z-18 | indane-A |
| 566. | G-6 | Z-1 | 1-oxa-spiro[4.4]non-7-yl |
| 567. | G-5 | Z-1 | 1-oxa-spiro[4.4]non-7-yl |
| 568. | G-1 | Z-1 | 1-oxa-spiro[4.4]non-7-yl |
| 569. | G-2 | Z-1 | 1-oxa-spiro[4.4]non-7-yl |
| 570. | G-3 | Z-1 | 1-oxa-spiro[4.4]non-7-yl |
| 571. | G-4 | Z-1 | 1-oxa-spiro[4.4]non-7-yL |
| 572. | G-8 | Z-1 | 1-oxa-spiro[4.4]non-7-yl |
| 573. | G-6 | Z-2 | 1-oxa-spiro[4.4]non-7-yl |
| 574. | G-5 | Z-2 | 1-oxa-spiro[4.4]non-7-yl |
| 575. | G-1 | Z-2 | 1-oxa-spiro[4.4]non-7-yl |
| 576. | G-2 | Z-2 | 1-oxa-spiro[4.4]non-7-yl |
| 577. | G-3 | Z-2 | 1-oxa-spiro[4.4]non-7-yl |
| 578. | G-4 | Z-2 | 1-oxa-spiro[4.4]non-7-yl |
| 579. | G-8 | Z-2 | 1-oxa-spiro[4.4]non-7-yl |
| 580. | G-6 | Z-3 | 1-oxa-spiro[4.4]non-7-yl |
| 581. | G-5 | Z-3 | 1-oxa-spiro[4.4]non-7-yl |
| 582. | G-1 | Z-3 | 1-oxa-spiro[4.4]non-7-yl |
| 583. | G-2 | Z-3 | 1-oxa-spiro[4.4]non-7-yl |
| 584. | G-3 | Z-3 | 1-oxa-spiro[4.4]non-7-yl |
| 585. | G-4 | Z-3 | 1-oxa-spiro[4.4]non-7-yl |
| 586. | G-8 | Z-3 | 1-oxa-spiro[4.4]non-7-yl |
| 587. | G-6 | Z-6 | 1-oxa-spiro[4.4]non-7-yl |
| 588. | G-5 | Z-6 | 1-oxa-spiro[4.4]non-7-yl |
| 589. | G-1 | Z-6 | 1-oxa-spiro[4.4]non-7-yl |
| 590. | G-2 | Z-6 | 1-oxa-spiro[4.4]non-7-yl |
| 591. | G-3 | Z-6 | 1-oxa-spiro[4.4]non-7-yl |
| 592. | G-4 | Z-6 | 1-oxa-spiro[4.4]non-7-yl |
| 593. | G-8 | Z-6 | 1-oxa-spiro[4.4]non-7-yl |

TABLE 1-continued

| | | | |
|---|---|---|---|
| 594. | G-6 | Z-11 | 1-oxa-spiro[4.4]non-7-yl |
| 595. | G-5 | Z-11 | 1-oxa-spiro[4.4]non-7-yl |
| 596. | G-1 | Z-11 | 1-oxa-spiro[4.4]non-7-yl |
| 597. | G-2 | Z-11 | 1-oxa-spiro[4.4]non-7-yl |
| 598. | G-3 | Z-11 | 1-oxa-spiro[4.4]non-7-yl |
| 599. | G-4 | Z-11 | 1-oxa-spiro[4.4]non-7-yl |
| 600. | G-6 | Z-12 | 1-oxa-spiro[4.4]non-7-yl |
| 601. | G-5 | Z-12 | 1-oxa-spiro[4.4]non-7-yl |
| 602. | G-1 | Z-12 | 1-oxa-spiro[4.4]non-7-yl |
| 603. | G-2 | Z-12 | 1-oxa-spiro[4.4]non-7-yl |
| 604. | G-3 | Z-12 | 1-oxa-spiro[4.4]non-7-yl |
| 605. | G-4 | Z-12 | 1-oxa-spiro[4.4]non-7-y1 |
| 606. | G-6 | Z-13 | 1-oxa-spiro[4.4]non-7-yl |
| 607. | G-5 | Z-13 | 1-oxa-spiro[4.4]non-7-yl |
| 608. | G-1 | Z-13 | 1-oxa-spiro[4.4]non-7-yl |
| 609. | G-2 | Z-13 | 1-oxa-spiro[4.4]non-7-yl |
| 610. | G-3 | Z-13 | 1-oxa-spiro[4.4]non-7-yl |
| 611. | G-4 | Z-13 | 1-oxa-spiro[4.4]non-7-yl |
| 612. | G-4 | Z-17 | 1-oxa-spiro[4.4]non-7-yl |
| 613. | G-4 | Z-18 | 1-oxa-spiro[4.4]non-7-yl |
| 614. | G-4 | Z-19 | 1-oxa-spiro[4.4]non-7-yl |
| 615. | G-6 | Z-1 | tetrahydropyran |
| 616. | G-5 | Z-1 | tetrahydropyran |
| 617. | G-1 | Z-1 | tetrahydropyran |
| 618. | G-2 | Z-1 | tetrahydropyran |
| 619. | G-3 | Z-1 | tetrahydropyran |
| 620. | G-8 | Z-1 | tetrahydropyran |
| 621. | G-4 | Z-1 | tetrahydropyran |
| 622. | G-6 | Z-2 | tetrahydropyran |
| 623. | G-5 | Z-2 | tetrahydropyran |
| 624. | G-1 | Z-2 | tetrahydropyran |
| 625. | G-2 | Z-2 | tetrahydropyran |
| 626. | G-3 | Z-2 | tetrahydropyran |
| 627. | G-8 | Z-2 | tetrahydropyran |
| 628. | G-4 | Z-2 | tetrahydropyran |
| 629. | G-6 | Z-3 | tetrahydropyran |
| 630. | G-5 | Z-3 | tetrahydropyran |
| 631. | G-1 | Z-3 | tetrahydropyran |
| 632. | G-2 | Z-3 | tetrahydropyran |
| 633. | G-3 | Z-3 | tetrahydropyran |
| 634. | G-8 | Z-3 | tetrahydropyran |
| 635. | G-4 | Z-3 | tetrahydropyran |
| 636. | G-6 | Z-11 | tetrahydropyran |
| 637. | G-5 | Z-11 | tetrahydropyran |
| 638. | G-1 | Z-11 | tetrahydropyran |
| 639. | G-2 | Z-11 | tetrahydropyran |
| 640. | G-3 | Z-11 | tetrahydropyran |
| 641. | G-8 | Z-11 | tetrahydropyran |
| 642. | G-4 | Z-11 | tetrahydropyran |
| 643. | G-6 | Z-12 | tetrahydropyran |
| 644. | G-5 | Z-12 | tetrahydropyran |
| 645. | G-1 | Z-12 | tetrahydropyran |
| 646. | G-2 | Z-12 | tetrahydropyran |
| 647. | G-3 | Z-12 | tetrahydropyran |
| 648. | G-8 | Z-12 | tetrahydropyran |
| 649. | G-4 | Z-12 | tetrahydropyran |
| 650. | G-6 | Z-13 | tetrahydropyran |
| 651. | G-5 | Z-13 | tetrahydropyran |
| 652. | G-1 | Z-13 | tetrahydropyran |
| 653. | G-2 | Z-13 | tetrahydropyran |
| 654. | G-3 | Z-13 | tetrahydropyran |
| 655. | G-8 | Z-13 | tetrahydropyran |
| 656. | G-4 | Z-13 | tetrahydropyran |
| 657. | G-6 | Z-6 | tetrahydropyran |
| 658. | G-5 | Z-6 | tetrahydropyran |
| 659. | G-1 | Z-6 | tetrahydropyran |
| 660. | G-2 | Z-6 | tetrahydropyran |
| 661. | G-3 | Z-6 | tetrahydropyran |
| 662. | G-8 | Z-6 | tetrahydropyran |
| 663. | G-4 | Z-6 | tetrahydropyran |
| 664. | G-4 | Z-17 | tetrahydropyran |
| 665. | G-4 | Z-18 | tetrahydropyran |
| 666. | G-4 | Z-19 | tetrahydropyran |
| 667. | G-6 | Z-1 | tetrahydropyran-A |
| 668. | G-5 | Z-1 | tetrahydropyran-A |
| 669. | G-1 | Z-1 | tetrahydropyran-A |
| 670. | G-2 | Z-1 | tetrahydropyran-A |
| 671. | G-3 | Z-1 | tetrahydropyran-A |
| 672. | G-8 | Z-1 | tetrahydropyran-A |
| 673. | G-4 | Z-1 | tetrahydropyran-A |
| 674. | G-6 | Z-2 | tetrahydropyran-A |
| 675. | G-5 | Z-2 | tetrahydropyran-A |
| 676. | G-1 | Z-2 | tetrahydropyran-A |
| 677. | G-2 | Z-2 | tetrahydropyran-A |
| 678. | G-3 | Z-2 | tetrahydropyran-A |
| 679. | G-8 | Z-2 | tetrahydropyran-A |
| 680. | G-4 | Z-2 | tetrahydropyran-A |
| 681. | G-6 | Z-3 | tetrahydropyran-A |
| 682. | G-5 | Z-3 | tetrahydropyran-A |
| 683. | G-1 | Z-3 | tetrahydropyran-A |
| 684. | G-2 | Z-3 | tetrahydropyran-A |
| 685. | G-3 | Z-3 | tetrahydropyran-A |
| 686. | G-8 | Z-3 | tetrahydropyran-A |
| 687. | G-4 | Z-3 | tetrahydropyran-A |
| 688. | G-6 | Z-11 | tetrahydropyran-A |
| 689. | G-5 | Z-11 | tetrahydropyran-A |
| 690. | G-1 | Z-11 | tetrahydropyran-A |
| 691. | G-2 | Z-11 | tetrahydropyran-A |
| 692. | G-3 | Z-11 | tetrahydropyran-A |
| 693. | G-8 | Z-11 | tetrahydropyran-A |
| 694. | G-4 | Z-11 | tetrahydropyran-A |
| 695. | G-6 | Z-12 | tetrahydropyran-A |
| 696. | G-5 | Z-12 | tetrahydropyran-A |
| 697. | G-1 | Z-12 | tetrahydropyran-A |
| 698. | G-2 | Z-12 | tetrahydro yran-A |
| 699. | G-3 | Z-12 | tetrahydropyran-A |
| 700. | G-8 | Z-12 | tetrahydropyran-A |
| 701. | G-4 | Z-12 | tetrahydropyran-A |
| 702. | G-6 | Z-13 | tetrahydropyran-A |
| 703. | G-5 | Z-13 | tetrahydropyran-A |
| 704. | G-1 | Z-13 | tetrahydropyran-A |
| 705. | G-2 | Z-13 | tetrahydropyran-A |
| 706. | G-3 | Z-13 | tetrahydropyran-A |
| 707. | G-8 | Z-13 | tetrahydropyran-A |
| 708. | G-4 | Z-13 | tetrahydropyran-A |
| 709. | G-6 | Z-6 | tetrahydropyran-A |
| 710. | G-5 | Z-6 | tetrahydropyran-A |
| 711. | G-1 | Z-6 | tetrahydropyran-A |
| 712. | G-2 | Z-6 | tetrahydropyran-A |
| 713. | G-3 | Z-6 | tetrahydropyran-A |
| 714. | G-8 | Z-6 | tetrahydropyran-A |
| 715. | G-4 | Z-6 | tetrahydropyran-A |
| 716. | G-4 | Z-17 | tetrahydropyran-A |
| 717. | G-4 | Z-18 | tetrahydropyran-A |
| 718. | G-4 | Z-19 | tetrahydropyran-A |
| 719. | G-6 | Z-1 | tetrahydropyran-B |
| 720. | G-5 | Z-1 | tetrahydropyran-B |
| 721. | G-1 | Z-1 | tetrahydropyran-B |
| 722. | G-2 | Z-1 | tetrahydropyran-B |
| 723. | G-3 | Z-1 | tetrahydropyran-B |
| 724. | G-8 | Z-1 | tetrahydropyran-B |
| 725. | G-4 | Z-1 | tetrahydropyran-B |
| 726. | G-6 | Z-2 | tetrahydropyran-B |
| 727. | G-5 | Z-2 | tetrahydropyran-B |
| 728. | G-1 | Z-2 | tetrahydropyran-B |
| 729. | G-2 | Z-2 | tetrahydropyran-B |
| 730. | G-3 | Z-2 | tetrahydropyran-B |
| 731. | G-8 | Z-2 | tetrahydropyran-B |
| 732. | G-4 | Z-2 | tetrahydropyran-B |
| 733. | G-6 | Z-3 | tetrahydropyran-B |
| 734. | G-5 | Z-3 | tetrahydropyran-B |
| 735. | G-1 | Z-3 | tetrahydropyran-B |
| 736. | G-2 | Z-3 | tetrahydropyran-B |
| 737. | G-3 | Z-3 | tetrahydropyran-B |
| 738. | G-8 | Z-3 | tetrahydropyran-B |
| 739. | G-4 | Z-3 | tetrahydropyran-B |
| 740. | G-6 | Z-11 | tetrahydropyran-B |
| 741. | G-5 | Z-11 | tetrahydropyran-B |
| 742. | G-1 | Z-11 | tetrahydropyran-B |
| 743. | G-2 | Z-11 | tetrahydropyran-B |
| 744. | G-3 | Z-11 | tetrahydropyran-B |
| 745. | G-8 | Z-11 | tetrahydropyran-B |
| 746. | G-4 | Z-11 | tetrahydropyran-B |
| 747. | G-6 | Z-12 | tetrahydropyran-B |
| 748. | G-5 | Z-12 | tetrahydropyran-B |
| 749. | G-1 | Z-12 | tetrahydropyran-B |
| 750. | G-2 | Z-12 | tetrahydropyran-B |
| 751. | G-3 | Z-12 | tetrahydropyran-B |

TABLE 1-continued

| | | | |
|---|---|---|---|
| 752. | G-8 | Z-12 | tetrahydropyran-B |
| 753. | G-4 | Z-12 | tetrahydropyran-B |
| 754. | G-6 | Z-13 | tetrahydropyran-B |
| 755. | G-5 | Z-13 | tetrahydropyran-B |
| 756. | G-1 | Z-13 | tetrahydropyran-B |
| 757. | G-2 | Z-13 | tetrahydropyran-B |
| 758. | G-3 | Z-13 | tetrahydropyran-B |
| 759. | G-8 | Z-13 | tetrahydropyran-B |
| 760. | G-4 | Z-13 | tetrahydropyran-B |
| 761. | G-6 | Z-6 | tetrahydropyran-B |
| 762. | G-5 | Z-6 | tetrahydropyran-B |
| 763. | G-1 | Z-6 | tetrahydropyran-B |
| 764. | G-2 | Z-6 | tetrahydropyran-B |
| 765. | G-3 | Z-6 | tetrahydropyran-B |
| 766. | G-8 | Z-6 | tetrahydropyran-B |
| 767. | G-4 | Z-6 | tetrahydropyran-B |
| 768. | G-4 | Z-17 | tetrahydropyran-B |
| 769. | G-4 | Z-18 | tetrahydropyran-B |
| 770. | G-4 | Z-19 | tetrahydropyran-B |
| 771. | G-6 | Z-1 | 1-methyl-piperidine |
| 772. | G-5 | Z-1 | 1-methyl-piperidine |
| 773. | G-1 | Z-1 | 1-methyl-piperidine |
| 774. | G-2 | Z-1 | 1-methyl-piperidine |
| 775. | G-3 | Z-1 | 1-methyl-piperidine |
| 776. | G-8 | Z-1 | 1-methyl-piperidine |
| 777. | G-4 | Z-1 | 1-methyl-piperidine |
| 778. | G-6 | Z-2 | 1-methyl-piperidine |
| 779. | G-5 | Z-2 | 1-methyl-piperidine |
| 780. | G-1 | Z-2 | 1-methyl-piperidine |
| 781. | G-2 | Z-2 | 1-methyl-piperidine |
| 782. | G-3 | Z-2 | 1-methyl-piperidine |
| 783. | G-8 | Z-2 | 1-methyl-piperidine |
| 784. | G-4 | Z-2 | 1-methyl-piperidine |
| 785. | G-6 | Z-3 | 1-methyl-piperidine |
| 786. | G-5 | Z-3 | 1-methyl-piperidine |
| 787. | G-1 | Z-3 | 1-methyl-piperidine |
| 788. | G-2 | Z-3 | 1-methyl-piperidine |
| 789. | G-3 | Z-3 | 1-methyl-piperidine |
| 790. | G-8 | Z-3 | 1-methyl-piperidine |
| 791. | G-4 | Z-3 | 1-methyl-piperidine |
| 792. | G-6 | Z-6 | 1-methyl-piperidine |
| 793. | G-5 | Z-6 | 1-methyl-piperidine |
| 794. | G-1 | Z-6 | 1-methyl-piperidine |
| 795. | G-2 | Z-6 | 1-methyl-piperidine |
| 796. | G-3 | Z-6 | 1-methyl-piperidine |
| 797. | G-8 | Z-6 | 1-methyl-piperidine |
| 798. | G-4 | Z-6 | 1-methyl-piperidine |
| 799. | G-6 | Z-12 | 1-methyl-piperidine |
| 800. | G-5 | Z-12 | 1-methyl-piperidine |
| 801. | G-1 | Z-12 | 1-methyl-piperidine |
| 802. | G-2 | Z-12 | 1-methyl-piperidine |
| 803. | G-3 | Z-12 | 1-methyl-piperidine |
| 804. | G-8 | Z-12 | 1-methyl-piperidine |
| 805. | G-4 | Z-12 | 1-methyl-piperidine |
| 806. | G-6 | Z-11 | 1-methyl-piperidine |
| 807. | G-5 | Z-11 | 1-methyl-piperidine |
| 808. | G-1 | Z-11 | 1-methyl-piperidine |
| 809. | G-2 | Z-11 | 1-methyl-piperidine |
| 810. | G-3 | Z-11 | 1-methyl-piperidine |
| 811. | G-8 | Z-11 | 1-methyl-piperidine |
| 812. | G-4 | Z-11 | 1-methyl-piperidine |
| 813. | G-6 | Z-1 | 1-methyl-piperidine-A |
| 814. | G-5 | Z-1 | 1-methyl-piperidine-A |
| 815. | G-1 | Z-1 | 1-methyl-piperidine-A |
| 816. | G-2 | Z-1 | 1-methyl-piperidine-A |
| 817. | G-3 | Z-1 | 1-methyl-piperidine-A |
| 818. | G-8 | Z-1 | 1-methyl-piperidine-A |
| 819. | G-4 | Z-1 | 1-methyl-piperidine-A |
| 820. | G-6 | Z-2 | 1-methyl-piperidine-A |
| 821. | G-5 | Z-2 | 1-methyl-piperidine-A |
| 822. | G-1 | Z-2 | 1-methyl-piperidine-A |
| 823. | G-2 | Z-2 | 1-methyl-piperidine-A |
| 824. | G-3 | Z-2 | 1-methyl-piperidine-A |
| 825. | G-8 | Z-2 | 1-methyl-piperidine-A |
| 826. | G-4 | Z-2 | 1-methyl-piperidine-A |
| 827. | G-6 | Z-3 | 1-methyl-piperidine-A |
| 828. | G-5 | Z-3 | 1-methyl-piperidine-A |
| 829. | G-1 | Z-3 | 1-methyl-piperidine-A |
| 830. | G-2 | Z-3 | 1-methyl-piperidine-A |
| 831. | G-3 | Z-3 | 1-methyl-piperidine-A |
| 832. | G-8 | Z-3 | 1-methyl-piperidine-A |
| 833. | G-4 | Z-3 | 1-methyl-piperidine-A |
| 834. | G-6 | Z-6 | 1-methyl-piperidine-A |
| 835. | G-5 | Z-6 | 1-methyl-piperidine-A |
| 836. | G-1 | Z-6 | 1-methyl-piperidine-A |
| 837. | G-2 | Z-6 | 1-methyl-piperidine-A |
| 838. | G-3 | Z-6 | 1-methyl-piperidine-A |
| 839. | G-8 | Z-6 | 1-methyl-piperidine-A |
| 840. | G-4 | Z-6 | 1-methyl-piperidine-A |
| 841. | G-6 | Z-12 | 1-methyl-piperidine-A |
| 842. | G-5 | Z-12 | 1-methyl-piperidine-A |
| 843. | G-1 | Z-12 | 1-methyl-piperidine-A |
| 844. | G-2 | Z-12 | 1-methyl-piperidine-A |
| 845. | G-3 | Z-12 | 1-methyl-piperidine-A |
| 846. | G-8 | Z-12 | 1-methyl-piperidine-A |
| 847. | G-4 | Z-12 | 1-methyl-piperidine-A |
| 848. | G-6 | Z-11 | 1-methyl-piperidine-A |
| 849. | G-5 | Z-11 | 1-methyl-piperidine-A |
| 850. | G-1 | Z-11 | 1-methyl-piperidine-A |
| 851. | G-2 | Z-11 | 1-methyl-piperidine-A |
| 852. | G-3 | Z-11 | 1-methyl-piperidine-A |
| 853. | G-8 | Z-11 | 1-methyl-piperidine-A |
| 854. | G-4 | Z-11 | 1-methyl-piperidine-A |
| 855. | G-4 | Z-3 | 1-carbomethoxy-piperidine |
| 856. | G-4 | Z-6 | 1-carbomethoxy-piperidine |
| 857. | G-4 | Z-15 | 1-carbomethoxy-piperidine |
| 858. | G-4 | Z-16 | 1-carbomethoxy-piperidine |
| 859. | G-4 | Z-17 | 1-carbomethoxy-piperidine |
| 860. | G-4 | Z-18 | 1-carbomethoxy-piperidine |
| 861. | G-4 | Z-19 | 1-carbomethoxy-piperidine |
| 862. | G-4 | Z-3 | 1-carbomethoxy-piperidine-A |
| 863. | G-4 | Z-6 | 1-carbomethoxy-piperidine-A |
| 864. | G-4 | Z-15 | 1-carbomethoxy-piperidine-A |
| 865. | G-4 | Z-16 | 1-carbomethoxy-piperidine-A |
| 866. | G-4 | Z-17 | 1-carbomethoxy-piperidine-A |
| 867. | G-4 | Z-18 | 1-carbomethoxy-piperidine-A |
| 868. | G-4 | Z-19 | 1-carbomethoxy-piperidine-A |
| 869. | G-4 | Z-3 | 1-acetyl-piperidine |
| 870. | G-4 | Z-6 | 1-acetyl-piperidine |
| 871. | G-4 | Z-15 | 1-acetyl-piperidine |
| 872. | G-4 | Z-16 | 1-acetyl-piperidine |
| 873. | G-4 | Z-3 | 1-acetyl-piperidine-A |
| 874. | G-4 | Z-6 | 1-acetyl-piperidine-A |
| 875. | G-4 | Z-15 | 1-acetyl-piperidine-A |
| 876. | G-4 | Z-16 | 1-acetyl-piperidine-A |
| 877. | G-4 | Z-17 | 1-acetyl-piperidine-A |
| 878. | G-4 | Z-18 | 1-acetyl-piperidine-A |
| 879. | G-4 | Z-19 | 1-acetyl-piperidine-A |
| 880. | G-4 | Z-3 | 1-methylsulfonyl-piperidine |
| 881. | G-4 | Z-6 | 1-methylsulfonyl-piperidine |
| 882. | G-4 | Z-15 | 1-methylsulfonyl-piperidine |
| 883. | G-4 | Z-16 | 1-methylsulfonyl-piperidine |
| 884. | G-4 | Z-17 | 1-methylsulfonyl-piperidine |
| 885. | G-4 | Z-18 | 1-methylsulfonyl-piperidine |
| 886. | G-4 | Z-19 | 1-methylsulfonyl-piperidine |
| 887. | G-4 | Z-3 | 1-methylsulfonyl-piperidine-A |
| 888. | G-4 | Z-6 | 1-methylsulfonyl-piperidine-A |
| 889. | G-4 | Z-15 | 1-methylsulfonyl-piperidine-A |
| 890. | G-4 | Z-16 | 1-methylsulfonyl-piperidine-A |
| 891. | G-4 | Z-17 | 1-methylsulfonyl-piperidine-A |
| 892. | G-4 | Z-18 | 1-methylsulfonyl-piperidine-A |
| 893. | G-4 | Z-19 | 1-methylsulfonyl-piperidine-A |
| 894. | G-4 | Z-3 | 1-dimethylaminocarbonyl-piperidine |
| 895. | G-4 | Z-6 | 1-dimethylaminocarbonyl-piperidine |
| 896. | G-4 | Z-15 | 1-dimethylaminocarbonyl-piperidine |
| 897. | G-4 | Z-16 | 1-dimethylaminocarbonyl-piperidine |
| 898. | G-4 | Z-17 | 1-dimethylaminocarbonyl-piperidine |
| 899. | G-4 | Z-18 | 1-dimethylaminocarbonyl-piperidine |
| 900. | G-4 | Z-19 | 1-dimethylaminocarbonyl-piperidine |
| 901. | G-4 | Z-3 | 1-dimethylaminocarbonyl-piperidine-A |
| 902. | G-4 | Z-6 | 1-dimethylaminocarbonyl-piperidine-A |
| 903. | G-4 | Z-15 | 1-dimethylaminocarbonyl-piperidine-A |
| 904. | G-4 | Z-16 | 1-dimethylaminocarbonyl-piperidine-A |
| 905. | G-4 | Z-17 | 1-dimethylaminocarbonyl-piperidine-A |
| 906. | G-4 | Z-18 | 1-dimethylaminocarbonyl-piperidine-A |
| 907. | G-4 | Z-19 | 1-dimethylaminocarbonyl-piperidine-A |
| 908. | G-4 | Z-3 | 1-cyclopropylcarbonyl-piperidine |
| 909. | G-4 | Z-6 | 1-cyclopropylcarbonyl-piperidine |

TABLE 1-continued

| | | | |
|---|---|---|---|
| 910. | G-4 | Z-15 | 1-cyclopropylcarbonyl-piperidine |
| 911. | G-4 | Z-16 | 1-cyclopropylcarbonyl-piperidine |
| 912. | G-4 | Z-17 | 1-cyclopropylcarbonyl-piperidine |
| 913. | G-4 | Z-3 | 1-cyclopropylcarbonyl-piperidine-A |
| 914. | G-4 | Z-6 | 1-cyclopropylcarbonyl-piperidine-A |
| 915. | G-4 | Z-15 | 1-cyclopropylcarbonyl-piperidine-A |
| 916. | G-4 | Z-16 | 1-cyclopropylcarbonyl-piperidine-A |
| 917. | G-4 | Z-17 | 1-cyclopropylcarbonyl-piperidine-A |
| 918. | G-4 | Z-3 | 1-methoxy-cyclopropylcarbonyl-piperidine |
| 919. | G-4 | Z-6 | 1-methoxy-cyclopropylcarbonyl-piperidine |
| 920. | G-4 | Z-15 | 1-methoxy-cyclopropylcarbonyl-piperidine |
| 921. | G-4 | Z-16 | 1-methoxy-cyclopropylcarbonyl-piperidine |
| 922. | G-4 | Z-17 | 1-methoxy-cyclopropylcarbonyl-piperidine |
| 923. | G-4 | Z-3 | 1-methoxy-cyclopropylcarbonyl-piperidine-A |
| 924. | G-4 | Z-6 | 1-methoxy-cyclopropylcarbonyl-piperidine-A |
| 925. | G-4 | Z-15 | 1-methoxy-cyclopropylcarbonyl-piperidine-A |
| 926. | G-4 | Z-16 | 1-methoxy-cyclopropylcarbonyl-piperidine-A |
| 927. | G-4 | Z-17 | 1-methoxy-cyclopropylcarbonyl-piperidine-A |
| 928. | G-6 | Z-1 | tetrahydrothiopyran-dioxide |
| 929. | G-5 | Z-1 | tetrahydrothiopyran-dioxide |
| 930. | G-1 | Z-1 | tetrahydrothiopyran-dioxide |
| 931. | G-2 | Z-1 | tetrahydrothiopyran-dioxide |
| 932. | G-3 | Z-1 | tetrahydrothiopyran-dioxide |
| 933. | G-8 | Z-1 | tetrahydrothiopyran-dioxide |
| 934. | G-4 | Z-1 | tetrahydrothiopyran-dioxide |
| 935. | G-6 | Z-2 | tetrahydrothiopyran-dioxide |
| 936. | G-5 | Z-2 | tetrahydrothiopyran-dioxide |
| 937. | G-1 | Z-2 | tetrahydrothiopyran-dioxide |
| 938. | G-2 | Z-2 | tetrahydrothiopyran-dioxide |
| 939. | G-3 | Z-2 | tetrahydrothiopyran-dioxide |
| 940. | G-8 | Z-2 | tetrahydrothiopyran-dioxide |
| 941. | G-4 | Z-2 | tetrahydrothiopyran-dioxide |
| 942. | G-6 | Z-3 | tetrahydrothiopyran-dioxide |
| 943. | G-5 | Z-3 | tetrahydrothiopyran-dioxide |
| 944. | G-1 | Z-3 | tetrahydrothiopyran-dioxide |
| 945. | G-2 | Z-3 | tetrahydrothiopyran-dioxide |
| 946. | G-3 | Z-3 | tetrahydrothiopyran-dioxide |
| 947. | G-8 | Z-3 | tetrahydrothiopyran-dioxide |
| 948. | G-4 | Z-3 | tetrahydrothiopyran-dioxide |
| 949. | G-6 | Z-6 | tetrahydrothiopyran-dioxide |
| 950. | G-5 | Z-6 | tetrahydrothiopyran-dioxide |
| 951. | G-1 | Z-6 | tetrahydrothiopyran-dioxide |
| 952. | G-2 | Z-6 | tetrahydrothiopyran-dioxide |
| 953. | G-3 | Z-6 | tetrahydrothiopyran-dioxide |
| 954. | G-8 | Z-6 | tetrahydrothiopyran-dioxide |
| 955. | G-4 | Z-6 | tetrahydrothiopyran-dioxide |
| 956. | G-6 | Z-12 | tetrahydrothiopyran-dioxide |
| 957. | G-5 | Z-12 | tetrahydrothiopyran-dioxide |
| 958. | G-1 | Z-12 | tetrahydrothiopyran-dioxide |
| 959. | G-2 | Z-12 | tetrahydrothiopyran-dioxide |
| 960. | G-3 | Z-12 | tetrahydrothiopyran-dioxide |
| 961. | G-8 | Z-12 | tetrahydrothiopyran-dioxide |
| 962. | G-4 | Z-12 | tetrahydrothiopyran-dioxide |
| 963. | G-6 | Z-11 | tetrahydrothiopyran-dioxide |
| 964. | G-5 | Z-11 | tetrahydrothiopyran-dioxide |
| 965. | G-1 | Z-11 | tetrahydrothiopyran-dioxide |
| 966. | G-2 | Z-11 | tetrahydrothiopyran-dioxide |
| 967. | G-3 | Z-11 | tetrahydrothiopyran-dioxide |
| 968. | G-8 | Z-11 | tetrahydrothiopyran-dioxide |
| 969. | G-4 | Z-11 | tetrahydrothiopyran-dioxide |
| 970. | G-4 | Z-17 | tetrahydrothiopyran-dioxide |
| 971. | G-4 | Z-1 | tetrahydrothiopyran-dioxide-A |
| 972. | G-4 | Z-2 | tetrahydrothiopyran-dioxide-A |
| 973. | G-4 | Z-6 | tetrahydrothiopyran-dioxide-A |
| 974. | G-4 | Z-17 | tetrahydrothiopyran-dioxide-A |
| 975. | G-6 | Z-11 | 1,2,3,4-tetrahydro-naphthalen-1-yl |
| 976. | G-5 | Z-11 | 1,2,3,4-tetrahydro-naphthalen-1-yl |
| 977. | G-1 | Z-11 | 1,2,3,4-tetrahydro-naphthalen-1-yl |
| 978. | G-2 | Z-11 | 1,2,3,4-tetrahydro-naphthalen-1-yl |
| 979. | G-3 | Z-11 | 1,2,3,4-tetrahydro-naphthalen-1-yl |
| 980. | G-8 | Z-11 | 1,2,3,4-tetrahydro-naphthalen-1-yl |
| 981. | G-4 | Z-11 | 1,2,3,4-tetrahydro-naphthalen-1-yl |
| 982. | G-6 | Z-12 | 1,2,3,4-tetrahydro-naphthalen-1-yl |
| 983. | G-5 | Z-12 | 1,2,3,4-tetrahydro-naphthalen-1-yl |
| 984. | G-1 | Z-12 | 1,2,3,4-tetrahydro-naphthalen-1-yl |
| 985. | G-2 | Z-12 | 1,2,3,4-tetrahydro-naphthalen-1-yl |
| 986. | G-3 | Z-12 | 1,2,3,4-tetrahydro-naphthalen-1-yl |
| 987. | G-8 | Z-12 | 1,2,3,4-tetrahydro-naphthalen-1-yl |
| 988. | G-4 | Z-12 | 1,2,3,4-tetrahydro-naphthalen-1-yl |
| 989. | G-6 | Z-6 | 1,2,3,4-tetrahydro-naphthalen-1-yl |
| 990. | G-5 | Z-6 | 1,2,3,4-tetrahydro-naphthalen-1-yl |
| 991. | G-1 | Z-6 | 1,2,3,4-tetrahydro-naphthalen-1-yl |
| 992. | G-2 | Z-6 | 1,2,3,4-tetrahydro-naphthalen-1-yl |
| 993. | G-3 | Z-6 | 1,2,3,4-tetrahydro-naphthalen-1-yl |
| 994. | G-8 | Z-6 | 1,2,3,4-tetrahydro-naphthalen-1-yl |
| 995. | G-4 | Z-6 | 1,2,3,4-tetrahydro-naphthalen-1-yl |
| 996. | G-6 | Z-3 | 1,2,3,4-tetrahydro-naphthalen-1-yl |
| 997. | G-5 | Z-3 | 1,2,3,4-tetrahydro-naphthalen-1-yl |
| 998. | G-1 | Z-3 | 1,2,3,4-tetrahydro-naphthalen-1-yl |
| 999. | G-2 | Z-3 | 1,2,3,4-tetrahydro-naphthalen-1-yl |
| 1000. | G-3 | Z-3 | 1,2,3,4-tetrahydro-naphthalen-1-yl |
| 1001. | G-8 | Z-3 | 1,2,3,4-tetrahydro-naphthalen-1-yl |
| 1002. | G-4 | Z-3 | 1,2,3,4-tetrahydro-naphthalen-1-yl |
| 1003. | G-6 | Z-2 | 1,2,3,4-tetrahydro-naphthalen-1-yl |
| 1004. | G-5 | Z-2 | 1,2,3,4-tetrahydro-naphthalen-1-yl |
| 1005. | G-1 | Z-2 | 1,2,3,4-tetrahydro-naphthalen-1-yl |
| 1006. | G-2 | Z-2 | 1,2,3,4-tetrahydro-naphthalen-1-yl |
| 1007. | G-3 | Z-2 | 1,2,3,4-tetrahydro-naphthalen-1-yl |
| 1008. | G-8 | Z-2 | 1,2,3,4-tetrahydro-naphthalen-1-yl |
| 1009. | G-4 | Z-2 | 1,2,3,4-tetrahydro-naphthalen-1-yl |
| 1010. | G-6 | Z-1 | 1,2,3,4-tetrahydro-naphthalen-1-yl |
| 1011. | G-5 | Z-1 | 1,2,3,4-tetrahydro-naphthalen-1-yl |
| 1012. | G-1 | Z-1 | 1,2,3,4-tetrahydro-naphthalen-1-yl |
| 1013. | G-2 | Z-1 | 1,2,3,4-tetrahydro-naphthalen-1-yl |
| 1014. | G-3 | Z-1 | 1,2,3,4-tetrahydro-naphthalen-1-yl |
| 1015. | G-8 | Z-1 | 1,2,3,4-tetrahydro-naphthalen-1-yl |
| 1016. | G-4 | Z-1 | 1,2,3,4-tetrahydro-naphthalen-1-yl |
| 1017. | G-4 | Z-17 | 1,2,3,4-tetrahydro-naphthalen-1-yl |
| 1018. | G-4 | Z-21 | 1,2,3,4-tetrahydro-naphthalen-1-yl |
| 1019. | G-4 | Z-13 | 1,2,3,4-tetrahydro-naphthalen-1-yl |
| 1020. | G-4 | Z-1 | 1,2,3,4-tetrahydro-naphthalen-1-yl-A |
| 1021. | G-4 | Z-2 | 1,2,3,4-tetrahydro-naphthalen-1-yl-A |
| 1022. | G-4 | 1-3 | 1,2,3,4-tetrahydro-naphthalen-1-yl-A |
| 1023. | G-4 | Z-6 | 1,2,3,4-tetrahydro-naphthalen-1-yl-A |
| 1024. | G-4 | Z-17 | 1,2,3,4-tetrahydro-naphthalen-1-yl-A |
| 1025. | G-4 | Z-2 | 1,2,3,4-tetrahydro-naphthalen-1-yl-A |
| 1026. | G-4 | Z-13 | 1,2,3,4-tetrahydro-naphthalen-1-yl-A |
| 1027. | G-6 | Z-11 | 1,2,3,4-tetrahydro-naphthalen-2-yl |
| 1028. | G-5 | Z-11 | 1,2,3,4-tetrahydro-naphthalen-2-yl |
| 1029. | G-1 | Z-11 | 1,2,3,4-tetrahydro-naphthalen-2-yl |
| 1030. | G-2 | Z-11 | 1,2,3,4-tetrahydro-naphthalen-2-yl |
| 1031. | G-3 | Z-11 | 1,2,3,4-tetrahydro-naphthalen-2-yl |
| 1032. | G-8 | Z-11 | 1,2,3,4-tetrahydro-naphthalen-2-yl |
| 1033. | G-4 | Z-11 | 1,2,3,4-tetrahydro-naphthalen-2-yl |
| 1034. | G-6 | Z-12 | 1,2,3,4-tetrahydro-naphthalen-2-yl |
| 1035. | G-5 | Z-12 | 1,2,3,4-tetrahydro-naphthalen-2-yl |
| 1036. | G-1 | Z-12 | 1,2,3,4-tetrahydro-naphthalen-2-yl |
| 1037. | G-2 | Z-12 | 1,2,3,4-tetrahydro-naphthalen-2-yl |
| 1038. | G-3 | Z-12 | 1,2,3,4-tetrahydro-naphthalen-2-yl |
| 1039. | G-8 | Z-12 | 1,2,3,4-tetrahydro-naphthalen-2-yl |
| 1040. | G-4 | Z-12 | 1,2,3,4-tetrahydro-naphthalen-2-yl |
| 1041. | G-6 | Z-6 | 1,2,3,4-tetrahydro-naphthalen-2-yl |
| 1042. | G-5 | Z-6 | 1,2,3,4-tetrahydro-naphthalen-2-yl |
| 1043. | G-1 | Z-6 | 1,2,3,4-tetrahydro-naphthalen-2-yl |
| 1044. | G-2 | Z-6 | 1,2,3,4-tetrahydro-naphthalen-2-yl |
| 1045. | G-3 | Z-6 | 1,2,3,4-tetrahydro-naphthalen-2-yl |
| 1046. | G-8 | Z-6 | 1,2,3,4-tetrahydro-naphthalen-2-yl |
| 1047. | G-4 | Z-6 | 1,2,3,4-tetrahydro-naphthalen-2-yl |
| 1048. | G-6 | Z-3 | 1,2,3,4-tetrahydro-naphthalen-2-yl |
| 1049. | G-5 | Z-6 | 1,2,3,4-tetrahydro-naphthalen-2-yl |
| 1050. | G-1 | Z-3 | 1,2,3,4-tetrahydro-naphthalen-2-yl |
| 1051. | G-2 | Z-3 | 1,2,3,4-tetrahydro-naphthalen-2-yl |
| 1052. | G-3 | Z-3 | 1,2,3,4-tetrahydro-naphthalen-2-yl |
| 1053. | G-8 | Z-3 | 1,2,3,4-tetrahydro-naphthalen-2-yl |
| 1054. | G-4 | Z-3 | 1,2,3,4-tetrahydro-naphthalen-2-yl |
| 1055. | G-6 | Z-2 | 1,2,3,4-tetrahydro-naphthalen-2-yl |
| 1056. | G-5 | Z-2 | 1,2,3,4-tetrahydro-naphthalen-2-yl |
| 1057. | G-1 | Z-2 | 1,2,3,4-tetrahydro-naphthalen-2-yl |
| 1058. | G-2 | Z-2 | 1,2,3,4-tetrahydro-naphthalen-2-yl |
| 1059. | G-3 | Z-2 | 1,2,3,4-tetrahydro-naphthalen-2-yl |
| 1060. | G-8 | Z-2 | 1,2,3,4-tetrahydro-naphthalen-2-yl |
| 1061. | G-4 | Z-2 | 1,2,3,4-tetrahydro-naphthalen-2-yl |
| 1062. | G-6 | Z-1 | 1,2,3,4-tetrahydro-naphthalen-2-yl |
| 1063. | G-5 | Z-1 | 1,2,3,4-tetrahydro-naphthalen-2-yl |
| 1064. | G-1 | Z-1 | 1,2,3,4-tetrahydro-naphthalen-2-yl |
| 1065. | G-2 | Z-1 | 1,2,3,4-tetrahydro-naphthalen-2-yl |
| 1066. | G-3 | Z-1 | 1,2,3,4-tetrahydro-naphthalen-2-yl |
| 1067. | G-8 | Z-1 | 1,2,3,4-tetrahydro-naphthalen-2-yl |

TABLE 1-continued

| | | | |
|---|---|---|---|
| 1068. | G-4 | Z-1 | 1,2,3,4-tetrahydro-naphthalen-2-yl |
| 1069. | G-4 | Z-17 | 1,2,3,4-tetrahydro-naphthalen-2-yl |
| 1070. | G-4 | Z-21 | 1,2,3,4-tetrahydro-naphthalen-2-yl |
| 1071. | G-4 | Z-13 | 1,2,3,4-tetrahydro-naphthalen-1-yl |
| 1072. | G-6 | Z-11 | bicyclo[2.2.1]hept-2-yl |
| 1073. | G-5 | Z-11 | bicyclo[2.2.1]hept-2-yl |
| 1074. | G-1 | Z-11 | bicyclo[2.2.1]hept-2-yl |
| 1075. | G-2 | Z-11 | bicyclo[2.2.1]hept-2-yl |
| 1076. | G-3 | Z-11 | bicyclo[2.2.1]hept-2-yl |
| 1077. | G-8 | Z-11 | bicyclo[2.2.1]hept-2-yl |
| 1078. | G-4 | Z-11 | bicyclo[2.2.1]hept-2-yl |
| 1079. | G-6 | Z-12 | bicyclo[2.2.1]hept-2-yl |
| 1080. | G-5 | Z-12 | bicyclo[2.2.1]hept-2-yl |
| 1081. | G-1 | Z-12 | bicyclo[2.2.1]hept-2-yl |
| 1082. | G-2 | Z-12 | bicyclo[2.2.1]hept-2-yl |
| 1083. | G-3 | Z-12 | bicyclo[2.2.1]hept-2-yl |
| 1084. | G-8 | Z-12 | bicyclo[2.2.1]hept-2-yl |
| 1085. | G-4 | Z-12 | bicyclo[2.2.1]hept-2-yl |
| 1086. | G-6 | Z-6 | bicyclo[2.2.1]hept-2-yl |
| 1087. | G-5 | Z-6 | bicyclo[2.2.1]hept-2-yl |
| 1088. | G-1 | Z-6 | bicyclo[2.2.1]hept-2-yl |
| 1089. | G-2 | Z-6 | bicyclo[2.2.1]hept-2-yl |
| 1090. | G-3 | Z-6 | bicyclo[2.2.1]hept-2-yl |
| 1091. | G-8 | Z-6 | bicyclo[2.2.1]hept-2-yl |
| 1092. | G-4 | Z-6 | bicyclo[2.2.1]hept-2-yl |
| 1093. | G-6 | Z-3 | bicyclo[2.2.1]hept-2-yl |
| 1094. | G-5 | Z-6 | bicyclo[2.2.1]hept-2-yl |
| 1095. | G-1 | Z-6 | bicyclo[2.2.1]hept-2-yl |
| 1096. | G-2 | Z-3 | bicyclo[2.2.1]hept-2-yl |
| 1097. | G-3 | Z-3 | bicyclo[2.2.1]hept-2-yl |
| 1098. | G-8 | Z-3 | bicyclo[2.2.1]hept-2-yl |
| 1099. | G-4 | Z-3 | bicyclo[2.2.1]hept-2-yl |
| 1100. | G-6 | Z-2 | bicyclo[2.2.1]hept-2-yl |
| 1101. | G-5 | Z-2 | bicyclo[2.2.1]hept-2-yl |
| 1102. | G-1 | Z-2 | bicyclo[2.2.1]hept-2-yl |
| 1103. | G-2 | Z-2 | bicyclo[2.2.1]hept-2-yl |
| 1104. | G-3 | Z-2 | bicyclo[2.2.1]hept-2-yl |
| 1105. | G-8 | Z-2 | bicyclo[2.2.1]hept-2-yl |
| 1106. | G-4 | Z-2 | bicyclo[2.2.1]hept-2-yl |
| 1107. | G-6 | Z-1 | bicyclo[2.2.1]hept-2-yl |
| 1108. | G-5 | Z-1 | bicyclo[2.2.1]hept-2-yl |
| 1109. | G-1 | Z-1 | bicyclo[2.2.1]hept-2-yl |
| 1110. | G-2 | Z-1 | bicyclo[2.2.1]hept-2-yl |
| 1111. | G-3 | Z-1 | bicyclo[2.2.1]hept-2-yl |
| 1112. | G-8 | Z-1 | bicyclo[2.2.1]hept-2-yl |
| 1113. | G-4 | Z-1 | bicyclo[2.2.1]hept-2-yl |
| 1114. | G-6 | Z-1 | bicyclo[2.2.1]hept-2-yl |
| 1115. | G-5 | Z-1 | bicyclo[2.2.1]hept-2-yl |
| 1116. | G-2 | Z-1 | bicyclo[2.2.1]hept-2-yl |
| 1117. | G-1 | Z-1 | bicyclo[2.2.1]hept-2-yl |
| 1118. | G-4 | Z-1 | bicyclo[2.2.1]hept-2-yl |
| 1119. | G-6 | Z-2 | bicyclo[2.2.1]hept-2-yl |
| 1120. | G-5 | Z-2 | bicyclo[2.2.1]hept-2-yl |
| 1121. | G-2 | Z-2 | bicyclo[2.2.1]hept-2-yl |
| 1122. | G-1 | Z-2 | bicyclo[2.2.1]hept-2-yl |
| 1123. | G-4 | Z-2 | bicyclo[2.2.1]hept-2-yl |
| 1124. | G-6 | Z-6 | bicyclo[2.2.1]hept-2-yl |
| 1125. | G-5 | Z-6 | bicyclo[2.2.1]hept-2-yl |
| 1126. | G-2 | Z-6 | bicyclo[2.2.1]hept-2-yl |
| 1127. | G-1 | Z-6 | bicyclo[2.2.1]hept-2-yl |
| 1128. | G-4 | Z-6 | bicyclo[2.2.1]hept-2-yl |
| 1129. | G-6 | Z-11 | bicyclo[2.2.1]hept-2-yl |
| 1130. | G-5 | Z-11 | bicyclo[2.2.1]hept-2-yl |
| 1131. | G-2 | Z-11 | bicyclo[2.2.1]hept-2-yl |
| 1132. | G-1 | Z-11 | bicyclo[2.2.1]hept-2-yl |
| 1133. | G-4 | Z-11 | bicyclo[2.2.1]hept-2-yl |
| 1134. | G-6 | Z-13 | bicyclo[2.2.1]hept-2-yl |
| 1135. | G-5 | Z-13 | bicyclo[2.2.1]hept-2-yl |
| 1136. | G-2 | Z-13 | bicyclo[2.2.1]hept-2-yl |
| 1137. | G-1 | Z-13 | bicyclo[2.2.1]hept-2-yl |
| 1138. | G-4 | Z-11 | bicyclo[2.2.1]hept-2-yl |
| 1139. | G-4 | Z-17 | bicyclo[2.2.1]hept-2-yl |
| 1140. | G-6 | Z-17 | bicyclo[2.2.1]hept-2-yl |
| 1141. | G-4 | Z-18 | bicyclo[2.2.1]hept-2-yl |
| 1142. | G-6 | Z-18 | bicyclo[2.2.1]hept-2-yl |
| 1143. | G-4 | Z-19 | bicyclo[2.2.1]hept-2-yl |
| 1144. | G-6 | Z-19 | bicyclo[2.2.1]hept-2-yl |
| 1145. | G-4 | Z-20 | bicyclo[2.2.1]hept-2-yl |
| 1146. | G-6 | Z-20 | bicyclo[2.2.1]hept-2-yl |

TABLE 1-continued

| | | | |
|---|---|---|---|
| 1147. | G-6 | Z-1 | 6,7-dihydro-5H-pyrrolo[1,2-c]imidazol-6-yl |
| 1148. | G-6 | Z-1 | 6,7-dihydro-5H-pyrrolo[1,2-a]imidazol-6-yl |
| 1149. | G-4 | Z-1 | 6,7-dihydro-5H-pyrrolo[1,2-c]imidazol-6-yl |
| 1150. | G-4 | Z-1 | 6,7-dihydro-5H-pyrrolo[1,2-a]imidazol-6-yl |
| 1151. | G-A | Z-1 | 5,6-dihydro-4H-pyrrolo[1,2-b]pyrazol-5-yl |
| 1152. | G-6 | Z-1 | 5,6-dihydro-4H-pyrrolo[1,2-b]pyrazol-5-yl |
| 1153. | G-4 | Z-17 | 6,7-dihydro-5H-pyrrolo[1,2-c]imidazol-6-yl |
| 1154. | G-6 | Z-17 | 6,7-dihydro-5H-pyrrolo[1,2-c]imidazol-6-yl |
| 1155. | G-4 | Z-21 | 6,7-dihydro-5H-pyrrolo[1,2-a]imidazol-6-yl |
| 1156. | G-6 | Z-21 | 6,7-dihydro-5H-pyrrolo[1,2-a]imidazol-6-yl |
| 1157. | G-4 | Z-6 | 5,6-dihydro-4H-pyrrolo[1,2-b]pyrazol-5-yl |
| 1158. | G-6 | Z-6 | 5,6-dihydro-4H-pyrrolo[1,2-b]pyrazol-5-yl |
| 1159. | G-4 | Z-17 | 5,6-dihydro-4H-pyrrolo[1,2-b]pyrazol-5-yl |
| 1160. | G-6 | Z-17 | 5,6-dihydro-4H-pyrrolo[1,2-b]pyrazol-5-yl |
| 1161. | G-4 | Z-1 | N-methyl-pyrrolidone |
| 1162. | G-4 | Z-2 | N-methyl-pyrrolidone |
| 1163. | G-4 | Z-3 | N-methyl-pyrrolidone |
| 1164. | G-4 | Z-6 | N-methyl-pyrrolidone |
| 1165. | G-6 | Z-1 | N-methyl-pyrrolidone |
| 1166. | G-6 | Z-2 | N-methyl-pyrrolidone |
| 1167. | G-6 | Z-3 | N-methyl-pyrrolidone |
| 1168. | G-6 | Z-6 | N-methyl-pyrrolidone |

Numerous modifications and variations of the present invention are possible in light of the above teachings. It is therefore to be understood that within the scope of the appended claims, the invention may be practiced otherwise that as specifically described herein.

What is claimed is:

1. A compound selected from the group consisting of:

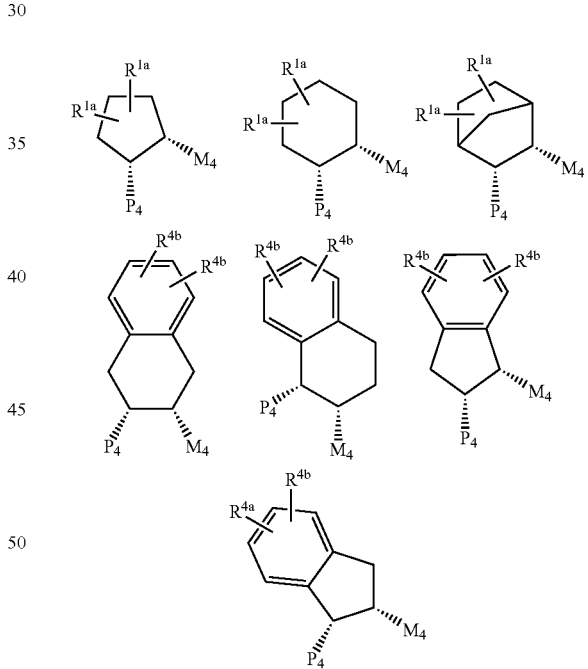

wherein:
   $P_4$ is -$G_1$-G;
   $M_4$ is -Z-A-B;
   G is selected from the group consisting of: phenyl; 4-ethyl-phenyl; 2-aminomethyl-4-chloro-phenyl; 2-aminosulfonyl-4-chloro-phenyl; 2-amido-4-chloro-phenyl; 4-chloro-2-methylsulfonyl-phenyl; 2-aminosulfonyl-4-fluoro-phenyl; 2-amido-4-fluoro-phenyl; 4-fluoro-2-methylsulfonyl-phenyl; 2-aminomethyl-4-bromo-phenyl; 2-aminosulfonyl-4-bromo-phenyl; 2-amido-4-bromo-phenyl; 4-bromo-2-methylsulfonylphenyl; 2-aminomethyl-4-methyl-phenyl; 2-aminosulfonyl-4-methyl-phenyl; 2-amido-4-methyl-phenyl; 2-methylsulfonyl-4-methyl-phenyl; 4-fluoro-pyrid-2-yl; 4-bromo-pyrid-2-yl; 4-methyl-pyrid-2-yl; 5-fluoro-thien-2-yl; 5-bromo-thien-2-yl; 5-methyl-thien-2-yl; 2-amido-4-methoxy-phenyl; 2-amido-phenyl; 2-aminomethyl-3-fluoro-phenyl; 2-aminomethyl-4-fluoro-phenyl; 2-aminomethyl-5-fluoro-phenyl; 2-aminomethyl-6-fluoro-phenyl; 2-aminomethyl-phenyl; 2-amino-pyrid-4-yl; 2-aminosulfonyl-4-methoxy-phenyl; 2-aminosulfonyl-phenyl; 3-amido-phenyl; 3-amino-4-chloro-phenyl; 3-aminomethyl-phenyl; 3-chloro-phenyl; 4-chloro-phenyl; 4-methoxy-phenyl; 2-methoxy-pyrid-5-yl; 5-chloro-pyrid-2-yl; 5-chloro-thien-2-yl; 6-amino-5-chloro-pyrid-2-yl; 6-amino-pyrid-2-yl; 2-cyano-4-chloro-phenyl; 2-methoxy-4-chloro-phenyl; 2-fluoro-4-chloro-phenyl; 3-fluoro-4-chloro-phenyl; 3-methyl-4-chloro-phenyl; 3-fluoro-4-methyl-phenyl; 3,4-dimethyl-phenyl; 3-chloro-4-fluoro-phenyl; 3-methyl-4-fluoro-phenyl; 4-methylsulfanyl-phenyl;

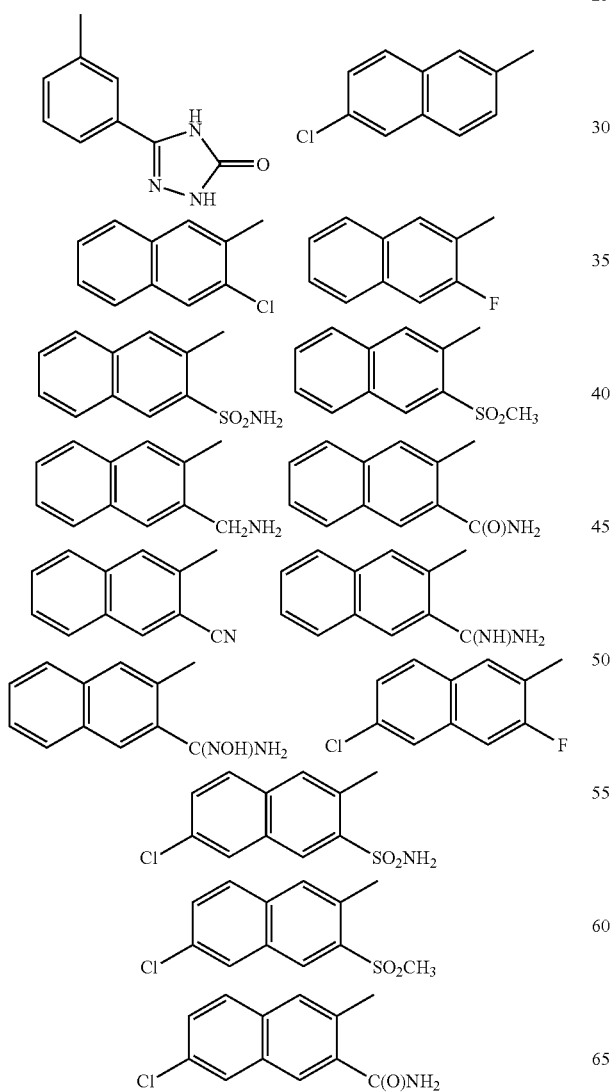

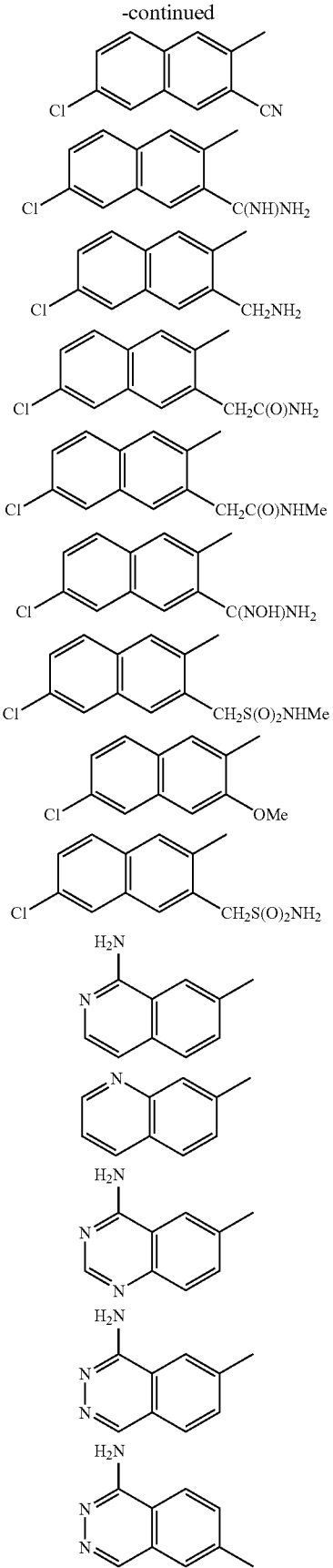

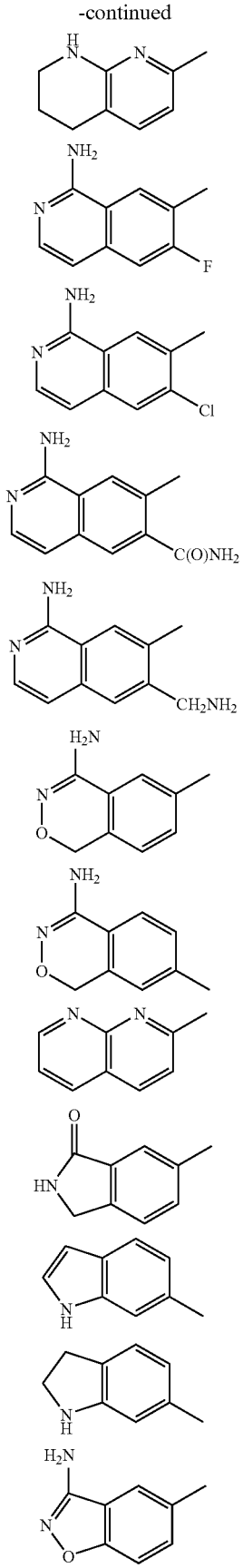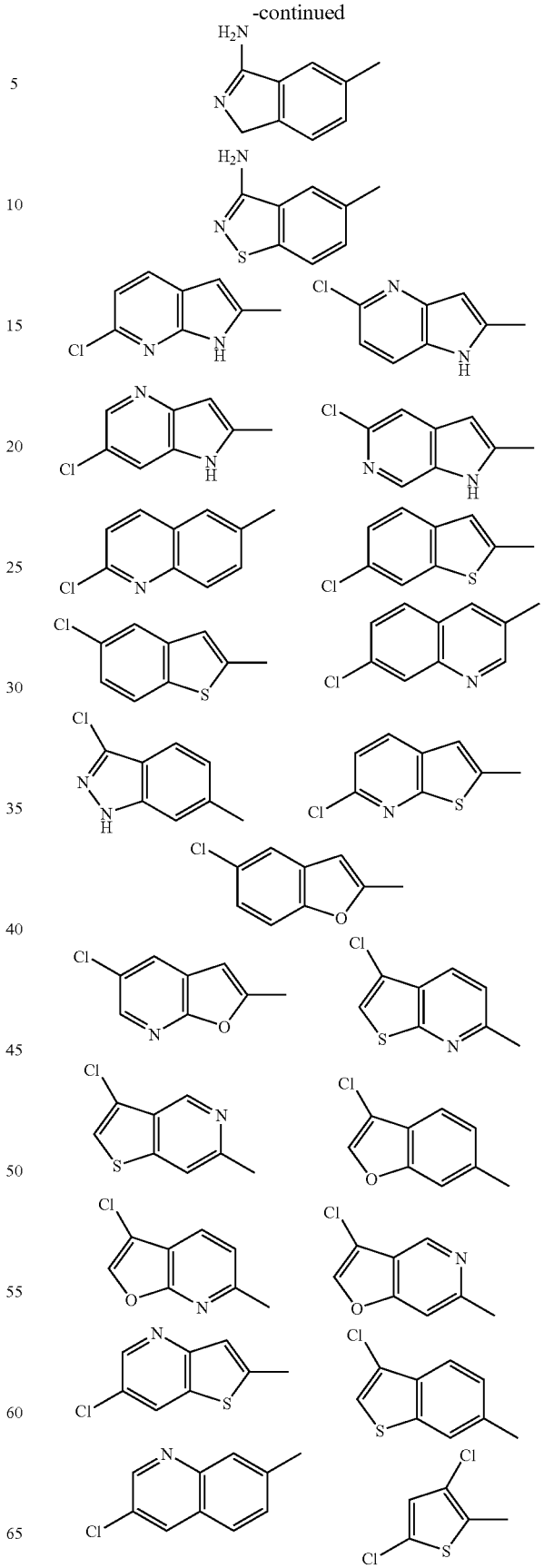

-continued

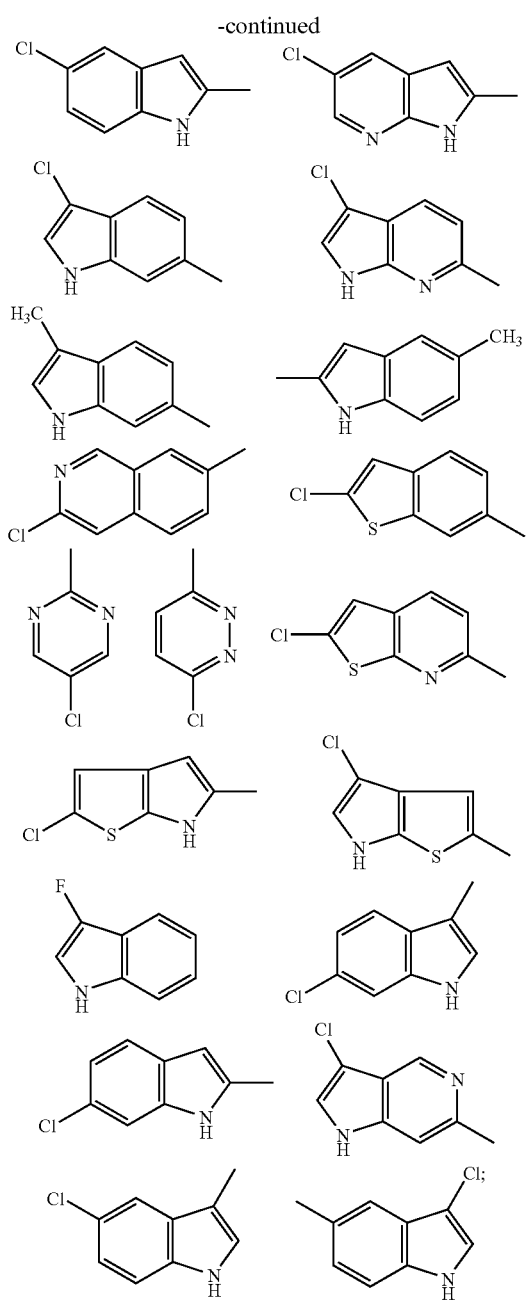

A is selected from the group consisting of: cyclohexyl, phenyl, 2-Cl-phenyl, 3-Cl-phenyl, 2-F-phenyl, 3-F-phenyl, 2-methylphenyl, 2-aminophenyl, and 2-methoxyphenyl;

B is selected from the group consisting of 4,5-dihydro-2-imdazolyl, imidazolyl, and benzimidazolyl, and is substituted with 0–1 $R^{4a}$;

$G_1$ is selected from the group consisting of NHC(O), wherein the left side of $G_1$ is attached to ring M;

Z is selected from the group consisting of NHC(O), wherein the left side of Z is attached to ring M;

$R^{1a}$ is selected from the group consisting of —H, $CH_3$, $CH_2CH_3$, $CH_2CH_2CH_3$, $OCH_3$, $CH_2OH$, $C(CH_3)_2OH$, $CH_2OCH_3$, $CH_2CH_2OCH_3$, $NH_2$, $CH_2NH_2$, $NHCH_3$, $CH_2NHCH_3$, $N(CH_3)_2$, $CH_2N(CH_3)_2$, $CO_2H$, $CH_2CO_2H$, $CH_2CH_2CO_2H$, $CH_2CH_2CO_2CH_2CH_3$, $COCH_3$, $COCH_2C(CH_3)_3$, $COCF_3$, $CO_2CH_3$, $CO_2CH_2CH_3$, $CO_2CH(CH_3)_2$, $CO_2C(CH_3)_3$, $CH_2CO_2CH_3$, $CH_2CH_2CO_2CH_2CH_3$, $S(O)_2CH_3$, $CH_2S(O)_2CH_3$, $C(O)NH_2$, $CONH(CH_3)$, $CONH(CH_2CH_3)$, $CONHC(CH_3)_3$, $CON(CH_3)_2$, $CON(CH_3)(CH_2CH_3)$, $CON(CH_3)CH(CH_3)_2$, $CH_2C(O)NH_2$, $CH_2CON(CH_3)_2$, $CSN(CH_3)_2$, $SO_2NH_2$, $CH_2SO_2NH_2$, $NHSO_2CH_3$, and $CH_2NHSO_2CH_3$;

alternatively, $R^{1a}$ is selected from the group consisting of:

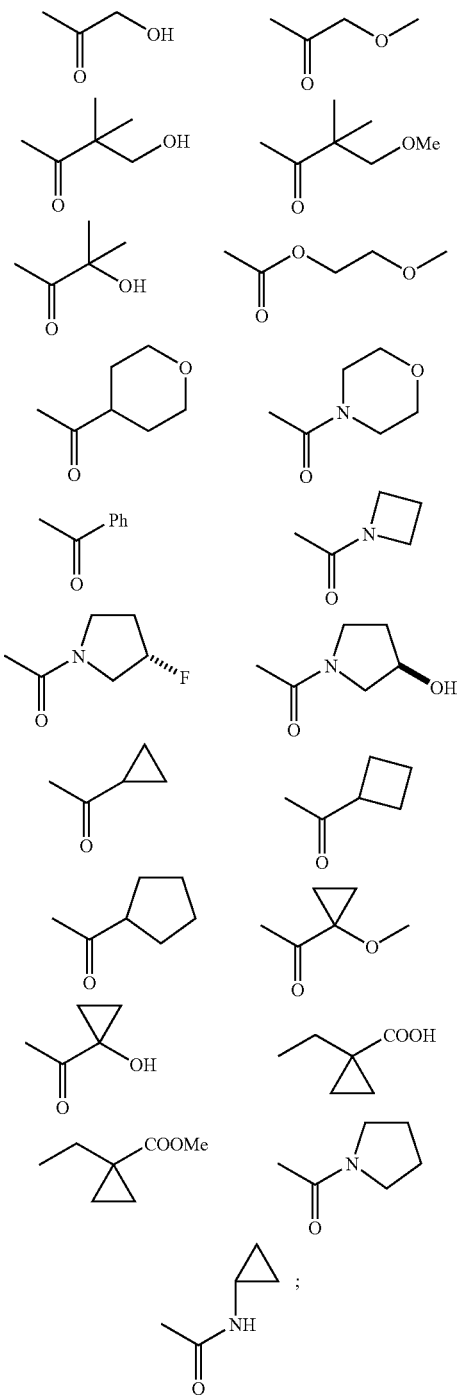

$R^2$, at each occurrence, is selected from the group consisting of H, $C_{1-3}$alkyl substituted with 0–1 $R^{4b}$, $C_{3-6}$cycloalkyl substituted with 0–1 $R^{4b}$, $CH_2$—$C_{3-6}$cycloalkyl substituted with 0–1 $R^{4b}$, phenyl substituted with 0–1 $R^{4b}$, benzyl substituted with 0–1 $R^{4b}$, and 5 membered aromatic heterocycle substituted with 0–1 $R^{4b}$ and consisting of: carbon atoms and 1–4 heteroatoms selected from the group consisting of N, O, and $S(O)_p$;

$R^{2a}$, at each occurrence, is selected from the group consisting of —H, $CH_3$, and $CH_2CH_3$;

alternatively, $NR^2R^{2a}$ forms a 5 or 6 membered saturated, partially saturated or unsaturated ring substituted with 0–1 $R^{4b}$ and consisting of: carbon atoms, the N of $NR^2R^{2a}$, and 0–1 additional heteroatoms selected from the group consisting of N, O, and $S(O)_p$;

$R^{2b}$, at each occurrence, is selected from the group consisting of —OH, $OCH_3$, $OCH_2CH_3$, $CH_3$, and $CH_2CH_3$;

$R^3$, at each occurrence, is selected from the group consisting of —H, $CH_3$, $CH_2CH_3$, $CH_2CH_2CH_3$, $CH(CH_3)_2$, benzyl, and phenyl;

$R^{3a}$, at each occurrence, is selected from the group consisting of —H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from the group consisting of —$CH_3$, $CH_2CH_3$, $CH_2CH_2CH_3$, $CH(CH_3)_2$, benzyl, and phenyl;

$R^{4a}$ is selected from the group consisting of —$C_{1-4}$alkyl, $CF_3$, $OR^2$, $CH_2OR^2$, $(CH_2)_2OR^2$, $NR^2R^{2a}$, $CH_2NR^2R^{2a}$, $(CH_2)_2NR^2R^{2a}$, $S(O)_pR^5$, $SO_2NR^2R^{2a}$, and 1-$CF_3$-tetrazol-2-yl;

$R^{4b}$, at each occurrence, is selected from the group consisting of —H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^5$, at each occurrence, is selected from the group consisting of —H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from the group consisting of —H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$; and p, at each occurrence, is selected from the group consisting of —0, 1, and 2.

2. A compound according to claim 1, selected from the group consisting of:

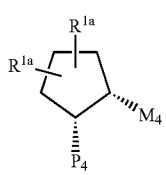 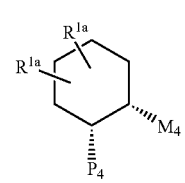

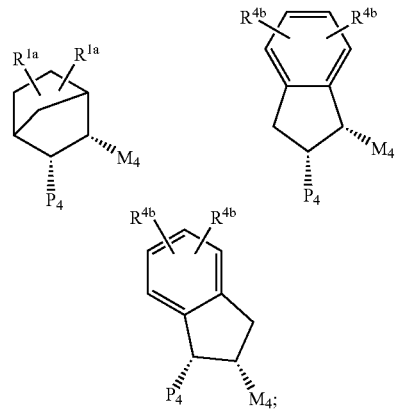

wherein:

G is selected from the group consisting of:

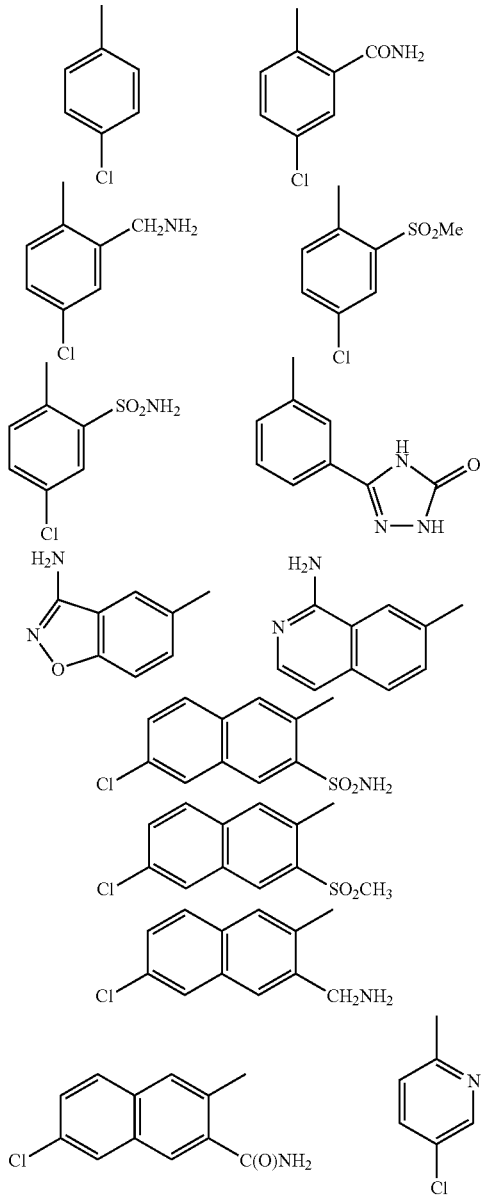

-continued

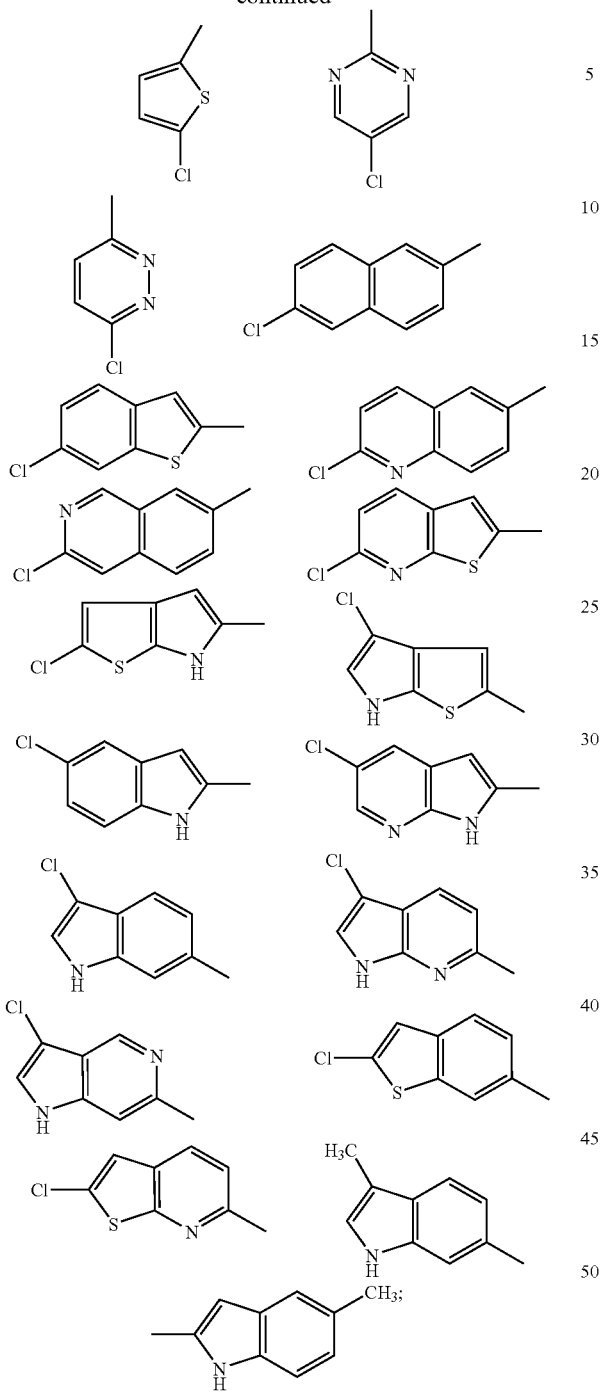

A is selected from the group consisting of: phenyl, 2-Cl-phenyl, 3-Cl-phenyl, 2-F-phenyl, 3-F-phenyl, 2-methylphenyl, 2-aminophenyl, and 2-methoxyphenyl; and B is selected from the group consisting of: 1-methyl-4,5-dihydro-2-imdazolyl, 1-methyl-2-imidazolyl, 2-methyl-1-imidazolyl, 2-(dimethylaminomethyl)-1-imidazolyl, 2-(methylaminomethyl)-1-imidazolyl, 2-(N-(cyclopropylmethyl)aminomethyl))-1-imidazolyl, 2-(N-(cyclobutyl)aminomethyl))-1-imidazolyl, 2-(N-(cyclopentyl)aminomethyl))-1-imidazolyl, 2-(N-(4-hydroxypiperidinyl)methyl))-1-imidazolyl, 2-(N-(3-hydroxypyrrolidinyl)methyl))-1-imidazolyl, and 2-(N-(2-ethanol)aminomethyl))-1-imidazolyl.

3. A compound according to claim 2, selected from the group consisting of:

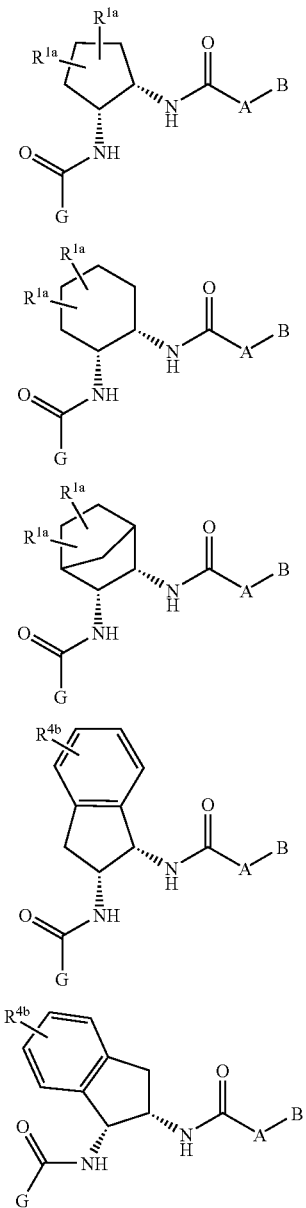

wherein:

G is selected from the group consisting of:

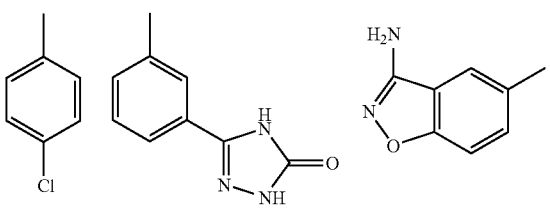

-continued

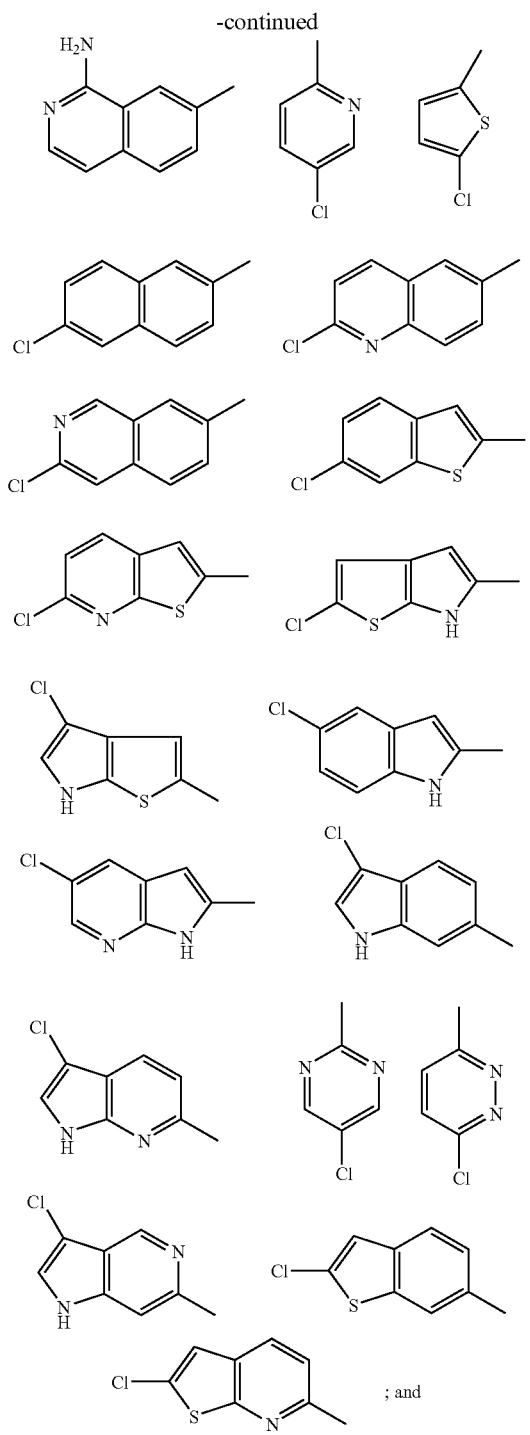

A-B is selected from the group consisting of:

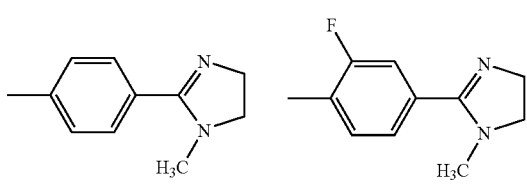

-continued

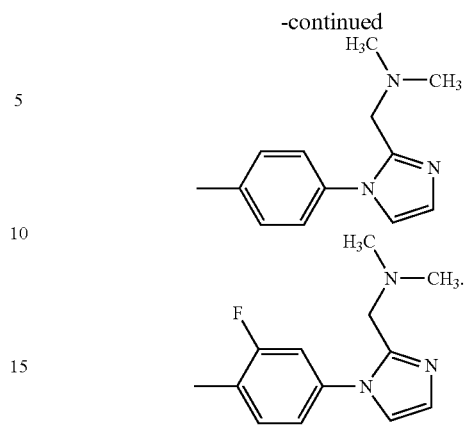

4. A compound according to claim 1, selected from the group consisting of:
(1R, 2S)-3-Chloro-1H-indole-6-carboxylic acid {2-[4-(2-dimethylaminomethyl-imidazol-1-yl)-benzoylamino]-cyclopentyl}-amide;
(1R, 2S)-5-Chloro-thiophene-2-carboxylic acid {2-[4-(2-dimethylaminomethylimidazol-1-yl)-benzoylamino]-cyclopentyl}-amide;
(1R, 2S)-5-Chloro-thiophene-2-carboxylic acid {2-[4-(2-dimethylaminomethyl-imidazol-1-yl)-benzoylamino]-cyclohexyl}-amide;
(1R, 2S)-3-Chloro-1H-indole-6-carboxylic acid {2-[4-(2-dimethylaminomethyl-imidazol-1-yl)-benzoylamino]-cyclohexyl}-amide;
(1R, 2S)-3-Chloro-1H-indole-6-carboxylic acid {2-[4-(2-dimethylaminomethyl-imidazol-1-yl)-benzoylamino]-indan-1-yl}-amide;
or a pharmaceutically acceptable salt form thereof.

5. A pharmaceutical composition, comprising: a pharmaceutically acceptable carrier and a therapeutically effective amount of a compound of claim 1 or a pharmaceutically acceptable salt thereof.

6. A method for treating a thromboembolic disorder, comprising: administering to a patient in need thereof a therapeutically effective amount of a compound of claim 1 or a pharmaceutically acceptable salt thereof.

7. A method according to claim 6, wherein the thromboembolic disorder is selected from the group consisting of arterial cardiovascular thromboembolic disorders, venous cardiovascular thromboembolic disorders, and thromboembolic disorders in the chambers of the heart.

8. A method according to claim 6, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

9. A pharmaceutical composition, comprising: a pharmaceutically acceptable carrier and a therapeutically effective amount of a compound of claim 2 or a pharmaceutically acceptable salt thereof.

10. A pharmaceutical composition, comprising: a pharmaceutically acceptable carrier and a therapeutically effective amount of a compound of claim 3 or a pharmaceutically acceptable salt thereof.

11. A pharmaceutical composition, comprising: a pharmaceutically acceptable carrier and a therapeutically effective amount of a compound of claim 4 or a pharmaceutically acceptable salt thereof.

12. A method for treating a thromboembolic disorder, comprising: administering to a patient in need thereof a therapeutically effective amount of a compound of claim 2 or a pharmaceutically acceptable salt thereof.

13. A method according to claim 12, wherein the thromboembolic disorder is selected from the group consisting of arterial cardiovascular thromboembolic disorders, venous cardiovascular thromboembolic disorders, and thromboembolic disorders in the chambers of the heart.

14. A method according to claim 12, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

15. A method for treating a thromboembolic disorder, comprising: administering to a patient in need thereof a therapeutically effective amount of a compound of claim 3 or a pharmaceutically acceptable salt thereof.

16. A method according to claim 15, wherein the thromboembolic disorder is selected from the group consisting of arterial cardiovascular thromboembolic disorders, venous cardiovascular thromboembolic disorders, and thromboembolic disorders in the chambers of the heart.

17. A method according to claim 15, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

18. A method for treating a thromboembolic disorder, comprising: administering to a patient in need thereof a therapeutically effective amount of a compound of claim 4 or a pharmaceutically acceptable salt thereof.

19. A method according to claim 18, wherein the thromboembolic disorder is selected from the group consisting of arterial cardiovascular thromboembolic disorders, venous cardiovascular thromboembolic disorders, and thromboembolic disorders in the chambers of the heart.

20. A method according to claim 18, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

\* \* \* \* \*